(12) United States Patent
Adiri et al.

(10) Patent No.: US 11,749,399 B2
(45) Date of Patent: *Sep. 5, 2023

(54) CROSS SECTION VIEWS OF WOUNDS

(71) Applicant: HEALTHY.IO LTD, Tel Aviv (IL)

(72) Inventors: Yonatan Adiri, Tel Aviv (IL); Ron Zohar, Tel Aviv (IL); Ido Omer, Tel Aviv (IL); Nathaniel Bubis, Tel Aviv (IL)

(73) Assignee: HEALTHY.IO LTD, Tel Aviv (IL)

(*) Notice: Subject to any disclaimer, the term of this patent is extended or adjusted under 35 U.S.C. 154(b) by 0 days.

This patent is subject to a terminal disclaimer.

(21) Appl. No.: 17/956,955

(22) Filed: Sep. 30, 2022

(65) Prior Publication Data

US 2023/0094442 A1 Mar. 30, 2023

Related U.S. Application Data

(63) Continuation of application No. 17/646,998, filed on Jan. 4, 2022, now Pat. No. 11,494,909.

(Continued)

(51) Int. Cl.
*G06T 7/00* (2017.01)
*G06T 15/20* (2011.01)
(Continued)

(52) U.S. Cl.
CPC ............ *G16H 30/20* (2018.01); *A61B 5/0013* (2013.01); *A61B 5/0015* (2013.01); *A61B 5/0077* (2013.01); *A61B 5/445* (2013.01); *A61B 5/6898* (2013.01); *A61B 34/10* (2016.02); *G02B 27/0101* (2013.01); *G06T 7/0012* (2013.01); *G06T 7/0014* (2013.01); *G06T 7/0016* (2013.01); *G06T 7/50* (2017.01); *G06T 7/62* (2017.01); *G06T 7/70* (2017.01); *G06T 7/80* (2017.01); *G06T 7/90* (2017.01); *G06T 11/00* (2013.01); *G06T 11/001* (2013.01); *G06T 11/203* (2013.01); *G06T 15/205* (2013.01); *G06V 10/25* (2022.01); *G06V 10/60* (2022.01); *G06V 10/94* (2022.01); *G06V 20/00* (2022.01); *G16H 20/10* (2018.01); *G16H 30/40* (2018.01); *G16H 40/60* (2018.01); *G16H 40/67* (2018.01); *G16H 50/50* (2018.01); *G16H 80/00* (2018.01);
(Continued)

(58) Field of Classification Search
CPC .................. G06T 7/0012; G06T 15/205; G06T 2207/10028; G06T 2207/30004; G06T 2210/41
See application file for complete search history.

(56) References Cited

U.S. PATENT DOCUMENTS

2021/0290152 A1* 9/2021 Vogel ..................... G16H 20/40

* cited by examiner

*Primary Examiner* — Siamak Harandi
(74) *Attorney, Agent, or Firm* — Finnegan, Henderson, Farabow, Garrett & Dunner, LLP

(57) ABSTRACT

A non-transitory computer readable medium storing data and computer implementable instructions that, when executed by at least one processor, cause the at least one processor to perform operations for generating cross section views of a wound, the operations including receiving 3D information of a wound based on information captured using an image sensor associated with an image plane substantially parallel to the wound; generating a cross section view of the wound by analyzing the 3D information; and providing data configured to cause a presentation of the generated cross section view of the wound.

19 Claims, 42 Drawing Sheets

Related U.S. Application Data

(60) Provisional application No. 63/133,573, filed on Jan. 4, 2021, provisional application No. 63/195,357, filed on Jun. 1, 2021.

(51) Int. Cl.

| | |
|---|---|
| *G16H 30/20* | (2018.01) |
| *A61B 5/00* | (2006.01) |
| *G16H 40/60* | (2018.01) |
| *G16H 20/10* | (2018.01) |
| *G16H 80/00* | (2018.01) |
| *G16H 40/67* | (2018.01) |
| *G06V 20/00* | (2022.01) |
| *G06T 7/70* | (2017.01) |
| *G16H 30/40* | (2018.01) |
| *G06T 11/00* | (2006.01) |
| *G16H 50/50* | (2018.01) |
| *G06V 10/25* | (2022.01) |
| *G06T 7/50* | (2017.01) |
| *G06T 7/90* | (2017.01) |
| *G06T 7/62* | (2017.01) |
| *G02B 27/01* | (2006.01) |
| *G06T 11/20* | (2006.01) |
| *H04N 5/272* | (2006.01) |
| *A61B 34/10* | (2016.01) |
| *G06T 7/80* | (2017.01) |
| *G06V 10/60* | (2022.01) |
| *G06V 10/94* | (2022.01) |
| *H04N 23/55* | (2023.01) |
| *H04N 23/60* | (2023.01) |
| *H04N 23/63* | (2023.01) |
| *H04M 1/72403* | (2021.01) |

(52) U.S. Cl.
CPC ............ *H04N 5/272* (2013.01); *H04N 23/55* (2023.01); *H04N 23/635* (2023.01); *H04N 23/64* (2023.01); *A61B 2034/101* (2016.02); *A61B 2034/107* (2016.02); *A61B 2560/0223* (2013.01); *A61B 2560/0233* (2013.01); *A61B 2560/0276* (2013.01); *A61B 2560/0431* (2013.01); *A61B 2560/0487* (2013.01); *G02B 2027/014* (2013.01); *G02B 2027/0138* (2013.01); *G06T 2200/24* (2013.01); *G06T 2207/10016* (2013.01); *G06T 2207/10028* (2013.01); *G06T 2207/10048* (2013.01); *G06T 2207/20212* (2013.01); *G06T 2207/30004* (2013.01); *G06T 2207/30088* (2013.01); *G06T 2207/30244* (2013.01); *G06T 2210/41* (2013.01); *G06V 2201/03* (2022.01); *G06V 2201/034* (2022.01); *H04M 1/72403* (2021.01)

800

810

820

CROSS SECTION VIEWS OF WOUNDS

CROSS-REFERENCE TO RELATED APPLICATIONS

This application is based on and claims the benefit of priority to U.S. patent application Ser. No. 17/646,998 (now allowed), filed Jan. 4, 2022, which is based on and claims the benefit of priority to U.S. Provisional Patent Application No. 63/133,573, filed Jan. 4, 2021, and U.S. Provisional Patent Application No. 63/195,357, filed Jun. 1, 2021, the contents of all of which are incorporated herein by reference in their entireties.

TECHNICAL FIELD

The present disclosure relates generally to the field of image processing for medical purposes. More specifically, the present disclosure relates to systems, methods, and computer-readable media for generating cross section views of a wound.

BACKGROUND

Computer vision may be used in medical testing to determine quantitative and qualitative clinical data. Traditionally, regulatory-approved clinical devices use dedicated hardware such as pre-calibrated scanners that operate in well-known and monitored capturing and illumination conditions, together with classifiers that operate based on the calibrated images derived by the scanners.

In recent years, smartphones have become personal mobile computers with high processing power, wireless Internet access, and high-resolution camera capabilities. However, turning a smartphone into a regulatory-approved clinical device is challenging for at least three main reasons. First, there may be a lack of quality uniformity of the smartphones' cameras. This can occur, for a number of reasons, including the fact that the settings and imaging of each brand and model of smartphone may differ from one to the next. Even within a particular model, there may be slight variations in acquired images. Second, when using smartphones across a host of non-uniformly lit environments, local illumination conditions can lead to varying results. Third, operation of the smartphone by unqualified users that may have difficulties following strict operation procedures.

In health administration, there is often a lack of sufficient resources to effectively meet healthcare demands. For example, hospitals may not have enough medical professionals (e.g., doctors, nurses, etc.) to provide treatment to and administer medical testing for patients. This may result in large inefficiencies, including ineffectively scheduling and prioritizing treatment and testing.

Accordingly, the medical field could benefit greatly from systems that can provide guidance to patients or other unqualified individuals (e.g., through a user interface on a mobile device) to perform treatment and/or testing on their own. Furthermore, it would be highly desired for such systems to make automatic determinations that the patient or unqualified individual should not administer a given treatment and/or testing and instead facilitate the provision of appropriate care by a qualified healthcare professional.

In conventional wound care, physicians, nurses, and other health care professionals often must consult medical records to compare the current condition with previous conditions of the wound in order to make effective evaluations and treatment determinations, which may be time consuming. Moreover, health care professionals must rely on their own evaluation of old photographs, and therefore do not gain the benefit of computer vision capabilities. Accordingly, the field of wound care could greatly benefit from new and improved systems and methods implementing real-time overlays on video feeds of mobile devices would provide great benefits in the field of wound care.

The disclosed embodiments are directed to providing new and improved ways for using personal communications devices for medical testing.

SUMMARY

Embodiments consistent with the present disclosure provide systems, methods, non-transitory computer readable media, and devices for generating cross section views of a wound. Conventionally, medical practitioners have are used to examine cross sections from at least two different orthogonal orientations (for examples, in CT or MR scans). When treating wounds, however, only a frontal view of the wound is available to medical practitioners, given that this is the view from the position of the camera taking the image. This makes wound treatment especially challenging, as the depth of the wound is an important factor in clinical decisions. Currently, the depth of the wound is estimated by eye or measured with a cotton swab, an option which is available only when engaging physically with the wound, but not when examining images of the wound. Therefore, there is a need for systems which provide cross section imaging and depth data using 3D reconstruction of the wound based on data provided by a user through a standard mobile device.

One aspect of the present disclosure is directed to a non-transitory computer readable medium storing data and computer implementable instructions that, when executed by at least one processor, may cause the at least one processor to perform operations for generating cross section views of a wound. The operations may include receiving 3D information of a wound based on information captured using an image sensor associated with an image plane substantially parallel to the wound; generating a cross section view of the wound by analyzing the 3D information; and providing data configured to cause a presentation of the generated cross section view of the wound.

Another aspect of the present disclosure is directed to a system for generating cross section views of a wound. The system may include a memory storing instructions; and at least one processor configured to execute the instructions to receive 3D information of a wound based on information captured using an image sensor associated with an image plane substantially parallel to the wound; generate a cross section view of the wound by analyzing the 3D information; and provide data configured to cause a presentation of the generated cross section view of the wound.

Yet another aspect of the present disclosure is directed to a computer-implemented method for generating cross section views of a wound. The method may include receiving 3D information of a wound based on information captured using an image sensor associated with an image plane substantially parallel to the wound; generating a cross section view of the wound by analyzing the 3D information; and providing data configured to cause a presentation of the generated cross section view of the wound.

In some embodiments, the 3D information of the wound may include at least one of a range image, a stereoscopic image, a volumetric image or a point cloud. In some embodiments, receiving the 3D information of the wound may include one or more of analyzing a video of the wound captured using the image sensor while the image sensor is moving, analyzing a video of the wound depicting a motion of the wound, or analyzing at least one image captured using the image sensor. In some embodiments, the 3D information of the wound may include at least one of a plurality of 2D images of the wound captured from different angles, a stereoscopic image of the wound, an image captured using an active stereo camera, or an image captured using a time-of-flight camera. In some embodiments, generating the cross section view of the wound may include selecting a cross section of the wound from a plurality of cross sections of the wound based on the 3D information; and generating the cross section view of the wound by analyzing the 3D information, the cross section view of the wound corresponding to the selected cross section. In some embodiments, the selected cross section of the wound may correspond to a deepest point of the wound. In some embodiments, generating the cross section view of the wound may include selecting a cross section of the wound from a plurality of cross sections of the wound based on a boundary contour of the wound; and generating the cross section view of the wound by analyzing the 3D information, the cross section view of the wound corresponding to the selected cross section. In some embodiments, the selected cross section of the wound may correspond to one of a longest chord of a shape of the boundary contour or a shortest chord of the shape of the boundary contour. In some embodiments, the selected cross section of the wound may be perpendicular to one or more of a selected chord of a shape of the boundary contour. In some embodiments, generating a cross section view of the wound may include obtaining a segmentation of the wound based on a tissue type; selecting a cross section of the wound of a plurality of cross sections of the wound based on the segmentation of the wound; and generating the cross section view of the wound by analyzing the 3D information, the cross section view of the wound corresponding to the selected cross section. In some embodiments, the generated cross section view of the wound may include one or more of tissue information for at least a portion of the wound, a visual indication of a wound depth, an estimated pre-wound skin contour, or an estimated post-wound skin contour. In some embodiments, the operations may further comprise receiving image data captured using the image sensor; calculating a convolution of a first part of the image data to derive a first result value of the convolution of the first part of the image data; determining a depth of the wound at a first position based on the first result value; calculating a convolution of a second part of the image data to derive a second result value of the convolution of the second part of the image data, the second part of the image data differing from the first part of the image data; and determining a depth of the wound at a second position based on the second result value, the second position differing from the first position. In some embodiments, the generated cross section view of the wound may include a plurality of parallel cross section views of the wound. In some embodiments, the operations may further comprise estimating at least one of an original position of a skin before a formation of the wound or a future position of the skin after healing of the wound by analyzing the 3D information, and the provided data may be based on at least one of the estimated original position of the skin or the future position of the skin. In some embodiments, the provided data may include a depth of the wound estimated based on at least one of the estimated original position of the skin or the estimated future position of the skin. In some embodiments, the generated cross section view of the wound may include a visual indication of at least one of the original position of the skin or the future position of the skin. In some embodiments, at least one of estimating the original position of the skin or estimating the future position of the skin may include implementing an inpainting algorithm based on the 3D information. In some embodiments, the wound may correspond to a first body part of a patient, the patient having a symmetrical body part to the first body part, and at least one of estimating the original position of the skin or estimating the future position of the skin may include receiving 3D information of the symmetrical body part; and analyzing the 3D information of the symmetrical body part and the 3D information of the wound.

Embodiments consistent with the present disclosure provide systems, methods, non-transitory computer readable media, and devices for analyzing wounds using standard equipment. Conventionally, patients suffering from wounds have to physically be attended by a medical practitioner to assess the evolution of their wound. Even if a patient is able to take a picture and send it to their medical practitioner, these pictures lack the quality and consistency to accurately assess the evolution of the wound. This makes wound treatment especially challenging, as a medical practitioner cannot accurately determine the size, color, and shape of a wound based on pictures taken by a standard mobile communications device. Therefore, there is a need for systems which provide medical practitioners with consistent and calibrated images of wounds taken with a standard mobile communications device.

One aspect of the present disclosure is directed to a non-transitory computer readable medium storing data and computer implementable instructions that, when executed by at least one processor, may cause the at least one processor to perform operations for analyzing wounds using standard equipment. The operations may include receiving one or more images of a wound of a patient; analyzing the one or more images to determine, based on at least a difference between values of two pixels of the one or more images, a condition of the wound; selecting an action based on the determined condition of the wound; and initiating the selected action.

In some examples, an indication of a past condition of the wound at a particular time period may be received (the particular time period may be at least one day before the capturing of the one or more images of the wound, and the determination of the condition of the wound may be based on the past condition of the wound and the analysis of the one or more images. In some examples, the selected action may include at least one of processing the one or more images, providing instructions to a user to capture at least one additional image of the wound, or providing particular information associated with the condition of the wound. In some examples, the one or more images may be analyzed to determine at least one of a shape of the wound, a tissue composition of the wound, a depth of the wound, or a presence of an edema in a region surrounding the wound, and wherein the determination of the condition of the wound may be further based on the determined at least one of the shape of the wound, the tissue composition of the wound, the depth of the wound, or the presence of the edema in the region surrounding the wound. In some examples, the one or more images may be and/or include one or more images captured under artificial ultra-violet light. In some examples, the one or more images may be and/or include one or more images captured under artificial infrared light. In some examples, the one or more images may be and/or include one or more images captured using a selected physical optical filter. In some examples, the one or more images may include at least a first image and a second image, the first image may be an image captured using a first physical optical filter and the second image may be an image captured using a second physical optical filter, the second physical optical filter may differ from the first physical optical filter, and the determination of the condition of the wound may be further based on an analysis of the first image and the second image. In some examples, the one or more images may include at least one image depicting at least part of the wound and a calibration element, the calibration element may include a form of a known size, a known shape, or a known color, and the determination of the condition of the wound may be based on at least one of the known size, the known shape, or the known color. In some examples, it may be determined that a confidence level associated with the determined condition of the wound is a first confidence level, and in response to the determination that the confidence level associated with the determined condition of the wound is the first confidence level, initiating the selected action may be avoided.

In some examples, the one or more images of the wound may be and/or include one or more images of the wound captured using a mobile communications device. In one example, the mobile communications device may be caused to provide an instruction to a user of the mobile communications device to capture an image of the wound without a physical optical filter. In one example, the mobile communications device may be caused to provide an instruction to the user to place the physical optical filter. In one example, the mobile communications device may be caused to provide an instruction to the user to capture an image of the wound with the physical optical filter. In one example, the image of the wound captured without the physical optical filter and the image of the wound captured with the physical optical filter may be received. In one example, the image of the wound captured without the physical optical filter and the image of the wound captured with the physical optical filter may be analyzed to determine the condition of the wound. In some examples, the mobile communications device may be caused to provide an instruction to the user to place a calibration element in proximity to the wound (the calibration element may include a form of a known size, a known shape, and a known color), and at least one of the known size, the known shape, or the known color may be used in the analysis of the image of the wound captured without the physical optical filter and the image of the wound captured with the physical optical filter.

In some examples, the one or more images may be analyzed to determine that an urgency level associated with the wound is a first level of urgency. In one example, in response to the determination that the urgency level associated with the wound is the first level of urgency, a particular action may be initiated. For example, the particular action may be configured to cause an advancement of the patient in an order of treatment. In another example, the one or more images may include at least a first image and a second image, the first image being an image captured at least one day before a capturing of the second image, the determination that the urgency level associated with the wound is the first level of urgency may be based on a comparison of the wound in the first image with the wound in the second image, and the particular action may be initiated within one hour of the capturing of the second image.

Another aspect of the present disclosure is directed to a kit for facilitating capturing of medical images. The kit may include a physical optical filter configured to be selectively attached to a standard user mobile communications device and to manipulate light reaching a camera included in the standard user mobile communications device when attached to the standard user mobile communications device; and a calibration element, the calibration element including a form of a known size, a known shape, and a known color.

In some examples, the physical optical filter may be configured to enable capturing of at least two medical images of a wound by the camera included in the standard user mobile communications device, including capturing at least one image using the physical optical filter and capturing at least one image without the physical optical filter, and the calibration element may be configured to enable color calibration of the at least one image captured using the physical optical filter and to enable calibration of the at least one image captured without the physical optical filter. In some examples, the physical optical filter may be shaped to envelop at least one corner of the standard user mobile communications device while covering the camera included in the standard user mobile communications device. In some examples, the physical optical filter may include an adhesive side configured to attach the physical optical filter to the standard user mobile communications device.

Yet another aspect of the present disclosure is directed to a computer-implemented method for analyzing wounds using standard equipment. The method may include receiving one or more images of a wound of a patient; analyzing the one or more images to determine, based on at least a difference between values of two pixels of the one or more images, a condition of the wound; selecting an action based on the determined condition of the wound; and initiating the selected action.

Embodiments consistent with the present disclosure provide systems, methods, non-transitory computer readable media, and devices for generating visual time series of wounds. Conventionally, in each checkup during the treatment of a wound, images of the wound are taken with a mobile device held by a user's hand. The images are taken from different orientations of the camera with respect to the wound, in differing illuminations, and sometimes even with different cameras with different capturing parameters. This makes creating a visual time series view of a wound especially challenging as images of the same wound throughout its treatment may vary greatly and analysis of the wound based on the images may prove flawed because of the images not being normalized. Therefore, there is a need to create a visual time series view of the progression of the wound where the viewing angle, illumination, colors, distance, and other appropriate characteristics of the images are normalized.

One aspect of the present disclosure is directed to a non-transitory computer readable medium storing data and computer implementable instructions that, when executed by at least one processor, may cause the at least one processor to perform operations for generating visual time series of wounds. The operations may include receiving at least a first image data record and a second image data record, the first image data record corresponding to a first point in time and including a first one or more images of a wound captured at the first point in time, and the second image data record corresponding to a second point in time and including a second one or more images of the wound captured at the second point in time; obtaining an image of the wound from a particular point of view corresponding to the first point in time by analyzing the first image data record; generating a simulated image of the wound from the particular point of view corresponding to the second point in time by analyzing the second image data record, wherein the second one or more images of the wound do not include an image of the wound from the particular point of view; and generating a visual time series view of the wound including at least the image of the wound from the particular point of view corresponding to the first point in time and the simulated image of the wound from the particular point of view corresponding to the second point in time.

Another aspect of the present disclosure is directed to a computer-implemented method for generating visual time series views of wounds. The method may include receiving a first image data record and a second image data record, the first image data record corresponding to a first point in time and including a first one or more images of a wound captured at the first point in time, and the second image data record corresponding to a second point in time and including a second one or more images of the wound captured at the second point in time; obtaining an image of the wound from a particular point of view corresponding to the first point in time by analyzing the first image data record; generating a simulated image of the wound from the particular point of view corresponding to the second point in time by analyzing the second image data record, wherein the second one or more images of the wound do not include an image of the wound from the particular point of view; and generating a visual time series view of the wound including at least the image of the wound from the particular point of view corresponding to the first point in time and the simulated image of the wound from the particular point of view corresponding to the second point in time.

Yet another aspect of the present disclosure is directed to a system for generating visual time series of wounds. The system may include a memory storing instructions; and at least one processor configured to execute the instructions to receive at least a first image data record and a second image data record, the first image data record corresponding to a first point in time and including a first one or more images of a wound captured at the first point in time, and the second image data record corresponding to a second point in time and including a second one or more images of the wound captured at the second point in time; obtain an image of the wound from a particular point of view corresponding to the first point in time by analyzing the first image data record; generate a simulated image of the wound from the particular point of view corresponding to the second point in time by analyzing the second image data record, wherein the second one or more images of the wound do not include an image of the wound from the particular point of view; and generate a visual time series view of the wound including at least the image of the wound from the particular point of view corresponding to the first point in time and the simulated image of the wound from the particular point of view corresponding to the second point in time.

In some examples, the image of the wound from the particular point of view corresponding to the first point in time may be a simulated image of the wound based on the first image data record. In some examples, the image of the wound from the particular point of view corresponding to the first point in time may be an image of the first one or more images of the wound. In some examples, the second image data record may include motion data captured using an accelerometer associated with an image sensor used to capture the second one or more images of the wound, and the analyzing the second image data record may include analyzing the motion data. In some examples, generating the simulated image of the wound from the particular point of view corresponding to the second point in time may include generating the simulated image to have selected illumination characteristics. In one example, generating the simulated image of the wound from the particular point of view corresponding to the second point in time may further include analyzing the image of the wound from the particular point of view corresponding to the first point in time to select the selected illumination characteristics. In some examples, the images of the wound from the particular point of view corresponding to the first point in time and to the second point in time may both correspond to a same treatment phase of a treatment cycle of the wound. In one example, generating the simulated image of the wound from the particular point of view corresponding to the second point in time may further include analyzing the image of the wound from the particular point of view corresponding to the first point in time to determine a treatment phase of the treatment cycle of the wound corresponding to the image of the wound from the particular point of view corresponding to the first point in time, and generating the simulated image of the wound from the particular point of view corresponding to the second point in time to correspond to the determined treatment phase. In some examples, each image of the images in the visual time series view of the wound may correspond to a point in time, and the images in the visual time series view of the wound may be ordered based on the corresponding points in time. In some examples, the images of the wound from the particular point of view corresponding to the first point in time and to the second point in time may both correspond to a same distance from the wound. For example, generating the simulated image of the wound from the particular point of view corresponding to the second point in time may include generating the simulated image of the wound from the particular point of view corresponding to the second point in time by causing a distance from the wound in the simulated image to be equal to the distance from the wound associated with the image of the wound from the particular point of view corresponding to the first point in time. In some examples, the images of the wound from the particular point of view corresponding to the first point in time and to the second point in time may both have a same spatial orientation. For example, generating the simulated image of the wound from the particular point of view corresponding to the second point in time may include generating the simulated image of the wound from the particular point of view corresponding to the second point in time by causing a spatial orientation in the simulated image to be equal to a spatial orientation associated with the image of the wound from the particular point of view corresponding to the first point in time. In some examples, pixels of at least one matching pair of pixels of the image of the wound from the particular point of view corresponding to the first point in time and from the simulated image of the wound from the particular point of view corresponding to the second point in time may correspond to a same physical length. In some examples, a convolution of a part of an image of the first one or more images may be calculated to derive a first result value, a convolution of a part of an image of the second one or more images may be calculated to derive a second result value, and a value of at least one pixel of the simulated image of the wound from the particular point of view corresponding to the second point in time may be determined based on the first result value and the second result value. In some examples, a first image of the first one or more images may be analyzed to detect a region of the wound corresponding to a particular tissue type in the first image, a second image of the second one or more images may be analyzed to detect a region of the wound corresponding to the particular tissue type in the second image, and a value of at least one pixel of the simulated image of the wound from the particular point of view corresponding to the second point in time may be determined based on the region of the wound corresponding to the particular tissue type in the first image and the region of the wound corresponding to the particular tissue type in the second image. In some examples, each particular image of the wound from the particular point of view corresponding to the first point in time and to the second point in time may include a visual indicator of a region of the wound corresponding to a particular tissue type in the particular image. In some examples, each particular image of the wound from the particular point of view corresponding to the first point in time and to the second point in time may include a visual indicator of a depth of the wound at a particular location.

Embodiments consistent with the present disclosure provide systems, methods, and computer readable media for rearranging and selecting frames of medical videos. One embodiment consistent with the present disclosure may include a non-transitory computer readable medium storing data and computer implementable instructions that, when executed by at least one processor, cause the at least one processor to perform operations for rearranging and selecting frames of a medical video. The operations may include: obtaining a desired property of a simulated trajectory of a virtual camera; receiving a first video of a wound captured by a moving camera, the first video including a plurality of frames; using the desired property of the simulated trajectory of the virtual camera to analyze the first video to select at least two frames of the plurality of frames corresponding to the simulated trajectory of the virtual camera; using the desired property of the simulated trajectory of the virtual camera to select an order for the selected at least two frames; and rearranging the at least two frames based on the selected order to create a new video of the wound that represents the simulated trajectory of the virtual camera.

According to another embodiment of the present disclosure, a system for rearranging and selecting frames of a medical video may be provided. The system may include a memory storing instructions; and at least one processor configured to execute the instructions to: obtain a desired property of a simulated trajectory of a virtual camera; receive a first video of a wound captured by a moving camera, the first video including a plurality of frames; use the desired property of the simulated trajectory of the virtual camera to analyze the first video to select at least two frames of the plurality of frames corresponding to the simulated trajectory of the virtual camera; use the desired property of the simulated trajectory of the virtual camera to select an order for the selected at least two frames; and rearrange the at least two frames based on the selected order to create a new video of the wound that represents the simulated trajectory of the virtual camera.

According to yet another embodiment of the present disclosure, a computer-implemented method for rearranging and selecting frames of a medical video may be provided. The method may include: obtaining a desired property of a simulated trajectory of a virtual camera; receiving a first video of a wound captured by a moving camera, the first video including a plurality of frames; using the desired property of the simulated trajectory of the virtual camera to analyze the first video to select at least two frames of the plurality of frames corresponding to the simulated trajectory of the virtual camera; using the desired property of the simulated trajectory of the virtual camera to select an order for the selected at least two frames; and rearranging the at least two frames based on the selected order to create a new video of the wound that represents the simulated trajectory of the virtual camera.

In some examples, a trajectory of the moving camera may be a path followed by the moving camera from a first position to a second position, and the simulated trajectory may be a generated path between the first position and the second position. For example, the trajectory of the moving camera may include a diversion rendering at least a portion of the trajectory non-linear, and in one example the simulated trajectory does not include the diversion. In some examples, creating the new video may comprise generating at least one synthetic frame by analyzing the first video, and wherein the new video includes the at least one synthetic frame. In some examples, the simulated trajectory may be selected based on a second video of the wound captured at a different time. For example, data configured to cause a display of the second video may be provided in conjunction with a display of the new video. In some examples, the simulated trajectory may be a standard wound viewing trajectory. In some examples, at least a portion of the simulated trajectory may be selected to be substantially on an arc of a circle, and the wound may be located at or near the center of the circle. In some examples, the desired property of the simulated trajectory of the virtual camera may include. a desired moving direction of the virtual camera. For example, obtaining the desired property of the simulated trajectory may comprise selecting the desired moving direction of the virtual camera based on a contour of the wound. In some examples, the desired property of the simulated trajectory of the virtual camera may include a desired velocity of the virtual camera. In some examples, the desired property of the simulated trajectory of the virtual camera may include a desired distance of the virtual camera from the wound. In some examples, at least one image of the wound may be analyzed to determine a condition of at least part of the wound, and the simulated trajectory of the virtual camera may be determined based on the condition of the at least part of the wound. In some examples, at least one image of the wound may be analyzed to identify a first region of the wound corresponding to a first tissue type and a second region of the wound corresponding to a second tissue type, and the simulated trajectory of the virtual camera may be determined based on a dimension of the first region of the wound, the first tissue type, a dimension of the second region of the wound, and the second tissue type.

In some examples, a first correction factor associated with a first portion of the new video of the wound and a second correction factor associated with a second portion of the new video of the wound may be received. In some examples, creating the new video of the wound may include modifying frames of the first portion of the new video of the wound based on the first correction factor and modifying frames of the second portion of the new video of the wound based on the second correction factor. In one example, the first correction factor may correspond to a first illumination condition and the second correction factor may correspond to a second illumination condition. In one example, the first correction factor may correspond to a first distance from the wound and the second correction factor may correspond to a second distance from the wound. In one example, at least one image of the wound may be analyzed to identify a first region of the wound corresponding to a first tissue type and a second region of the wound corresponding to a second tissue type. The first portion of the new video of the wound may be determined based on the first region of the wound and the second portion of the new video of the wound may be determined based on the second region of the wound. Further, the first correction factor may be determined based on the first tissue type and the second correction factor may be determined based on the second tissue type.

Embodiments consistent with the present disclosure provide systems, methods, and devices for providing guidance for capturing images of wounds. Conventionally, physicians are limited in their ability to accurately analyze a wound's condition and determine appropriate treatment when presented with images of the wound. Even in circumstances where physicians have the opportunity to inspect wounds in person, they are not equipped to perform an analysis of the present wound at the same efficacy as a computerized system configured to analyze a wound if provided with a comparable amount of visual data (e.g., by generating accurate three-dimensional models and/or measurements of the wound and correlating such models with diagnostic data). Accordingly, there is a need for systems and methods for providing guidance for imaging wounds to provide physicians and computerized systems with sufficient data to make effective diagnostic and treatment determinations based on the condition of a patient's wound. Moreover, while a skilled practitioner may know how to capture wound images in a medically beneficial way, image capturing of a wound by medical practitioners limits the capturing to events where the patient and the practitioner meets, such as home visits or clinic visits. However, providing appropriate guidance may enable the patient, or any caregiver of the patient, to capture the wound images at higher frequencies. Through remote medicine, or through automatic analysis of the wound images, the higher frequency of capturing may translate for higher frequency of monitoring. Especially for non-skilled user, providing the guidance in real time when the wound images are captured, and adjusting the guidance to the actions of the user or the status of the wound in real time, may be preferred to offline training that prepares the user to react to different situations.

In one example, consistent with the disclosed embodiments, an example system may: receive a plurality of frames from at least one image sensor associated with a mobile device, at least one of the plurality of frames containing an image of a wound; display, on the mobile device, a real time video including at least a portion of the plurality of frames and a visual overlay indicating a desired position of the wound; detect, based on at least part of the plurality of frames, that the wound is in the desired position; when the wound is in the desired position, display an indication on the mobile device to move the mobile device in a desired direction; receive motion data from at least one motion sensor associated with the mobile device; detect, based on the motion data of the mobile device, that the mobile device has moved in the desired direction; and, when the mobile device has moved in the desired direction, display an additional indication on the mobile device.

In some embodiments, the visual overlay may include an indication of a desired position for a center of the wound. In some embodiments, the visual overlay may include an indication of a bounding shape for the wound in the video. In some embodiments, the operations may further include calculating a convolution of the at least part of the plurality of frames to derive a result value of the calculated convolution; determining an actual position of the wound based on the derived result value of the calculated convolution; and comparing the actual position of the wound with the desired position of the wound to detect that the wound is in the desired position. In some embodiments, the operations may further include detecting, based on an analysis of the at least one frame of the plurality of frames, that the wound is not in the desired position for at least a specified period of time; and when the wound is not in the desired position for at least the specified period of time, displaying, on the mobile device, an indication to correct an actual position of the wound in the video. In some embodiments, the operations may further include before detecting that the wound is in the desired position, displaying, on the mobile device, an indication to correct an actual position of the wound in the video; and after detecting that the wound is in the desired position, halting the display of the indication to correct the actual position of the wound in the video. In some embodiments, the additional indication may include an instruction to move the mobile device in a different direction. In some embodiments, the operations may further include detecting, based on an analysis of the motion data of the mobile device, that the mobile device has moved in a direction different from the desired direction; and when the mobile device has moved in the direction different from the desired direction, displaying an indication on the mobile device to correct the movement of the mobile device. In some embodiments, the operations may further include detecting, based on an analysis of at least one frame of the plurality of frames, that illumination conditions are not satisfactory; and when the illumination conditions are not satisfactory, displaying an indication on the mobile device to take an action to improve the illumination conditions. In some embodiments, the operations may further include generating a user rating based on an analysis of at least one frame of the plurality of frames. In some embodiments, the operations may further include detecting, based on an analysis of at least one frame of the plurality of frames, the presence of a shadow in the plurality of frames; detecting that the shadow is cast over the wound in the plurality of frames; and determining, based on an analysis of the shadow in the plurality of frames, information related to an object casting the shadow. In some embodiments, the operations may further include determining, based on the information, a particular action; and when the shadow is cast over the wound, causing a performance of the particular action. In some embodiments, causing the performance of the particular action may include displaying an indication on the mobile device to move the mobile device to a different location. In some embodiments, the particular action may include activating a flash feature associated with the mobile device. In some embodiments, causing the performance of the particular action may include displaying an indication on the mobile device to move the object casting the shadow so that it no longer casts a shadow on the wound. In some embodiments, the information may include an indication that the object casting the shadow is the mobile device. In some embodiments, the information may include an indication that the object casting the shadow is a hand holding the mobile device. In some embodiments, the operations may further comprise modifying, based on the information and when the shadow is cast over the wound, at least one parameter associated with the at least one image sensor.

Embodiments consistent with the present disclosure provide systems, methods, and devices for providing wound capturing guidance. In one example, consistent with the disclosed embodiments, an example system may: display, on a mobile device, a user interface configured to guide a patient through one or more steps for performing a medical action, the plurality of steps including at least: using at least one item of a medical kit; and capturing at least one image of at least part of the at least one item of the medical kit using at least one image sensor associated with the mobile device. The example system may also: detect a failure to successfully complete the medical action; select from one or more alternative reactions, a reaction to the detected failure likely to bring a successful completion of the medical action; and provide instructions associated with the selected reaction.

In some embodiments, the one or more alternative reactions may include at least two of triggering a provision of an additional medical kit to the patient; triggering an approach to the patient by a person; or triggering a provision of additional guidance to the patient using the user interface. In some embodiments, the selected reaction may include triggering a provision of an additional medical kit to the patient, and the provided instructions may be configured to cause the provision of the additional medical kit to the patient. In some embodiments, the selected reaction may include triggering an approach to the patient by a person, and the provided instructions may be configured to alert the person to approach the patient. In some embodiments, the selected reaction may include triggering a provision of additional guidance to the patient, and the provided instructions may be configured to provide additional guidance to the patient using the user interface. In some embodiments, the selection of the reaction may be based on a type of the failure detected. In some embodiments, the selection of the reaction may be based on a result of the detected failure. In some embodiments, detecting a failure may include identifying the one or more failed steps for performing a medical action and selecting a reaction is based on the one or more failed steps identified. In some embodiments, the steps for performing a medical action may further include at least one of positioning a calibrator sticker; positioning a dipstick adjacent to a calibrator; dipping a dipstick in a medical sample; or blotting a dipstick. In some embodiments, detecting a failure may further include at least one of detecting that the calibrator sticker is incorrectly positioned, the dipstick is incorrectly positioned adjacent to the calibrator, the dipstick is improperly dipped in the medical sample, or the dipstick is improperly blotted. In some embodiments, the at least one item of the medical kit may be at least one of a dipstick; or a calibrator. In some embodiments, the detected failure may include a failure to perform a physical action using the at least one item of the medical kit. In some embodiments, the detected failure may include a failure to capture the at least one image within a particular time window. In some embodiments, detecting the failure may be based on an analysis of the at least one captured image. In some embodiments, detecting the failure may include detecting that the user interface was shut down before completing at least one of the steps for performing a medical action. In some embodiments, the operations may further include determining that the failure necessitates a usage of an alternative item to the at least one item of the medical kit for a successful completion of the medical action; when the medical kit includes the alternative item, the selected reaction includes at least one of triggering an approach to the patient by a person or triggering a provision of additional guidance to the patient using the user interface; and when the medical kit does not include the alternative item, the selected reaction includes at least one of triggering a provision of an additional medical kit to the patient or triggering a performance of the medical action by a medical professional. In some embodiments, the operations may further include determining that the failure necessitates a usage of an alternative item to the at least one item of the medical kit for a successful completion of the medical action; determining that the patient has a first characteristic; in response to the patient having the first characteristic, triggering a provision of an additional medical kit to the patient; determining that the patient has a second characteristic; and in response to the patient having the second characteristic, triggering a performance of the medical action by a medical professional. In some embodiments, the operations may further include determining that the failure does not necessitate a usage of an alternative item to the at least one item of the medical kit for a successful completion of the medical action; determining that the patient has a first characteristic; in response to the patient having the first characteristic, triggering an approach to the patient by a person; determining that the patient has a second characteristic; and in response to the patient having the second characteristic, triggering a provision of additional guidance to the patient using the user interface.

Embodiments consistent with the present disclosure provide systems, methods, and devices for displaying an overlay on wounds. In one example, consistent with the disclosed embodiments, an example method or system may: receive a real time video feed; receive image-based information associated with at least one previously captured image of a wound; generate, using the video feed and the image-based information, an overlay including an indication of a condition of the wound in the at least one previously captured image; and display, on at least one user interface, the overlay, wherein the at least one user interface is configured to display the overlay in a position associated with a position of the wound in the video feed.

In some examples, the at least one previously captured image may be captured at least one day before the video feed is captured. In some examples, the video feed may include a plurality of wounds, and the wound may be selected from the plurality of wounds. In some examples, the overlay may be displayed on the user interface feed in real time. In some examples, the indication of the condition of the wound may include a visual indication of a contour of the wound in the at least one previously captured image. In some examples, the indication of the condition of the wound may include an indication of at least one measurement of the wound in the at least one previously captured image (for example, the at least one measurement may include at least one of a length, an area, a volume, or a depth of the wound). In some examples, the indication of the condition of the wound may include a visual indication of a segment of the wound in the at least one previously captured image corresponding to a tissue type. In some examples, the indication of the condition of the wound may include a visual indication of a color of a portion of the wound in the at least one previously captured image. In some examples, the indication of the condition of the wound may include a visual indication of a severity of the wound in the at least one previously captured image.

In some examples, receiving the image-based information may comprise accessing a plurality of records, each record of the plurality of records corresponding to a different wound, selecting a record corresponding to the wound of the plurality of records based on the video feed, and obtaining the image-based information from the selected record.

In some examples, the overlay may be displayed in real time using a transparent optical system included in a wearable device, the real time video feed may be a real time video feed captured using an image sensor included in the wearable device, the wound may be visible to a user wearing the wearable device through the transparent optical system, and the display of the overlay may be configured to make the overlay appear to the user wearing the wearable device at least partly over the wound.

In some examples, the at least one user interface may be associated with a mobile device. For example, the at least one user interface may be configured to automatically adjust the position of the displayed overlay based on detected movement of the mobile device.

In some examples, second image-based information associated with a second at least one previously captured image of the wound may be received. Further, a second indication may be included in the overlay. The second indication may be an indication of a condition of the wound in the second at least one previously captured image. The condition of the wound in the second at least one previously captured image may differ from the condition of the wound in the at least one previously captured image. In one example, the overlay may further include an indication of a capturing time associated with the at least one previously captured image and an indication of a capturing time associated with the second at least one previously captured image. In another example, the condition of the wound in the at least one previously captured image may correspond to a first point in time, and the condition of the wound in the second at least one previously captured image may correspond to a second point in time. Further, the image-based information and the second image-based information may be used to determine a condition of the wound corresponding to a third point in time (the third point in time may differ from the first point in time and the second point in time), and a third indication may be included in the overlay. The third indication may be an indication of a condition of the wound corresponding to the third point in time.

In some examples, a convolution of at least part of the at least one previously captured image may be calculated to derive a result value. In response to a first result value, a first indication of the condition of the wound in the at least one previously captured image may be included in the overlay, and in response to a second result value, a second indication of the condition of the wound in the at least one previously captured image may be included in the overlay. The second indication may differ from the first indication.

Embodiments may include a display, on a mobile device, and a user interface configured to guide a patient through a plurality of steps for performing a medical action, the plurality of steps including at least: using at least one item of a medical kit; and capturing at least one image of at least part of the at least one item of the medical kit using at least one image sensor associated with the mobile device. The example system may also: detect a failure to successfully complete the medical action; select from a plurality of alternative reactions, a reaction to the detected failure likely to bring a successful completion of the medical action; and provide instructions associated with the selected reaction.

In some embodiments, the at least one previously captured image may be captured at least one day before the video feed is captured. In some embodiments, the video feed may include a plurality of wounds, and the operations may further include selecting the wound from the plurality of wounds. In some embodiments, receiving the image-based information may include accessing a plurality of records, each record of the plurality of records corresponding to a different wound; selecting a record corresponding to the wound of the plurality of records based on the video feed; and obtaining the image-based information from the selected record. In some embodiments, the overlay may be displayed on the user interface feed in real time. In some embodiments, the overlay may be displayed in real time using a transparent optical system included in a wearable device, the real time video feed being a real time video feed captured using an image sensor included in the wearable device, the wound being visible to a user wearing the wearable device through the transparent optical system, and the display of the overlay being configured to make the overlay appear to the user wearing the wearable device at least partly over the wound. In some embodiments, the at least one user interface may be associated with a mobile device. In some embodiments, the at least one user interface may be configured to automatically adjust the position of the displayed overlay based on detected movement of the mobile device. In some embodiments, the operations may further include receiving second image-based information associated with a second at least one previously captured image of the wound; and including a second indication in the overlay, the second indication being an indication of a condition of the wound in the second at least one previously captured image, the condition of the wound in the second at least one previously captured image differing from the condition of the wound in the at least one previously captured image. In some embodiments, the overlay may further an indication of a capturing time associated with the at least one previously captured image and an indication of a capturing time associated with the second at least one previously captured image. In some embodiments, the condition of the wound in the at least one previously captured image may correspond to a first point in time, the condition of the wound in the second at least one previously captured image may correspond to a second point in time, and the operations may further include using the image-based information and the second image-based information to determine a condition of the wound corresponding to a third point in time, the third point in time differing from the first point in time and the second point in time; and including a third indication in the overlay, the third indication being an indication of a condition of the wound corresponding to the third point in time. In some embodiments, the operations may further include calculating a convolution of at least part of the at least one previously captured image to derive a result value; in response to a first result value, including in the overlay a first indication of the condition of the wound in the at least one previously captured image; and in response to a second result value, including in the overlay a second indication of the condition of the wound in the at least one previously captured image, the second indication differing from the first indication. In some embodiments, the indication of the condition of the wound may include a visual indication of a contour of the wound in the at least one previously captured image. In some embodiments, the indication of the condition of the wound may include an indication of at least one measurement of the wound in the at least one previously captured image. In some embodiments, the at least one measurement may include at least one of a length, an area, a volume, or a depth of the wound. In some embodiments, the indication of the condition of the wound may include a visual indication of a segment of the wound in the at least one previously captured image corresponding to a tissue type. In some embodiments, the indication of the condition of the wound may include a visual indication of a color of a portion of the wound in the at least one previously captured image. In some embodiments, the indication of the condition of the wound may include a visual indication of a severity of the wound in the at least one previously captured image.

Consistent with other disclosed embodiments, non-transitory computer-readable storage media may store program instructions, which are executed by at least one processing device, and may perform any of the methods described herein.

The foregoing general description and the following detailed description are for example and explanatory only and are not restrictive of the claims.

DETAILED DESCRIPTION

Figure 1A:
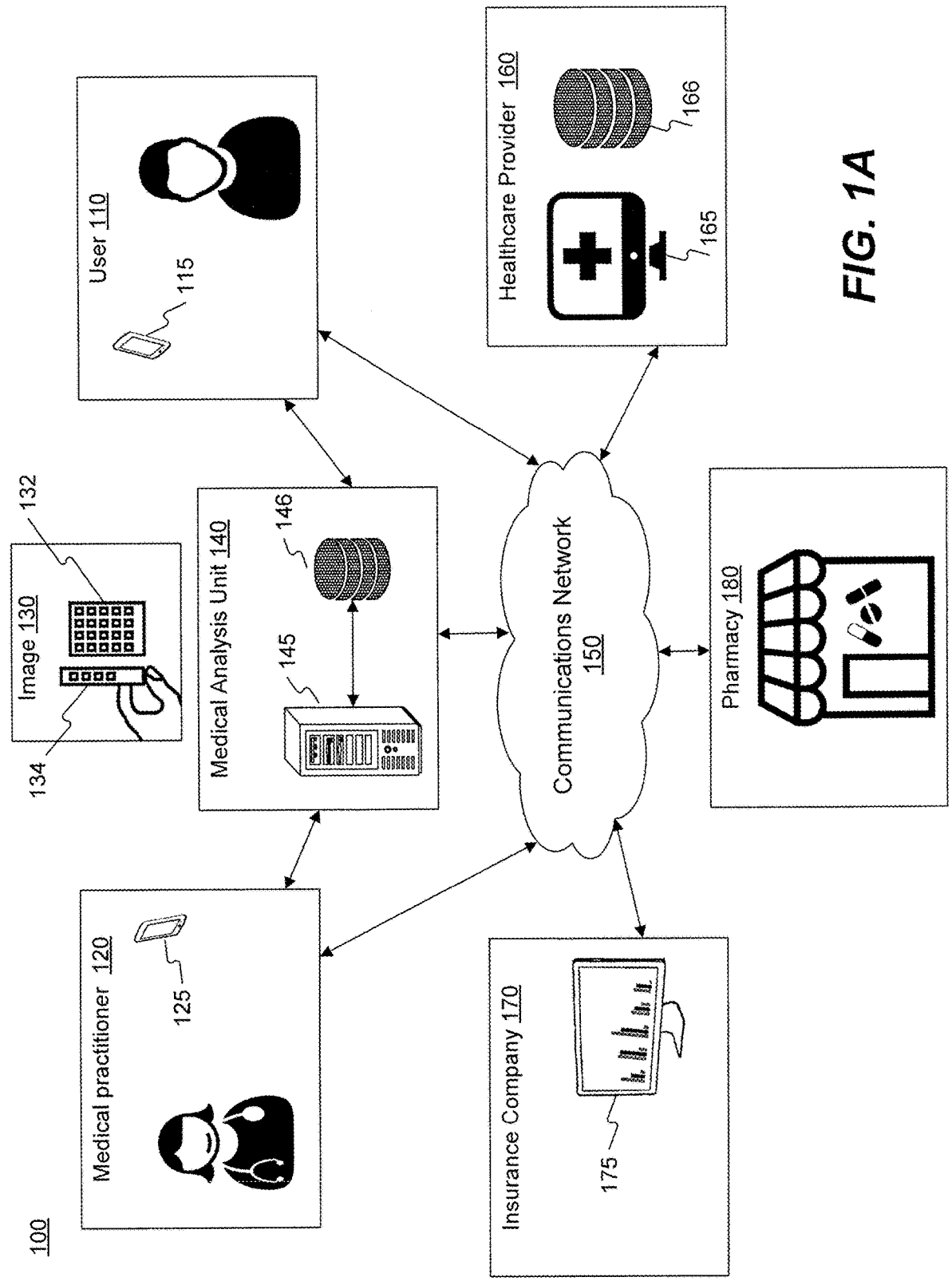
FIG. 1A is a schematic illustration of an example system that uses image data captured by mobile communications devices for medical testing, consistent with some embodiments of the present disclosure.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions, or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples, but is inclusive of general principles described herein in addition to the general principles encompassed by the appended claims.

The present disclosure is directed to systems and methods for processing images captured by an image sensor. As used herein, the term "image sensor" refers to any device capable of detecting and converting optical signals in the near-infrared, infrared, visible, and ultraviolet spectrums into electrical signals. Examples of image sensors may include digital cameras, phone cameras, semiconductor charge-coupled devices (CCD), active pixel sensors in complementary metal-oxide-semiconductor (CMOS), or N-type metal-oxide-semiconductor (NMOS, Live MOS). The electrical signals may be used to generate image data. Consistent with the present disclosure, the image data may include pixel data streams, digital images, digital video streams, data derived from captured images, and data that may be used to construct a 3D image. The image data acquired by the image sensor may be transmitted by wired or wireless transmission to a remote server.

Consistent with the present disclosure, the image sensor may be part of a camera included in a mobile communications device. The term "mobile communications device" refers to any portable device with image capturing capabilities that can communicate with a remote server over a wireless network. Examples of mobile communications devices include, smartphones, tablets, smartwatches, smart glasses, wearable sensors and other wearable devices, wireless communication chipsets, user equipment (UE), personal digital assistants, and any other portable pieces of communications equipment. It is noted that the terms "handheld mobile communications device," "handheld mobile device," "mobile communications device," and "mobile device" may be used interchangeably herein and may refer to any of the variety of devices listed above.

Embodiments of the present disclosure further include analyzing images to identify a colorized surface in proximity to a medical analysis region. As used herein, the term "colorized surface" may broadly refer to any surface having planar or nonplanar properties. The colorized surface may cover or encapsulate at least a portion of a 2D object (such as a sheet of paper) or at least a portion of a 3D object (such as a box or a body part). The colorized surface may include a plurality of reference elements for enabling light and color calibration. In some embodiments, the colorized surface may be printed on a sticker or a plaster (e.g., adhesive bandage), for example, the colorized surface illustrated in FIG. 4A. In other embodiments, the colorized surface may be printed or otherwise presented on a board, cardstock, plastic or any other medium adapted to serve as a reference. The colorized surface may be incorporated into the packaging of a test kit, for example. One non-limiting example of a colorized surface is illustrated in FIG. 4B. The image correction enabled by the colorized surface may be used to enable a color correction of an image of an object depicted in the medical analysis region. As used herein, the term "medical analysis region" may be an area on or near the surface distinct from the colorized portion of the surface used for color correction where an object for examination may be placed. The medical analysis region may be of uniform color or varied color so long as other portions of the colorized surface may be used as references for color correction. In a preferred embodiment, the colorized surface may include an un-colorized or uniformly colorized region demarcated for object placement. Such a distinct region may be larger than the object to be received thereon. In other embodiments, the medical analysis region may not be demarcated, permitting the user to independently select a location of object placement, so long as enough of the colorized surface remains unblocked for reference purposes during image analysis.

In some embodiments, the examined object is a skin or other tissue or anatomical feature, and the medical analysis region may include any part of the patient's body depicted in the image. In another embodiment, the examined object may be a dipstick, and the color of the medical analysis region may be significantly darker or lighter than a majority of the colorized surface. For example, the medical analysis region may be at least 50% darker than the colorized surface. It is noted that the terms "medical analysis region," "dipstick placement region," and "test region," may be used interchangeably herein to refer to the same area.

Consistent with the present disclosure, the colorized surface may enable processing of the image to determine the colors of the examined object, irrespective of local illumination conditions. The term "irrespective of local illumination conditions" refers to the output of an image analysis process in which the suggested system rectifies the colors of the examined object to remove at least some effects of local illumination. Effects of local illumination conditions to be removed, may include one or more of reflections, shades, light temperature (e.g., soft white, cool white, daylight), and any other condition that may impact the detection of object color. Additionally, the colorized surface may also enable processing of the image to determine the colors of the examined object, irrespective of specific image capturing effects associated with the image capturing device. Examples of the different effects associated with the image capturing process that may be removed are described below.

In some embodiments, an image correction factor may be generated based on the determined local illumination conditions and/or image capturing parameters. The image correction factor may be used to remove one or more local illumination variations and to determine illumination invariant colors of the examined object. The image correction factor may be used to remove image capturing process effects to determine capturing process invariant colors of the examined object. In one example, the invariant colors may be used to determine an extent of a chemical reaction on a reagent pad. In another example, the invariant colors may be used to determine a skin condition, such as a condition of a wound. In yet another example, the invariant colors may be used to determine a condition of a tissue, such as skin, oral mucosa, nasal mucosa, and so forth. In an additional example, the invariant colors may be used to determine properties of biological material, such as a stool sample, a urine sample, a phlegm sample, a blood sample, a wax sample, and so forth.

The term "confidence level" refers to any indication, numeric or otherwise, of a level (e.g., within a predetermined range) indicative of an amount of confidence the system has that the determined colors of the examined object are the colors of the examined object irrespective of local illumination conditions and/or image capturing settings effects. For example, the confidence level may have a value between 1 and 10. Alternatively, the confidence level may be expressed as a percentage or any other numerical or non-numerical indication. In some cases, the system may compare the confidence level to a threshold. The term "threshold" as used herein denotes a reference value, a level, a point, or a range of values. In operation, when a confidence level of a measurement exceeds a threshold (or below it depending on a particular use case), the system may follow a first course of action and, when the confidence level is below it (or above it depending on a particular use case), the system may follow a second course of action. The value of the threshold may be predetermined for each type of examined object or may be dynamically selected based on different considerations.

Reference is now made to FIG. 1A, which shows an example of a system 100 that uses image analysis to complete a medical examination. System 100 may be computer-based and may include computer system components, desktop computers, workstations, tablets, handheld computing devices, memory devices, and/or internal network(s) connecting the components. System 100 may include or be connected to various network computing resources (e.g., servers, routers, switches, network connections, storage devices, etc.) for supporting services provided by system 100.

Consistent with the present disclosure, system 100 may enable user 110 to complete a medical examination. In addition, system 100 may enable a medical practitioner 120 to participate in the medical examination using a mobile communications device 125. The disclosure below that describes the functionalities of mobile communications device 115 similarly describes the functionalities of mobile communications device 125. In one embodiment, medical practitioner 120 may be a nurse that captures images of an object associated with user 110. In another embodiment, medical practitioner 120 may be a physician of user 110 who receives the test results of the medical examination. In the example illustrated in FIG. 1A, user 110 may use mobile communications device 115 to capture an image 130 that includes a colorized surface 132 and an object to be examined 134. Image data associated with image 130 may be transmitted to a medical analysis unit 140 for medical testing (directly or via a communication network). Medical analysis unit 140 may include a server 145 coupled to one or more physical or virtual storage devices such as a data structure 146. System 100 may also include or be connected to a communications network 150 that facilitates communications and data exchange between different system components and the different entities associated with system 100, such as, healthcare provider 160, insurance company 170, and pharmacy 180.

According to embodiments of the present disclosure, medical analysis unit 140 may exchange data with a variety of communication devices associated with the different entities associated with system 100. The term "communication device" is intended to include all possible types of devices capable of exchanging data using communications network 150. In some examples, the communication device may include a smartphone, a tablet, a mobile station, a personal digital assistant, a desktop, a laptop, an IoT device, a dedicated terminal, a server, a cloud, and any other device that enables data communications. In one implementation, medical analysis unit 140 may receive image data from mobile communications device 115, and cause mobile communications device 115 to provide user 110 with data derived from analysis of examined object 134. In another implementation, medical analysis unit 140 may transmit data to a communications device 165 of healthcare provider 160 for updating an electronic medical record (EMR) of user 110 stored in data structure 166. In another implementation, medical analysis unit 140 may receive information from a communications device 175 of insurance company 170. The received information may identify a group of individuals associated with a first insurance status. Thereafter, medical analysis unit 140 may initiate medical examinations to determine if there is a likelihood that the group of individuals is entitled to a second insurance status different from the first insurance status. In yet another implementation, medical analysis unit 140 may transmit a medicine prescription to pharmacy 180 for treating user 110 based on the test result derived from image data captured by mobile communications device 115.

Embodiments of the present disclosure may include accessing or otherwise utilize one or more data structures, such as a database. As used herein the term "data structure" may include any collection of data values and relationships among them. The data may be stored linearly, horizontally, hierarchically, relationally, non-relationally, uni-dimensionally, multidimensionally, operationally, in an ordered manner, in an unordered manner, in an object-oriented manner, in a centralized manner, in a decentralized manner, in a distributed manner, in a custom manner, or in any manner enabling data access. By way of non-limiting examples, data structures may include an array, an associative array, a linked list, a binary tree, a balanced tree, a heap, a stack, a queue, a set, a hash table, a record, a tagged union, ER model, and a graph. For example, a data structure may include an XML datastructure, an RDBMS datastructure, an SQL data structure or NoSQL alternatives for data storage/search such as, for example, MongoDB, Redis, Couchbase, Datastax Enterprise Graph, Elastic Search, Splunk, Solr, Cassandra, Amazon DynamoDB, Scylla, HBase, SharePoint, Sybase, Oracle and Neo4J. Data structures, where suitable, may also include document management systems. A data structure may be a component of the disclosed system or a remote computing component (e.g., a cloud-based data structure). Data in the data structure may be stored in contiguous or non-contiguous memory. Moreover, a data structure, as used herein, does not require information to be co-located. It may be distributed across multiple servers, for example, that may be owned or operated by the same or different entities. Thus, the term "data structure" as used herein in the singular is inclusive of plural data structures.

Consistent with the present disclosure, server 145 may access data structure 146 to determine, for example, specific chromatic properties associated with colorized surface 132 at the time of printing of the colorized surface 132. Data structures 146 and data structure 166 may utilize a volatile or non-volatile, magnetic, semiconductor, tape, optical, removable, non-removable, other type of storage device or tangible or non-transitory computer-readable medium, or any medium or mechanism for storing information. Data structure 146 (and data structure 166 mutatis mutandis) may be part of server 145 or separate from server 145 as shown. When data structure 146 is not part of server 145, server 145 may exchange data with data structure 146 via a communication link. Data structure 146 may include one or more memory devices that store data and instructions used to perform one or more features of the disclosed embodiments. In one embodiment, data structure 146 may include a plurality of suitable data structures, ranging from small data structures hosted on a workstation to large data structures distributed among data centers. Data structure 146 may also include any combination of one or more data structures controlled by memory controller devices (e.g., server(s), etc.) or software.

Consistent with the present disclosure, communications network 150 may be any type of network (including infrastructure) that supports communications, exchanges information, and/or facilitates the exchange of information between the components of system 100. For example, communications network 150 may include or be part of the Internet, a Local Area Network, wireless network (e.g., a Wi-Fi/302.11 network), or other suitable connections. In other embodiments, one or more components of system 100 may communicate directly through dedicated communication links, such as, for example, a telephone network, an extranet, an intranet, the Internet, satellite communications, off-line communications, wireless communications, transponder communications, a local area network (LAN), a wide area network (WAN), a virtual private network (VPN), or any other mechanism or combinations of mechanisms that enable data transmission.

The components and arrangements of system 100 shown in FIG. 1A are intended to provide examples and are not intended to limit the disclosed embodiments, as the system components used to implement the disclosed processes and features may vary.

Figure 1B:
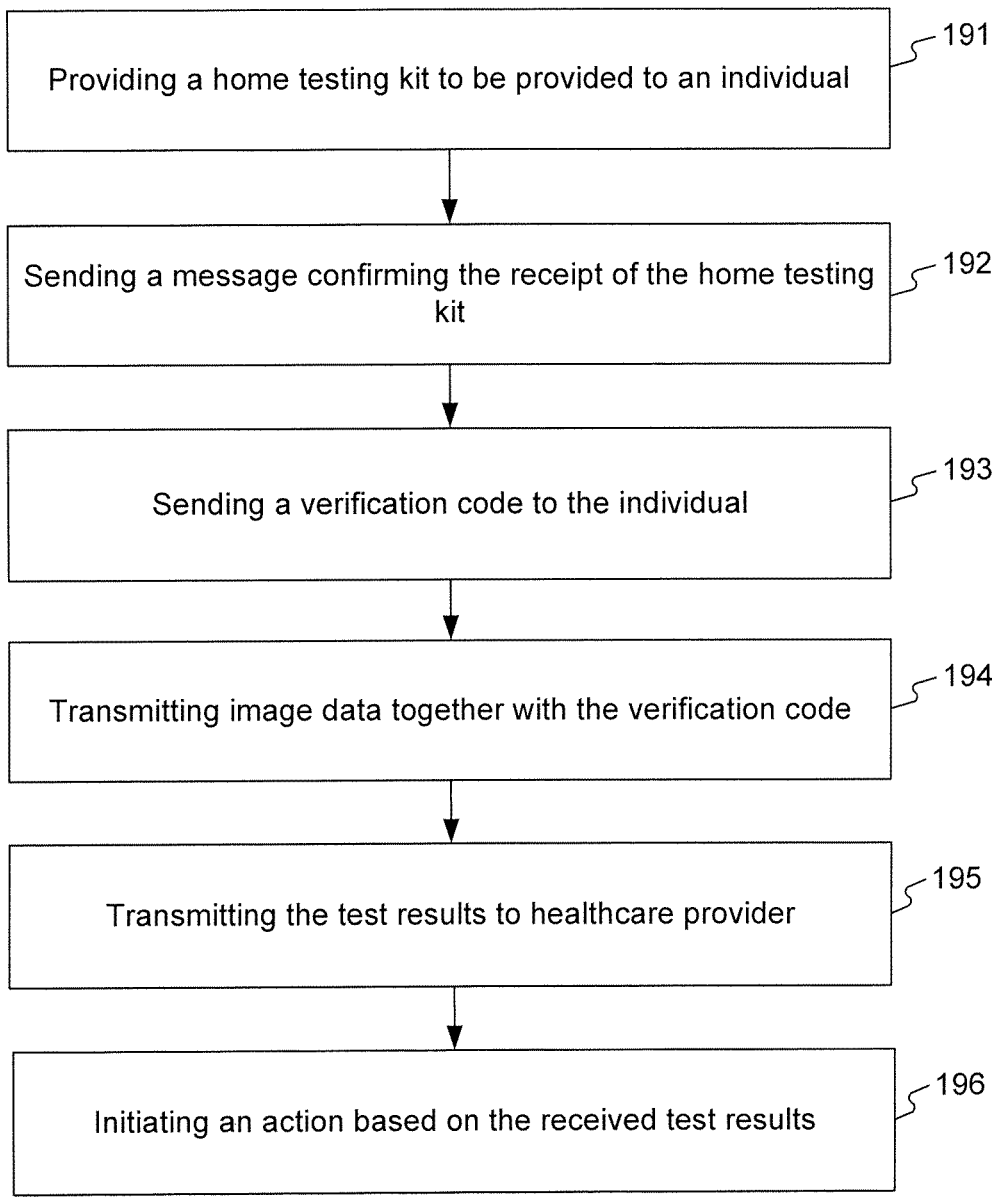
FIG. 1B is a flowchart of an example process for completing a medical examination, consistent with some embodiments the present disclosure.
Figure 1C:
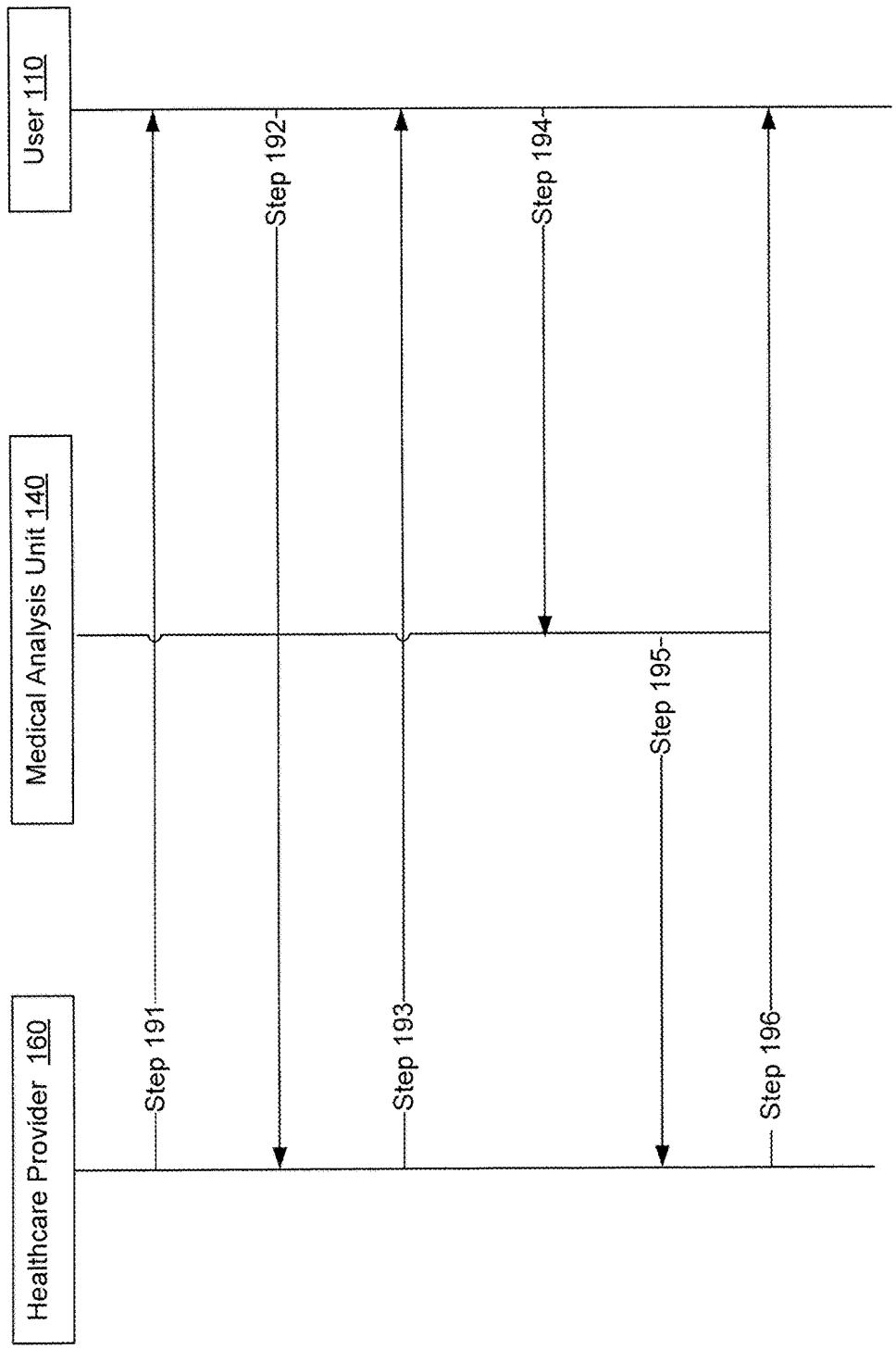
FIG. 1C is an example flow diagram illustrating communications exchanges between different entities implementing the process of FIG. 1B, consistent with some embodiments of the present disclosure.

FIG. 1B is a flowchart of an example process for completing a medical examination according to embodiments of the present disclosure. In some embodiments, the example process is executed by different components of system 100. For example, healthcare provider 160, medical analysis unit 140, and user 110. In one embodiment, any action performed by server 145 may be performed by any combination of mobile communications device 115, mobile communications device 125, communications device 165, and communications device 175. FIG. 1C illustrates how the example process is implemented by healthcare provider 160, medical analysis unit 140, and user's mobile communications device 115.

Example process 190 starts when healthcare provider 160 causes a home testing kit to be physically provided to user 110 (step 191). Consistent with the present disclosure, causing the home testing kit to be physically provided to user 110 may include shipping the test kit to user 110, sending an instruction to a third party to ship a test kit to user 110, physically providing user 110 with a test kit, or conveying a test to user 110 in any other way. For example, shipping instructions may be generated, a pick up order may be placed with a shipping company, or the testing kit may be deposited for pickup by a courier. In some cases, healthcare provider 160 may cause home testing kits to be delivered to a group of individuals identified through information from insurance company 170. In other cases, healthcare provider 160 may cause home testing kits to be delivered to user 110 in response to a request from medical practitioner 120 or as the result of a request from user 110. Alternatively, healthcare provider 160 may automatically cause home testing kits to be delivered to user 110 based on information about user 110 stored in data structure 166. In one example, a physician may have previously prescribed annual testing for user 110, or user 110 might have met some triggering time-based criteria or health-based criteria that triggers an indication that user 110 should receive the test kit. In another example, an operator (such as a healthcare provider 160, insurance company 170, etc.) may conduct a query on data structure 166 to identify users that meet the selected criteria, and may cause delivery of home testing kits to at least some of the identified users.

Process 190 may continue when user 110 sends a message confirming the receipt of the home testing kit (step 192). In some embodiments, user 110 may send the message directly to healthcare provider 160. In other embodiments, user 110 may send the message using a dedicated application associated with medical analysis unit 140, and the message may be conveyed to healthcare provider 160. The message may be text or voice based, or may occur as a button pushed or box checked in response to a prompt on a user interface. Alternatively, the message may simply be the scanning or entry of a code. Thereafter, healthcare provider 160 may send a verification code to user 110 (step 193). According to one embodiment, the verification code may be sent in a text message directly to user 110 after receiving the confirmation message, or may be provided through a user interface of an application accessed via a device of user 110. As an alternative to an exchange of electronic messages in order to obtain the verification code, the verification code may be physically provided with the home testing kit in step 191. In such an example, step 192 and step 193 may be excluded from process 190.

Process 190 may continue when user 110 follows instructions associated with the specific medical examination, uses mobile communications device 115 to capture image 130, and transmits image data together with (or in a manner that causes it to be associated with) the verification code to medical analysis unit 140 (step 194). The image data transmitted to image analysis unit 140 may include image 130, a cropped image with examined object 134, a processed version of image 130 (e.g., one where the color of at least part of the pixels of image 130 was corrected based on colorized surface 132), or data derived from image 130. In one aspect of the disclosure, examined object 134 may be a skin feature. According to another aspect of the disclosure, examined object 134 may include a reagent, such as a dipstick with one or more reagent pads.

Process 190 may continue when medical analysis unit 140 determines test results associated with a state of examined object 134, possibly taking into account local illumination conditions and/or image capturing settings effects. In other words, medical analysis unit 140 may inspect the image of examined object 134 after the effects of the local illumination conditions and/or of the effects of the image capturing settings are removed. In another example, medical analysis unit 140 may inspect the image of examined object 134 with a function that takes into account local illumination conditions and/or image capturing settings effects. When examined object 134 is a dipstick, determining its state may include determining an extent of a chemical reaction on a least one reagent pad of the dipstick. When examined object 134 is a skin feature, determining the object's state may include determining its condition, including, for example, comparing the object's state relative to a previous record of the skin feature. In one example, when the skin feature is a wound, medical analysis unit 140 may determine from the image data a healing progress of the wound. In another example, when the skin feature is a mole, medical analysis unit 140 may determine from the image data the likelihood that the mole changed in size or that it has an increased risk of being cancerous. Thereafter, medical analysis unit 140 may transmit the test results to healthcare provider 160 (step 195), and/or to other entities (such as user 110, medical practitioner 120, insurance company 170, pharmacy 180, and so forth).

Process 190 may continue when healthcare provider 160 initiates an action based on the received test results. In one embodiment, initiating an action based on the received test results may include presenting the test results to medical practitioner 120 (e.g., the user's physician). In another embodiment, initiating an action based on the received test results may include updating an electronic medical record (EMR) of user 110. In another embodiment, initiating an action based on the received test results may include generating a prescription and automatically (or semi-automatically) forwarding it to pharmacy 180. In another embodiment, initiating an action based on the received test results may include sending medical information to user 110 (step 196) or permitting medical analysis unit 140 to send medical information to user 110. The medical information transmitted to user 110 may include the test results, an invitation to schedule an appointment, a prescription, an indication that the user may be eligible for a different insurance coverage, or any other action that results from the test.

FIG. 1C is a message flow diagram illustrating communications exchanges between different entities implementing the process of FIG. 1B, consistent with some embodiments of the present disclosure. It is to be understood that the process may be modified consistent with embodiments disclosed herein.

Figure 2:
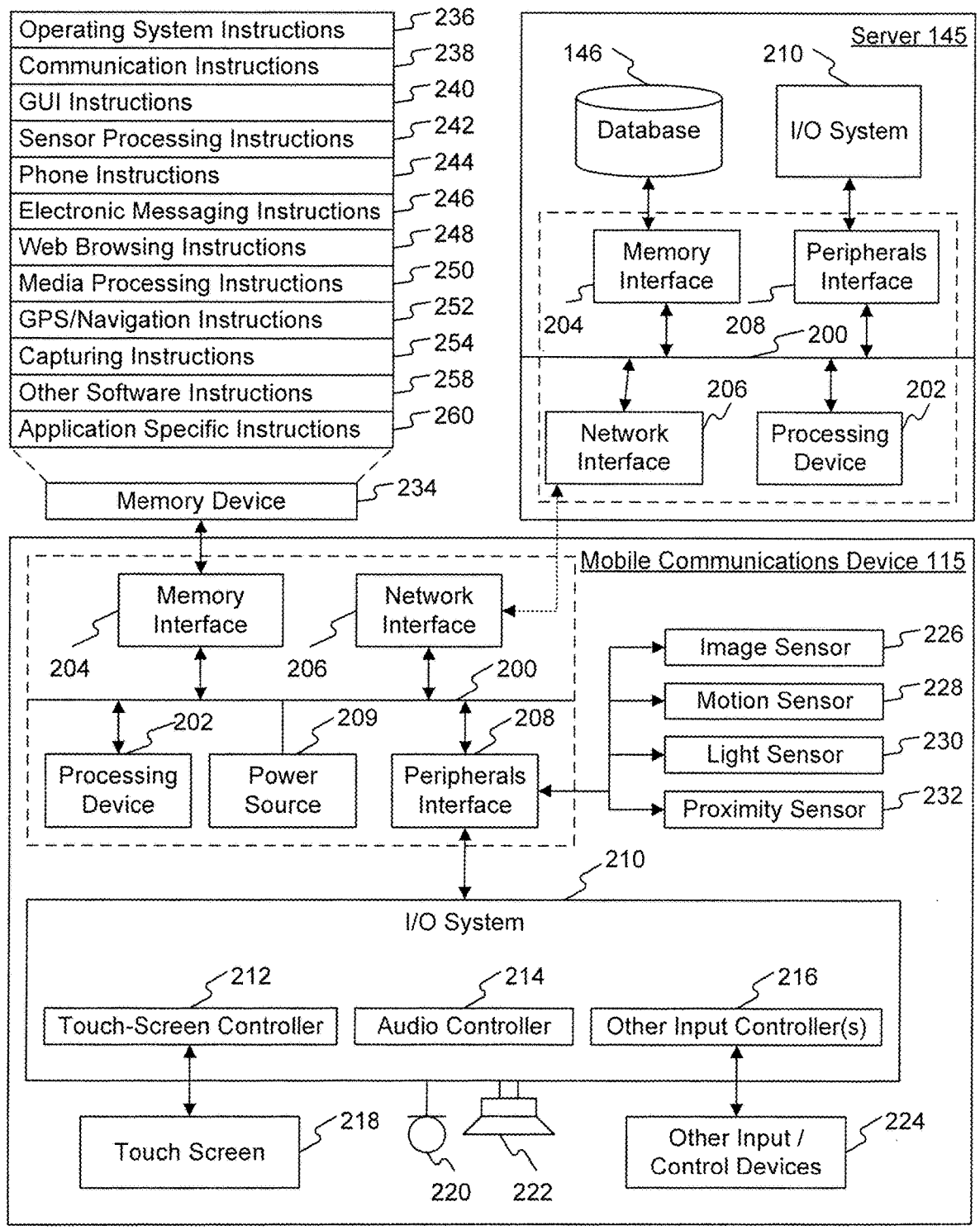
FIG. 2 is a block diagram illustrating some of the components of the system of FIG. 1A, consistent with some embodiments of the present disclosure.

FIG. 2 is an example block diagram of configurations of server 145 and mobile communications device 115. In one embodiment, server 145 and mobile communications device 115 directly or indirectly accesses a bus 200 (or other communication mechanism) that interconnects subsystems and components for transferring information within server 145 and/or mobile communications device 115. For example, bus 200 may interconnect a processing device 202, a memory interface 204, a network interface 206, a peripherals interface 208 connected to I/O system 210, and power source 209.

Processing device 202, shown in FIG. 2, may include at least one processor configured to execute computer programs, applications, methods, processes, or other software to perform embodiments described in the present disclosure. For example, the processing device may include one or more integrated circuits, microchips, microcontrollers, microprocessors, all or part of a central processing unit (CPU), graphics processing unit (GPU), digital signal processor (DSP), field programmable gate array (FPGA), or other circuits suitable for executing instructions or performing logic operations. The processing device may include at least one processor configured to perform functions of the disclosed methods such as a microprocessor. The processing device may include a single core or multiple core processors executing parallel processes simultaneously. In one example, the processing device may be a single core processor configured with virtual processing technologies. The processing device may implement virtual machine technologies or other technologies to provide the ability to execute, control, run, manipulate, store, etc., multiple software processes, applications, programs, etc. In another example, the processing device may include a multiple-core processor arrangement (e.g., dual, quad core, etc.) configured to provide parallel processing functionalities to allow a device associated with the processing device to execute multiple processes simultaneously. It is appreciated that other types of processor arrangements could be implemented to provide the capabilities disclosed herein.

In some embodiments, processing device 202 may use memory interface 204 to access data and a software product stored on a memory device or a non-transitory computer-readable medium. For example, server 145 may use memory interface 204 to access data structure 146. As used herein, a non-transitory computer-readable storage medium refers to any type of physical memory on which information or data readable by at least one processor can be stored. Examples include random access memory (RAM), read-only memory (ROM), volatile memory, nonvolatile memory, hard drives, CD ROMs, DVDs, flash drives, disks, any other optical data storage medium, any physical medium with patterns of holes, a RAM, a PROM, and EPROM, a FLASH-EPROM or any other flash memory, NVRAM, a cache, a register, any other memory chip or cartridge, and networked versions of the same. The terms "memory" and "computer-readable storage medium" may refer to multiple structures, such as a plurality of memories or computer-readable storage mediums located within mobile communications device 115, server 145, or at a remote location. Additionally, one or more computer-readable storage mediums can be utilized in implementing a computer-implemented method. The term "computer-readable storage medium" should be understood to include tangible items and exclude carrier waves and transient signals.

Both mobile communications device 115 and server 145 may include network interface 206 coupled to bus 200. Network interface 206 may provide two-way data communications to a network, such as network 150. In FIG. 2, the wireless communication between mobile communications device 115 and server 145 is represented by a dashed arrow. In one embodiment, network interface 206 may include an integrated services digital network (ISDN) card, cellular modem, satellite modem, or a modem to provide a data communication connection over the Internet. As another example, network interface 206 may include a wireless local area network (WLAN) card. In another embodiment, network interface 206 may include an Ethernet port connected to radio frequency receivers and transmitters and/or optical (e.g., infrared) receivers and transmitters. The specific design and implementation of network interface 206 may depend on the communications network(s) over which mobile communications device 115 and server 145 are intended to operate. For example, in some embodiments, mobile communications device 115 may include network interface 206 designed to operate over a GSM network, a GPRS network, an EDGE network, a Wi-Fi or WiMax network, and a Bluetooth® network. In any such implementation, network interface 206 may be configured to send and receive electrical, electromagnetic or optical signals that carry digital data streams representing various types of information.

Both mobile communications device 115 and server 145 may also include peripherals interface 208 coupled to bus 200. Peripherals interface 208 may be connected to sensors, devices, and subsystems to facilitate multiple functionalities. In one embodiment, peripherals interface 208 may be connected to I/O system 210 configured to receive signals or input from devices and to provide signals or output to one or more devices that allow data to be received and/or transmitted by mobile communications device 115 and server 145. In one example, I/O system 210 may include a touch screen controller 212, audio controller 214, and/or other input controller(s) 216. Touch screen controller 212 may be coupled to a touch screen 218. Touch screen 218 and touch screen controller 212 can, for example, detect contact, movement or break thereof using any of a plurality of touch sensitivity technologies, including but not limited to capacitive, resistive, infrared, and surface acoustic wave technologies as well as other proximity sensor arrays or other elements for determining one or more points of contact with the touch screen 218. Touch screen 218 can also, for example, be used to implement virtual or soft buttons and/or a keyboard. While a touch screen 218 is shown in FIG. 2, I/O system 210 may include a display screen (e.g., CRT or LCD) in place of touch screen 218. Audio controller 214 may be coupled to a microphone 220 and a speaker 222 to facilitate voice-enabled functions, such as voice recognition, voice replication, digital recording, and telephony functions. The other input controller(s) 216 may be coupled to other input/control devices 224, such as one or more buttons, rocker switches, thumbwheel, infrared port, USB port, and/or a pointer device such as a stylus.

With regard to mobile communications device 115, peripherals interface 208 may also be connected to an image sensor 226, a motion sensor 228, a light sensor 230, and/or a proximity sensor 232 to facilitate image capturing, orientation, lighting, and proximity functions. Other sensors (not shown) can also be connected to the peripherals interface 208, such as a temperature sensor, a biometric sensor, or other sensing devices to facilitate related functionalities. In addition, a GPS receiver can also be integrated with, or connected to, mobile communications device 115, such as GPS receivers typically integrated into mobile communications devices. Alternatively, GPS software may permit a mobile communications device to access AN external GPS receiver (e.g., connecting via a serial port or Bluetooth).

Consistent with the present disclosure, mobile communications device 115 may use memory interface 204 to access memory device 234. Memory device 234 may include high-speed random-access memory and/or non-volatile memory such as one or more magnetic disk storage devices, one or more optical storage devices, and/or flash memory (e.g., NAND, NOR). Memory device 234 may store an operating system 236, such as DARWIN, RTXC, LINUX, iOS, UNIX, OSX, WINDOWS, or an embedded operating system such as VXWorkS. The operating system 236 can include instructions for handling basic system services and for performing hardware-dependent tasks. In some implementations, the operating system 236 can be a kernel (e.g., UNIX kernel).

Memory device 234 may also store communication instructions 238 to facilitate communicating with one or more additional devices, one or more computers and/or one or more servers. Memory device 234 can include: graphical user interface instructions 240 to facilitate graphic user interface processing; sensor processing instructions 242 to facilitate sensor-related processing and functions; phone instructions 244 to facilitate phone-related processes and functions; electronic messaging instructions 246 to facilitate electronic-messaging related processes and functions; web browsing instructions 248 to facilitate web browsing-related processes and functions; media processing instructions 250 to facilitate media processing-related processes and functions; GPS/navigation instructions 252 to facilitate GPS and navigation-related processes and instructions; capturing instructions 254 to facilitate processes and functions related to image sensor 226; and/or other software instructions 258 to facilitate other processes and functions. Memory device 234 may also include application specific instructions 260 to facilitate a process for guiding user 110 on the steps of the medical testing. For example, application specific instructions 260 may cause display of a message indicative of image insufficiency for medical testing.

Each of the above identified instructions and applications may correspond to a set of instructions for performing one or more functions described above. These instructions need not be implemented as separate software programs, procedures, or modules. Memory device 234 may include additional instructions or fewer instructions. Furthermore, various functions of mobile communications device 115 may be implemented in hardware and/or in software, including in one or more signal processing and/or application specific integrated circuits. For example, mobile communications device 115 may execute an image processing algorithm to identify objects in a received image. In addition, the components and arrangements shown in FIG. 2 are not intended to limit the disclosed embodiments. As will be appreciated by a person skilled in the art having the benefit of this disclosure, numerous variations and/or modifications may be made to the depicted configuration of server 145. For example, not all components may be essential for the operation of server 145 in all cases. Any component may be located in any appropriate part of server 145, and the components may be rearranged into a variety of configurations while providing the functionality of the disclosed embodiments. For example, some servers may not include all of the elements in I/O system 210.

A convolution may include a convolution of any dimension. A one-dimensional convolution is a function that transforms an original sequence of numbers to a transformed sequence of numbers. The one-dimensional convolution may be defined by a sequence of scalars. Each particular value in the transformed sequence of numbers may be determined by calculating a linear combination of values in a subsequence of the original sequence of numbers corresponding to the particular value. A result value of a calculated convolution may include any value in the transformed sequence of numbers. Likewise, an n-dimensional convolution is a function that transforms an original n-dimensional array to a transformed array. The n-dimensional convolution may be defined by an n-dimensional array of scalars (known as the kernel of the n-dimensional convolution). Each particular value in the transformed array may be determined by calculating a linear combination of values in an n-dimensional region of the original array corresponding to the particular value. A result value of a calculated convolution may include any value in the transformed array.

In some embodiments, machine learning algorithms (also referred to as machine learning models in the present disclosure) may be trained using training examples, for example in the cases described below. Some non-limiting examples of such machine learning algorithms may include classification algorithms, data regressions algorithms, image segmentation algorithms, visual detection algorithms (such as object detectors, face detectors, person detectors, motion detectors, edge detectors, etc.), visual recognition algorithms (such as face recognition, person recognition, object recognition, etc.), speech recognition algorithms, mathematical embedding algorithms, natural language processing algorithms, support vector machines, random forests, nearest neighbors algorithms, deep learning algorithms, artificial neural network algorithms, convolutional neural network algorithms, recurrent neural network algorithms, linear machine learning models, non-linear machine learning models, ensemble algorithms, and so forth. For example, a trained machine learning algorithm may comprise an inference model, such as a predictive model, a classification model, a data regression model, a clustering model, a segmentation model, an artificial neural network (such as a deep neural network, a convolutional neural network, a recurrent neural network, etc.), a random forest, a support vector machine, and so forth. In some examples, the training examples may include example inputs together with the desired outputs corresponding to the example inputs. Further, in some examples, training machine learning algorithms using the training examples may generate a trained machine learning algorithm, and the trained machine learning algorithm may be used to estimate outputs for inputs not included in the training examples. In some examples, engineers, scientists, processes and machines that train machine learning algorithms may further use validation examples and/or test examples. For example, validation examples and/or test examples may include example inputs together with the desired outputs corresponding to the example inputs, a trained machine learning algorithm and/or an intermediately trained machine learning algorithm may be used to estimate outputs for the example inputs of the validation examples and/or test examples, the estimated outputs may be compared to the corresponding desired outputs, and the trained machine learning algorithm and/or the intermediately trained machine learning algorithm may be evaluated based on a result of the comparison. In some examples, a machine learning algorithm may have parameters and hyper parameters, where the hyper parameters may be set manually by a person or automatically by an process external to the machine learning algorithm (such as a hyper parameter search algorithm), and the parameters of the machine learning algorithm may be set by the machine learning algorithm based on the training examples. In some implementations, the hyper-parameters may be set based on the training examples and the validation examples, and the parameters may be set based on the training examples and the selected hyper-parameters. For example, given the hyper-parameters, the parameters may be conditionally independent of the validation examples.

In some embodiments, trained machine learning algorithms (also referred to as machine learning models and trained machine learning models in the present disclosure) may be used to analyze inputs and generate outputs, for example in the cases described below. In some examples, a trained machine learning algorithm may be used as an inference model that when provided with an input generates an inferred output. For example, a trained machine learning algorithm may include a classification algorithm, the input may include a sample, and the inferred output may include a classification of the sample (such as an inferred label, an inferred tag, and so forth). In another example, a trained machine learning algorithm may include a regression model, the input may include a sample, and the inferred output may include an inferred value corresponding to the sample. In yet another example, a trained machine learning algorithm may include a clustering model, the input may include a sample, and the inferred output may include an assignment of the sample to at least one cluster. In an additional example, a trained machine learning algorithm may include a classification algorithm, the input may include an image, and the inferred output may include a classification of an item depicted in the image. In yet another example, a trained machine learning algorithm may include a regression model, the input may include an image, and the inferred output may include an inferred value corresponding to an item depicted in the image (such as an estimated property of the item, such as size, volume, age of a person depicted in the image, cost of a product depicted in the image, and so forth). In an additional example, a trained machine learning algorithm may include an image segmentation model, the input may include an image, and the inferred output may include a segmentation of the image. In yet another example, a trained machine learning algorithm may include an object detector, the input may include an image, and the inferred output may include one or more detected objects in the image and/or one or more locations of objects within the image. In some examples, the trained machine learning algorithm may include one or more formulas and/or one or more functions and/or one or more rules and/or one or more procedures, the input may be used as input to the formulas and/or functions and/or rules and/or procedures, and the inferred output may be based on the outputs of the formulas and/or functions and/or rules and/or procedures (for example, selecting one of the outputs of the formulas and/or functions and/or rules and/or procedures, using a statistical measure of the outputs of the formulas and/or functions and/or rules and/or procedures, and so forth).

In some embodiments, artificial neural networks may be configured to analyze inputs and generate corresponding outputs, for example in the cases described herein. Some non-limiting examples of such artificial neural networks may comprise shallow artificial neural networks, deep artificial neural networks, feedback artificial neural networks, feed forward artificial neural networks, autoencoder artificial neural networks, probabilistic artificial neural networks, time delay artificial neural networks, convolutional artificial neural networks, recurrent artificial neural networks, long short term memory artificial neural networks, and so forth. In some examples, an artificial neural network may be configured manually. For example, a structure of the artificial neural network may be selected manually, a type of an artificial neuron of the artificial neural network may be selected manually, a parameter of the artificial neural network (such as a parameter of an artificial neuron of the artificial neural network) may be selected manually, and so forth. In some examples, an artificial neural network may be configured using a machine learning algorithm. For example, a user may select hyper-parameters for the an artificial neural network and/or the machine learning algorithm, and the machine learning algorithm may use the hyper-parameters and training examples to determine the parameters of the artificial neural network, for example using back propagation, using gradient descent, using stochastic gradient descent, using mini-batch gradient descent, and so forth. In some examples, an artificial neural network may be created from two or more other artificial neural networks by combining the two or more other artificial neural networks into a single artificial neural network.

Some non-limiting examples of image data may include images, grayscale images, color images, 2D images, 3D images, videos, 2D videos, 3D videos, frames, footages, data derived from other image data, and so forth. In some embodiments, analyzing image data (for example in the cases described herein) may comprise analyzing the image data to obtain a preprocessed image data, and subsequently analyzing the image data and/or the preprocessed image data to obtain the desired outcome. One of ordinary skill in the art will recognize that the followings are examples, and that the image data may be preprocessed using other kinds of preprocessing methods. In some examples, the image data may be preprocessed by transforming the image data using a transformation function to obtain a transformed image data, and the preprocessed image data may comprise the transformed image data. For example, the transformed image data may comprise one or more convolutions of the image data. For example, the transformation function may comprise one or more image filters, such as low-pass filters, high-pass filters, band-pass filters, all-pass filters, and so forth. In some examples, the transformation function may comprise a nonlinear function. In some examples, the image data may be preprocessed by smoothing at least parts of the image data, for example using Gaussian convolution, using a median filter, and so forth. In some examples, the image data may be preprocessed to obtain a different representation of the image data. For example, the preprocessed image data may comprise: a representation of at least part of the image data in a frequency domain; a Discrete Fourier Transform of at least part of the image data; a Discrete Wavelet Transform of at least part of the image data; a time/frequency representation of at least part of the image data; a representation of at least part of the image data in a lower dimension; a lossy representation of at least part of the image data; a lossless representation of at least part of the image data; a time ordered series of any of the above; any combination of the above; and so forth. In some examples, the image data may be preprocessed to extract edges, and the preprocessed image data may comprise information based on and/or related to the extracted edges. In some examples, the image data may be preprocessed to extract image features from the image data. Some non-limiting examples of such image features may comprise information based on and/or related to: edges; corners; blobs; ridges; Scale Invariant Feature Transform (SIFT) features; temporal features; and so forth. In some examples, analyzing the image data may include calculating at least one convolution of at least a portion of the image data, and using the calculated at least one convolution to calculate at least one resulting value and/or to make determinations, identifications, recognitions, classifications, and so forth.

In some embodiments, analyzing image data (for example in the cases described herein) may comprise analyzing the image data and/or the preprocessed image data using one or more rules, functions, procedures, artificial neural networks, object detection algorithms, face detection algorithms, visual event detection algorithms, action detection algorithms, motion detection algorithms, background subtraction algorithms, inference models, and so forth. Some non-limiting examples of such inference models may include: an inference model preprogrammed manually; a classification model; a regression model; a result of training algorithms, such as machine learning algorithms and/or deep learning algorithms, on training examples, where the training examples may include examples of data instances, and in some cases, a data instance may be labeled with a corresponding desired label and/or result; and so forth. In some embodiments, analyzing image data (for example in the cases described herein) may comprise analyzing pixels, voxels, point cloud, range data, etc. included in the image data.

Figure 3:
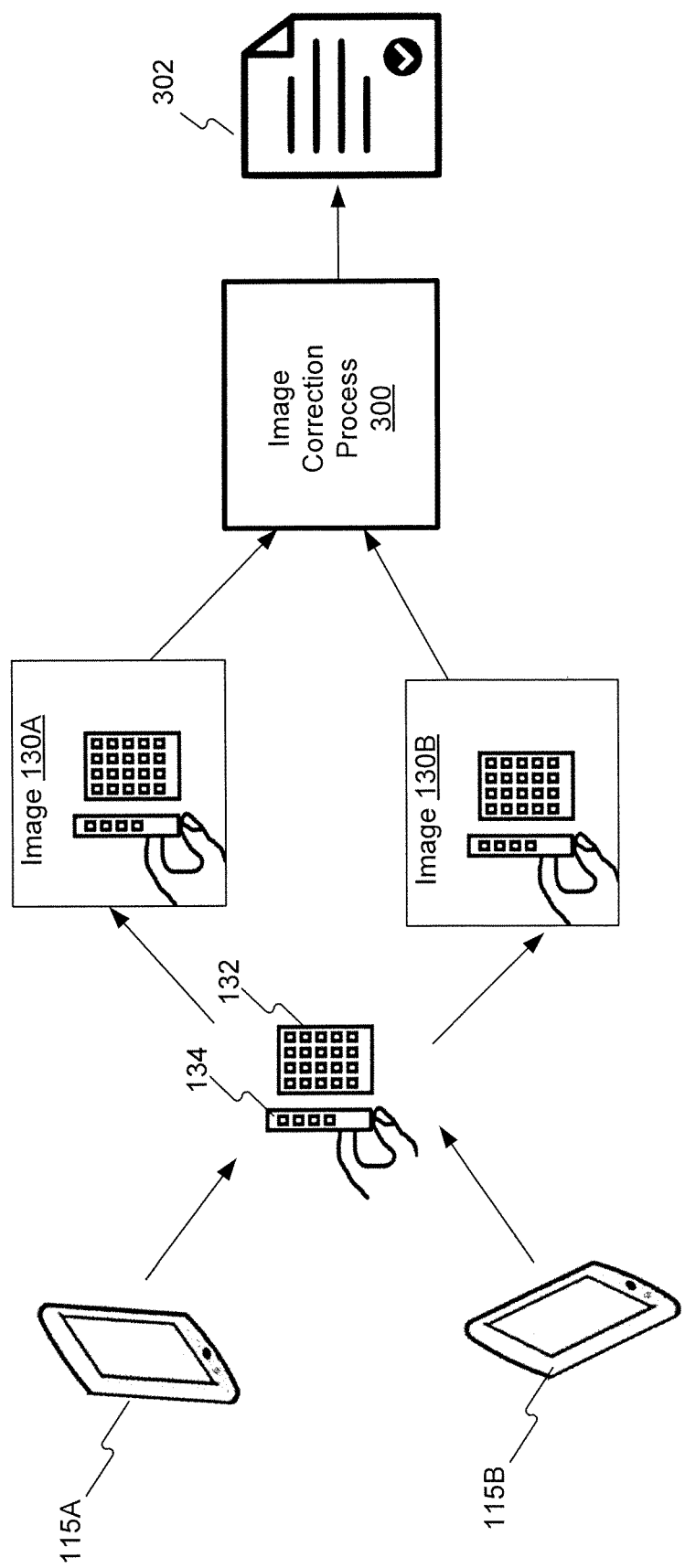
FIG. 3 is a schematic illustration of how two different mobile communications devices can obtain the same test results, consistent with some embodiments of the present disclosure.

As mentioned above, one of the challenges of turning a smartphone into a regulatory-approved clinical device is the lack of uniformity of image capture capabilities of smartphones. FIG. 3 illustrates two communication devices 115 capturing the same object. When a first mobile communications device 115A captures examined object 134 in proximity to colorized surface 132, a first image 130A is acquired. When a second mobile communications device 115B captures examined object 134 in proximity to colorized surface 132, a second image 130B is acquired. First image 130A may be different from second image 130B due to differences between the incorporated image sensors, differences in lighting conditions from different perspectives, and/or differences in image sensor settings. For example, first image 130A may be different from second image 130B because first mobile communications device 115A has different white balance settings and different color correction profiles than second mobile communications device 115B. The white balance settings may be associated with how communications devices 115A, 115B determine the white point for the image and if any tint should be applied to the other colors. The color correction profile may be associated with how communication devices 115A, 115B process color saturation, black levels, highlights, and the contrast of colors in the image. In another example, first image 130A may be different from second image 130B because first mobile communications device 115A has different hardware (such as image sensor resolution, dimensions, filters, color filters, lenses, crop factor, sensitivity, and so forth) than communications device 115B. In yet another example, first image 130A may be different from second image 130B because first mobile communications device 115A has different camera configurations (such as exposure time, shutter speed, aperture, ISO, and so forth) than communications device 115B.

Consistent with the present disclosure, each of image 130A and image 130B may undergo an image correction process 300. Image correction process 300 may include, for example, one or more steps to remove (or to compensate for) local illumination effects and image capturing settings effects. The local illumination effects may result from the type of light source used to light the object, the distance of the object from the light source, a viewing angle of the object, position of the object, ambient light conditions, flash usage, exposure time, and so forth. The image capturing settings effects result from the type of image sensor 226 used to capture the object, image resolution, frame rate, gain, ISO speed, stereo base, lens, focus, zoom, color correction profile, and so forth. In some embodiments of the disclosure, correcting captured image 130 may include reversing any of the tone mapping, color enhancement, white balance, and contrast enhancing of image 130. In addition, correcting image 130 may include simulating standard illumination conditions and reduce shading and specularity effects.

Image correction process 300 is enabled through the use of colorized surface 132. Specifically, the qualities of one or more color swaths on colorized surface 132 may be known in advance. To the extent differences are detected between the actual colors of colorized surface 132 and an image such as image 130A or image 130B, the system may calculate a correction factor necessary to rectify any such differences, and then apply that correction factor to the captured image of object 134.

Image correction process 300 may correct each of image 130A and image 130B differently. For example, image correction process 300 may include increasing the red color in image 130A and adding brightness to image 130B. After images 130A and 130B separately undergo image correction process 300, system 100 may independently determine test results 302 from each of image 130A and image 130B. In accordance with the present disclosure, even though image 130A may be different from image 130B, test results 302 will be the same because both images captured the same known colorized surface 132 whose colorization is known in advance, and which may be used as a basis for generating different correction factors for the varying differences. In some embodiments, system 100 may correct one or more of captured images 130A, 130B using metadata associated with the mobile communications device that captured one or more of captured images 130A, 130B. In other embodiments, system 100 may correct one or more of captured images 130A, 130B without using any information about the mobile communications device that captured one or more of captured images 130A, 130B.

Figure 4A:
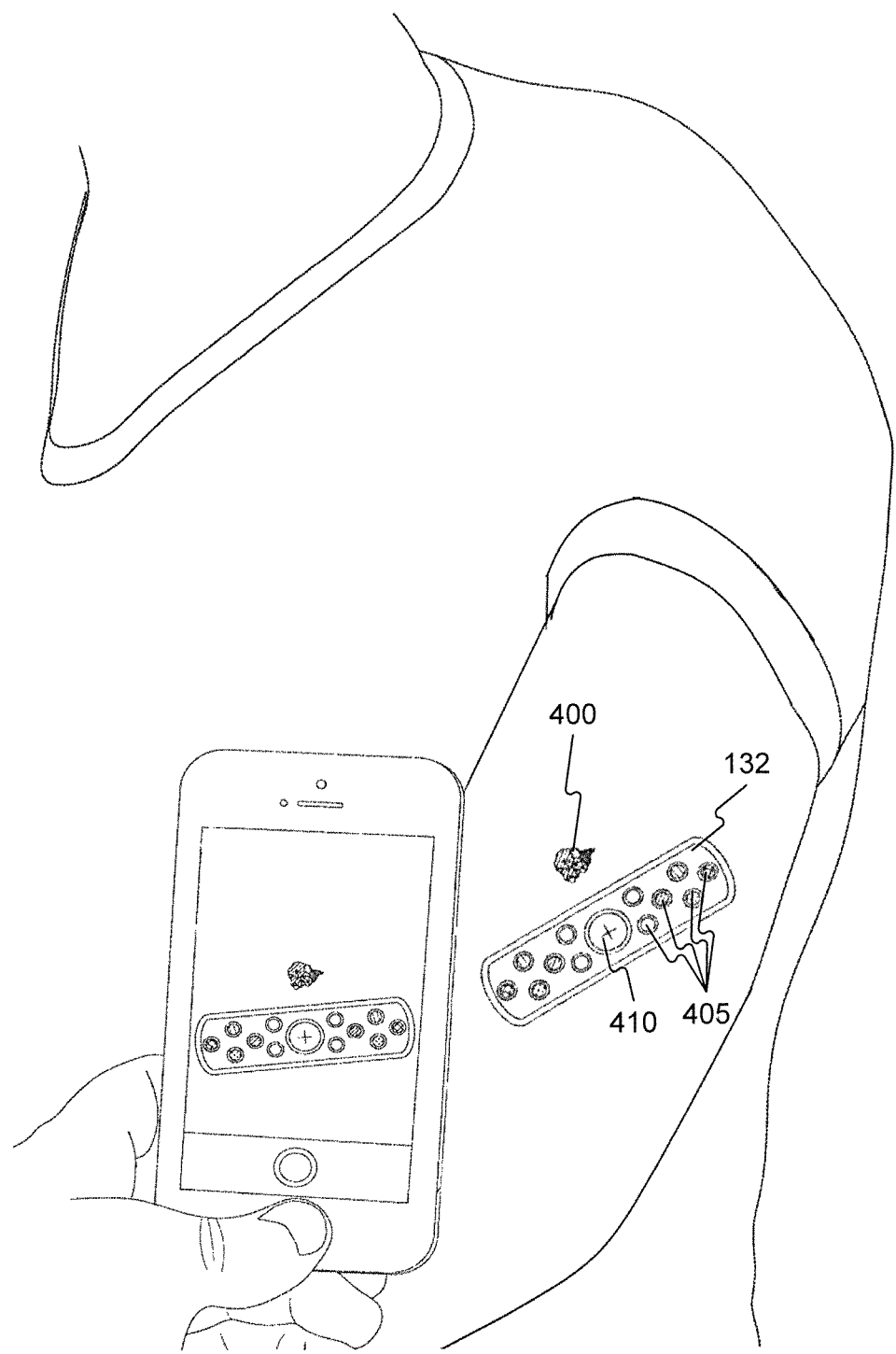
FIG. 4A is an illustration of one aspect of the disclosure where the examined object is a tissue feature, consistent with some embodiments of the present disclosure.
Figure 4B:
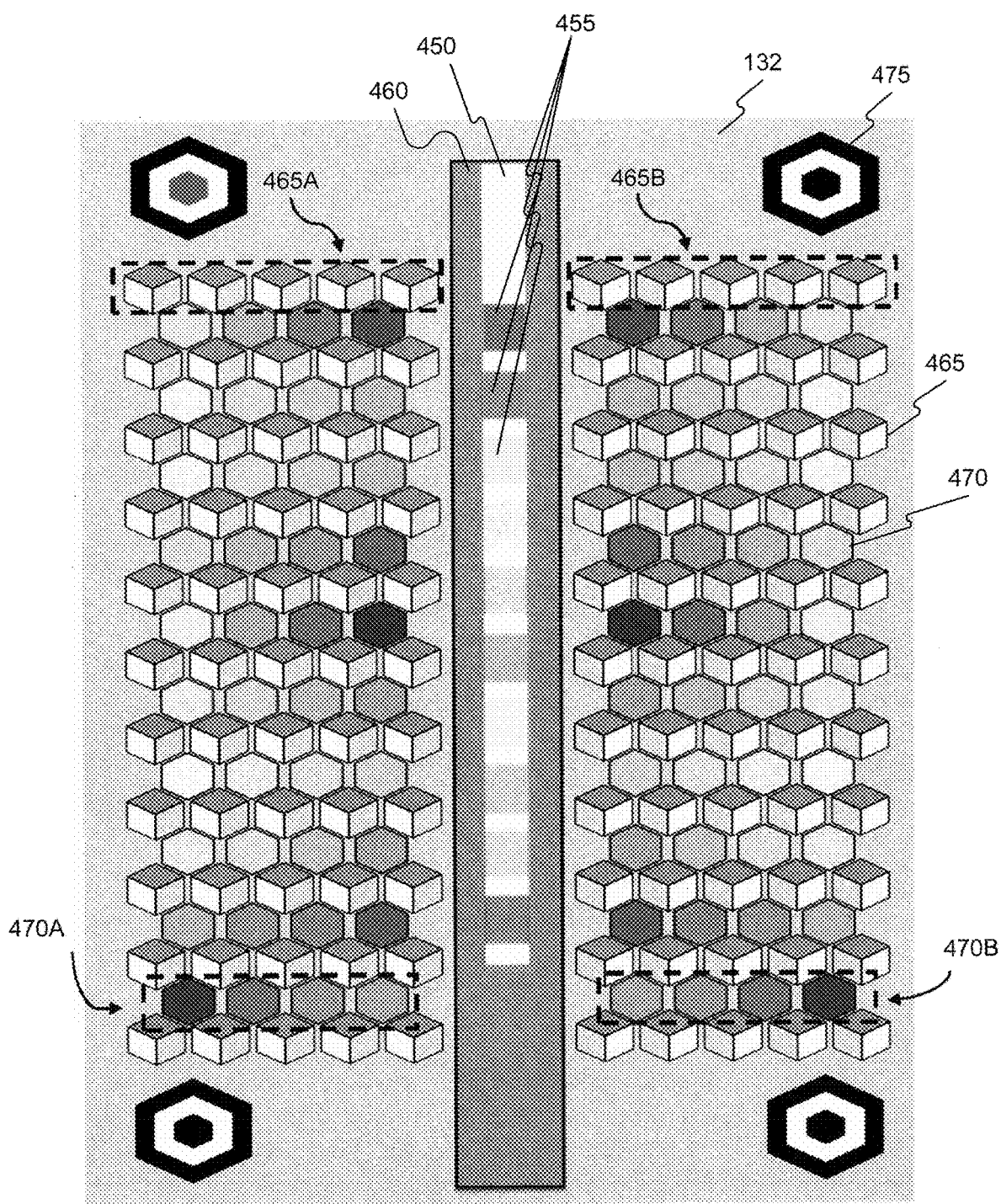
FIG. 4B is an illustration of another aspect of the disclosure where the examined object is a dipstick, consistent with some embodiments of the present disclosure.

FIG. 4A depicts one embodiment where the examined object is a skin feature 400. Consistent with this aspect, system 100 is configured to measure the distribution of colors of skin feature 400 by comparing them to the colors on colorized surface 132. The colors on colorized surface 132 may be selected to include at least some of the expected range of colors of the examined object under various illumination and capturing conditions. It may also include a range of colors from which a correction factor may be generated. As illustrated in FIG. 4A, colorized surface 132 may include a plurality of colored reference elements 405 and may be attachable onto a skin area next to skin feature 400. In certain embodiments, colorized surface 132 may have different forms adapted to a medical condition of user 110 or an expected form and characteristics of skin feature 400. In addition, colorized surface 132 may have different forms adapted to the expected capturing parameters (e.g., to capturing geometry). For example, colorized surface 132 may be round, elongated, curved, have one or more openings therein to accommodate skin feature 400, etc.

Consistent with the present disclosure, colorized surface 132 may have one or more colored reference elements 405 used for calibrating illumination and capturing conditions rather than or in addition to relating to colored reference elements 405 associated with the expected colors in skin feature 400. When skin feature 400 and colorized surface 132 are captured in a single image, system 100 may determine the true colors of captured skin feature 400 by correcting image 130. In some embodiments, colorized surface 132 may also include one or more positioning marks 410 that may be used for image processing purposes and/or for positioning colorized surface 132 accurately with respect to skin feature 400. Moreover, positioning marks 410 may provide a reference of a known dimension that may be used to estimate a size, orientation, and/or a form of skin feature 400. In certain embodiments, dimensional marks 410 may be used (e.g., by image analysis unit 140) to correct captured image 130 with respect to dimensions and forms and to derive an analysis of size and/or form of skin feature 400 and possibly of other image features. For example, image analysis unit 140 may compute the color constancy to determine whether two pixels have the same color in the real world regardless of illumination conditions and/or camera parameters.

In some embodiments, system 100 may provide two dimensional measurements of different sections of skin feature 400 associated with a same color, such as size and shape characteristics (symmetry, boundary length etc.). In additional embodiments, system 100 may track skin feature parameters over time by repeatedly capturing the same skin feature over time. In this regard, the dimensional mark may assist in determining variations over time. In one example, skin feature 400 may include scar tissue or a rash that may be monitored daily to track healing progress. In another example, skin feature 400 may be captured weekly or even monthly for monitoring potentially cancerous features or developments. When collecting such data over a period of time, an additional step may be added for verifying that the correction of image 130 is consistent across the time period in which the data was collected. Correcting image 130 may further include taking into account illumination conditions and capturing parameters associated with previously captured images. Additional details on the first aspect of the disclosure are described in Applicant's U.S. Pat. No. 10,362,984, which is incorporated herein by reference in its entirety.

FIG. 4B provides an example of a colorized surface for use with a dipstick 450 having at least one reagent pad 455. In use, system 100 may be configured to measure the extent of a chemical reaction on at least one reagent pad 455 by comparing a color of a reagent pad with the calibration elements 470 on colorized surface 132. The calibration elements on colorized surface 132 may be selected to represent at least some of the expected range of colors of the examined object under various illumination and capturing conditions. As illustrated in FIG. 4B, colorized surface 132 may include a dipstick placement region 460 and a plurality of calibration elements 470 located on opposing sides of dipstick placement region 460.

In some embodiments, colorized surface 132 may include a plurality of grey elements 465A and 465B that may be used for determining local illumination conditions. Colorized surface 132 may also include a plurality of colored reference elements that may have been selected to correspond to expected colors of dipstick 450 under various different possible illumination conditions, capturing devices, and image processing abilities of mobile communications devices 115. FIG. 4B shows a non-limiting example of colorized surface 132 exhibiting a grid of cube-like grey elements 465 having three sides, each having a different shade of grey, and a plurality of hexagon-shaped colored reference elements 470 used as reference values for image color correction. On the depicted colorized surface 132, at least two groups of grey elements with the same shade scheme (e.g., group of grey elements 465A and group of grey elements 465B) and at least two groups of colored reference elements with the same color scheme (e.g., a group of colored reference elements 470A and a group of colored reference elements 470B) may be located on opposing sides of dipstick placement region 460.

According to some embodiments, colorized surface 132 may be provided with geometrical elements that differ from geometrical shapes contained on the dipstick to enable differentiation between colored reagents on the dipstick and elements on the colorized surface. Some elements on colorized surface 132 may exhibit various shades of gray for improved gamma correction. Moreover, colorized surface 132 may be provided with calibration elements 470 surrounded by borders for minimizing over smoothing of certain colors by some camera models. Additionally, colorized surface 132 may be provided with high contrast elements 475 for enabling fast binary large object (BLOB) based color board rectification on mobile communications device 115.

Figure 5A:
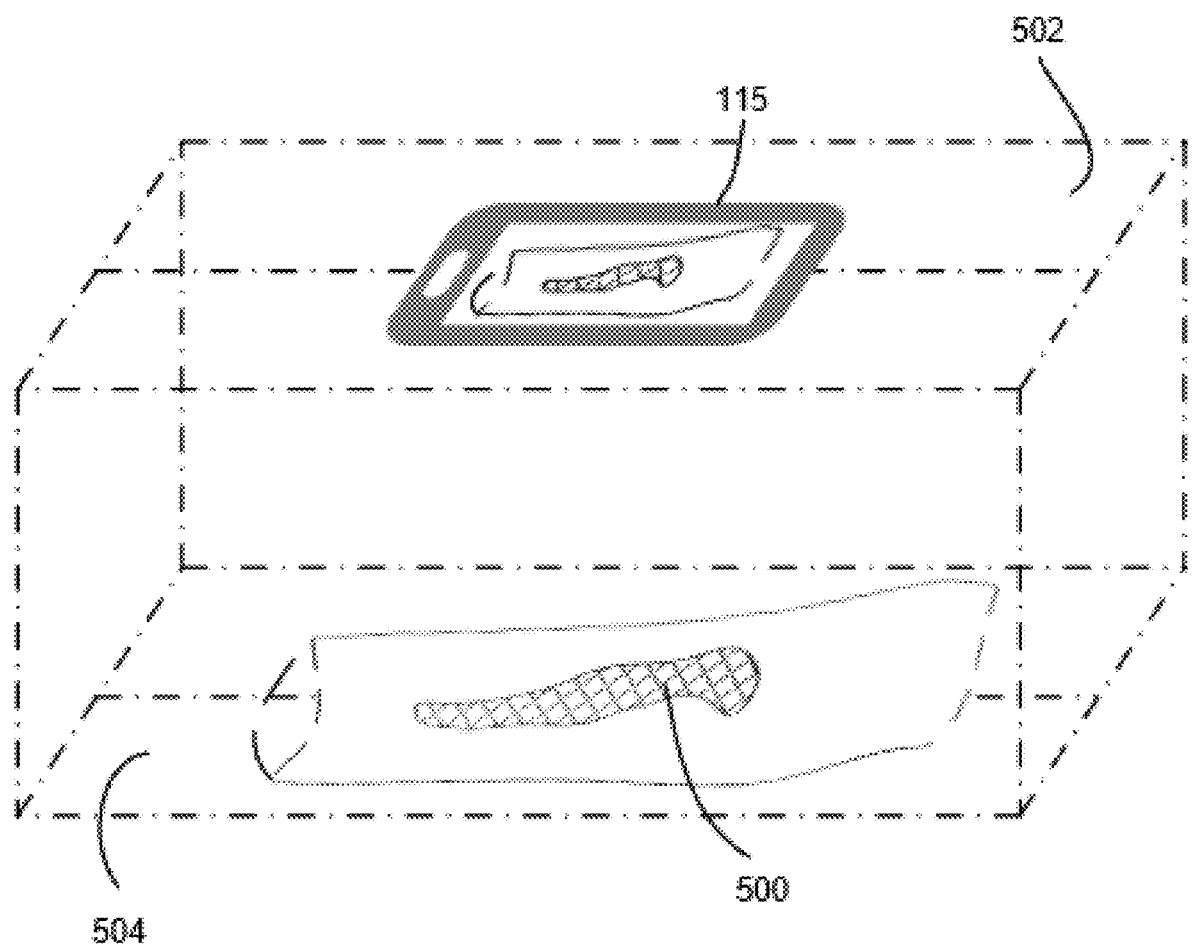
FIG. 5A is an illustration of a mobile communications device capturing an image or video of an example wound, the device parallel to the wound, consistent with some embodiments of the present disclosure.

Aspects of this disclosure may relate to systems, methods, devices, and computer readable media storing instructions for generating cross section views of a wound. As used herein, a cross section of a wound may refer to a depiction of a surface that is or may be exposed by a plane cutting through the wound transversely, including, for example, at a right angle or substantially at a right angle of an axis. In one example, the depicted surface may be substantially perpendicular to a surface of a skin of a patient and/or to a surface of the wound. In another example, the depicted surface may be at a non-zero angle to the surface of a skin of the patient and/or to the surface of the wound (for example, at an angle larger than 1 degree, larger than 5 degrees, larger than 15 degrees, larger than 30 degrees, larger than 45 degrees, larger than 75 degrees, and so forth). A wound may include any injury to the human body. For example, wounds may be open wounds resulting from penetration (e.g., puncture wounds, surgical wounds and incisions, thermal, chemical, or electric burns, bites and stings, gunshot wounds, etc.) and/or blunt trauma (e.g., abrasions, lacerations, skin tears), or they may include closed wounds (e.g., contusions, blisters, seromas, hematomas, crush injuries, etc.). Some non-limiting examples of a wound may include a chronic wound, acute wounds, ulcer (such as venous ulcer, arterial ulcer, diabetic ulcer, pressure ulcer, etc.), infectious wound, ischemic wound, surgical wound, radiation poisoning wound, and so forth. By way of example, server 145 of FIGS. 1A and 2 may be configured to generate one or more cross section views of a wound 500 shown in FIG. 5A.

Figure 5B:
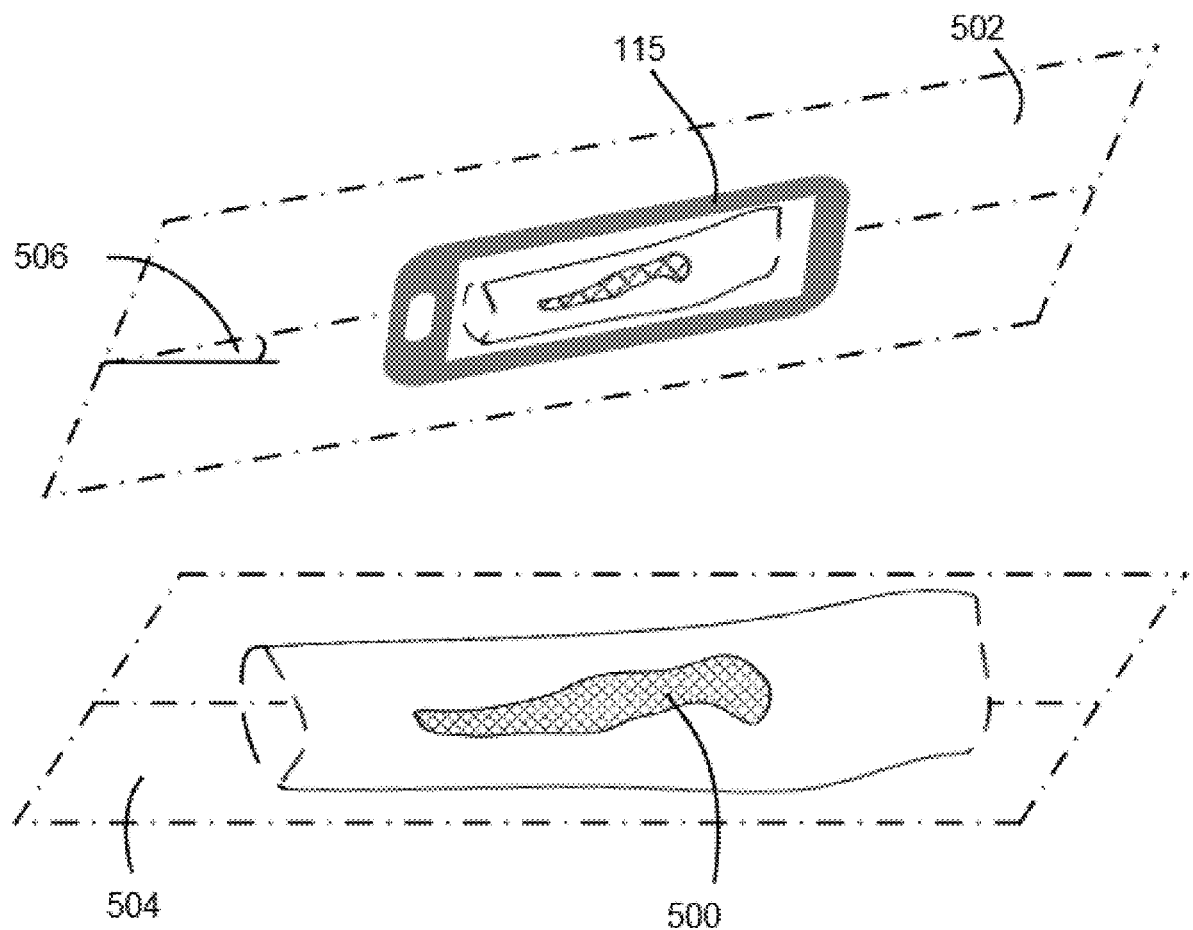
FIG. 5B is an illustration of a mobile communications device capturing an image or video of an example wound, the device substantially parallel to the wound, consistent with some embodiments of the present disclosure.

Embodiments consistent with the present disclosure may include receiving 3D information of a wound based on information captured using an image sensor associated with an image plane substantially parallel to the wound. Some non-limiting examples of such image sensor may include color image sensor, grayscale image sensor, stereoscopic image sensor, active stereo image sensor, time-of-flight image sensor, structure from motion sensor, and so forth. In some embodiments, 3D information of a wound may refer to any data which may describe a three-dimensional shape or form of a wound. Some non-limiting examples of such 3D information may include stereoscopic images, depth images, range images, arrays of voxels, geometric models (such as a manifold modeling the outer surface of the wound), polygon meshes, point clouds, and so forth. For instance, 3D information of the wound may include image data such as pixel data streams, digital images, digital video streams, and data derived from an analysis of images captured using the image sensor, and/or written data provided in a numerical or textual manner such as a length or depth of a wound. The 3D information of the wound may be received via a wired or wireless transmission from an external device, such as a mobile communications device, as described in greater detail herein. In some embodiments, the 3D information may be extracted or otherwise determined based on information captured using an image sensor. An image sensor may be part of a camera included in a mobile communications device, as described in greater detail herein. In some embodiments, the captured information may be associated with an image plane substantially parallel to the surface of the wound. That is, the information may be captured by a device which is in a plane parallel to the surface of the wound such that the resulting captured image is in an image plane parallel to the surface of the wound, i.e., the image plane and the wound plane at the surface of the wound are planes in space that will never intersect. Alternatively, the image plane may be only substantially parallel to the wound, in which case, the planes may intersect at a point far away from the wound. In some embodiments, the angle created by the intersection of the substantially parallel image and wound planes may be less than 1°, less than 2°, less than 5°, less than 10°, less than 20°, or less than 30°. By way of example, server 145 of FIG. 2 may receive 3D information of wound 500 of FIG. 5A based on one or more images or a video captured by image sensor 226 of mobile communications device 115 via communications network 150 of FIG. 1A. Mobile communications device 115 may be in an image plane 502 parallel to a wound plane 504 such that an image or video captured by image sensor 226 may be parallel to wound plane 504. Alternatively, as shown in FIG. 5B, mobile communications device 115 may be at an angle 506 to wound plane 504 such that the resulting image or video captured by image sensor 226 is substantially parallel to wound plane 504.

Figure 6:
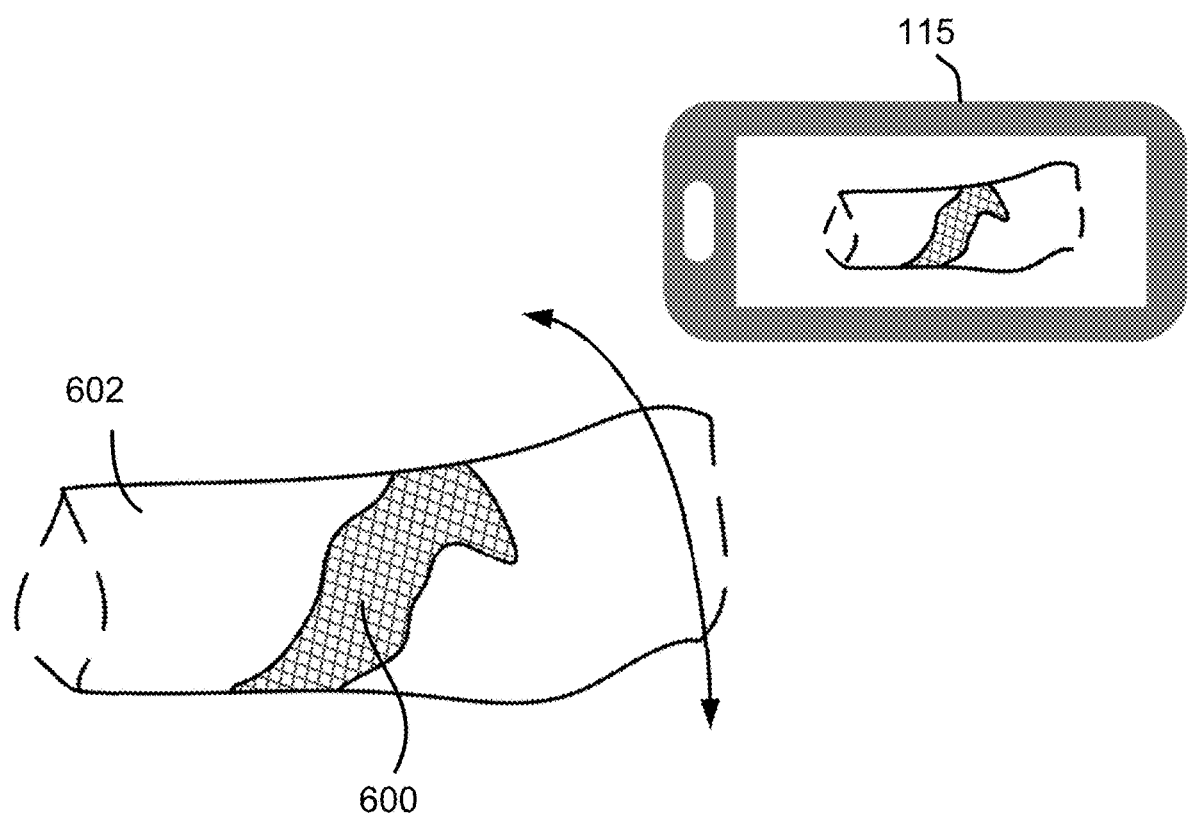
FIG. 6 is an illustration of a mobile communications device capturing one or more images or videos of an example wound at different angles while remaining parallel to the wound, consistent with some embodiments of the present disclosure.

In some embodiments, the 3D information of the wound may include at least one of a range image, a stereoscopic image, a volumetric image, or a point cloud. A range image may refer to a 2D image showing the distance to points in a scene from a specific point, wherein each pixel of the image may express the distance between a known reference frame and a visible point in the scene. A stereoscopic image may refer to two nearly identical images which may be paired to produce the illusion of a single three-dimensional image. A volumetric image may refer to a 3D array of voxels, each voxel representing a 3D area of the scene. A point cloud may refer to a set of data points in space which may represent a sample of point from a three-dimensional shape or object. In some embodiments, the 3D information of the wound may include at least one of a plurality of 2D images of the wound captured from different angles, a stereoscopic image of the wound, an image captured using an active stereo camera, or an image captured using a time-of-flight camera. An active stereo camera may refer to a device which may employ a light such as a laser or a structured light to simplify the process of finding pixels in the multiscopic views that correspond to the same 3D point in the scene. A time-of-flight camera may refer to a range imaging camera system which may employ time-of-flight techniques to resolve distances between the camera and the subject for each point of the image. By way of example, mobile communications device 115 of FIG. 5A may take or render from one or more images or videos one or more of a range image, a stereoscopic image, a volumetric image, or a point cloud. Additionally or alternatively, a user operating mobile communications device 115 may take a plurality of images or videos at a plurality of angles with respect to the wound. For instance, wound 600 of FIG. 6 may be on a 3D surface and may not fit perfectly on one plane, therefore, mobile communications device 115 may rotate around an arm 602 to take a video or more than one picture to capture wound 600 at different angles while remaining parallel to wound 600.

In some embodiments, receiving the 3D information of the wound may include one or more of analyzing a video of the wound captured using the image sensor while the image sensor is moving, analyzing a video of the wound depicting a motion of the wound, or analyzing at least one image captured using the image sensor. In one example, analyzing a video or at least one image to obtain the 3D information may include usage of structure from motion algorithms. In another example, analyzing the video or the at least one image to obtain the 3D information may include analyzing the video or the at least one image using computer stereo vision algorithms. In some examples, a machine learning model may be trained using training examples to determine 3D information of wounds from images and/or videos of the wounds. An example of such training example may include a sample one or more images of a sample wound and/or a sample video of the sample wound, together with 3D information corresponding to the sample wound. The trained machine learning model may be used to analyze at least one of the video of the wound captured using the image sensor while the image sensor is moving, the video of the wound depicting a motion of the wound, or the at least one image captured using the image sensor to determine the 3D information. In some embodiments, a user may move the image sensor while recording a video such that the produced video captures the wound at a plurality of points in space at one or more image planes substantially parallel to the wound. Additionally or alternatively, the user may produce the video such that it captures a motion of the wound, for example while the image sensor is static or while the image sensor is also moving. For example, in FIG. 6, a video and/or a series of images of wound 600 may be captured by an image sensor includes in mobile communications device 115 while wound 600 moves with arm 602. The image sensor included in mobile communications device 115 may or may not move while capturing the video and/or the series of images. Further, a user may capture at least one image via the image sensor and the at least one image may be analyzed separately or in conjunction with a video.

Figure 7:
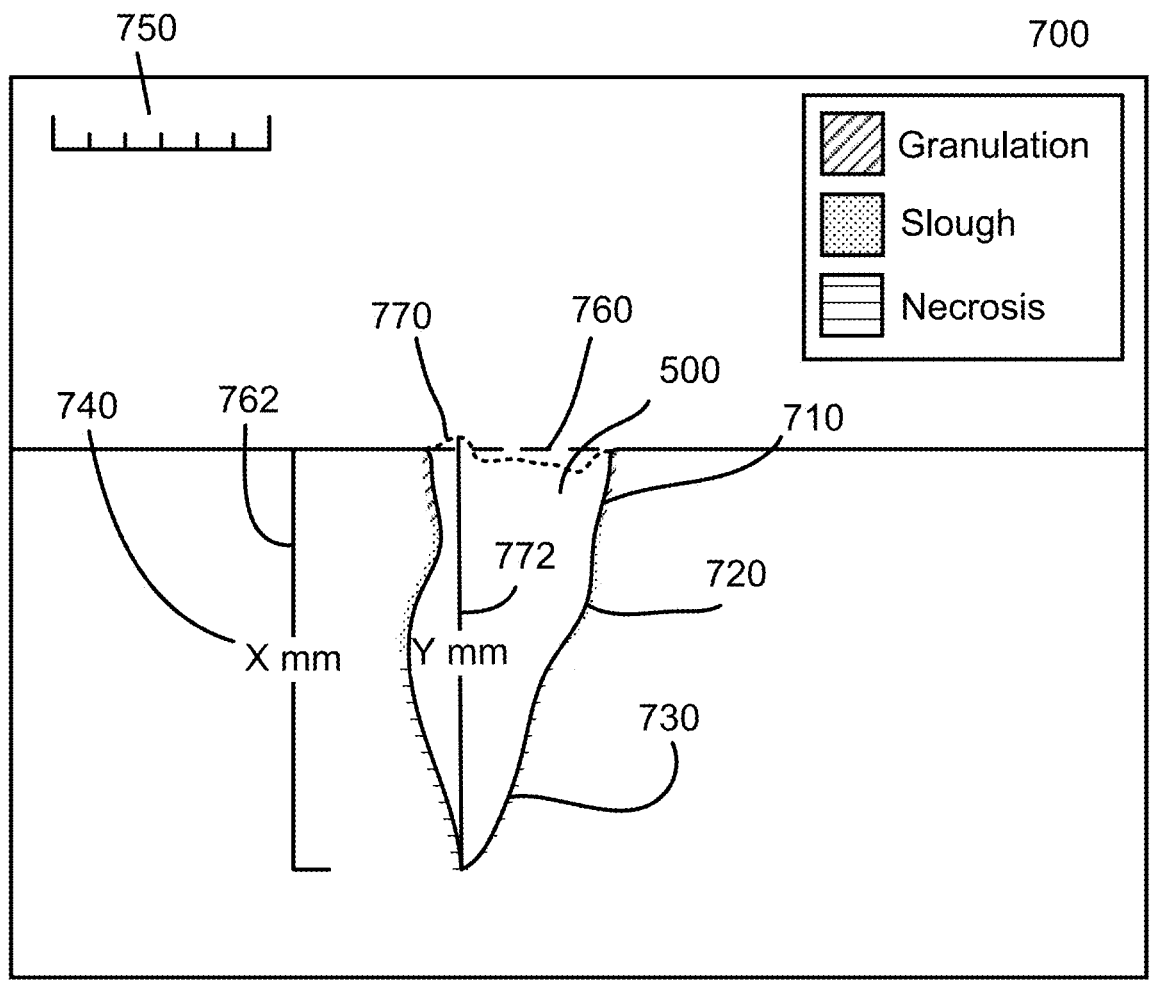
FIG. 7 is an illustration of an example cross section view of a wound, consistent with some embodiments of the present disclosure.

Embodiments consistent with the present disclosure may include generating a cross section view of the wound by analyzing the 3D information. A cross section view of a wound may refer to a depiction, for example in a 2D image or in a curve showing the depth of the wound along the cross section, of a surface that is or would be exposed by making a straight cut through the wound by a plane at a right angle or substantially at a right angle of an axis. The generated cross section view of the wound may include a plurality of parallel cross section views of the wound, for example at parallel planes intersecting the wound at different points. In some examples, a machine learning model (for example, a generative model, such as a generative adversarial network, a transformers based model, etc.) may be trained using training examples to generate cross section views of wounds from 3D information. An example of such training example may include a sample 3D information of a sample wound together with an indication of a desired sample cross section of the sample wound (such as a geometric parameters of a surface of the desired cross section), together with the desired cross section view of the sample wound corresponding to the desired sample cross section, for example in a form of a 2D image. The trained machine learning model may be used to analyze the 3D information and generate the cross section view. In some examples, the 3D information may include a 3D array of voxels. In one example, the analysis of the 3D information may include determining a pixel of the cross section view by selecting a corresponding voxel in the 3D array and determining the value of the pixel as a function (such as an identity function, a monotonic function, a non-monotonic function, etc.) of the selected voxel. In another example, the analysis of the 3D information may include determining a pixel of the cross section view by calculating a 3D convolution of at least some of the voxels of the 3D array. In some examples, the 3D information may include a depth image or a range image, the cross section view may include a curve showing the depth of the wound along the cross section (such as a graph of depths), and the analysis of the 3D information may include determining the depth of the wound represented at a particular location on the curve from the 3D information. In one example, the determination of the depth of the wound represented at the particular location on the curve may including selecting a pixel of the range image and/or depth image, and determining the depth of the wound represented at the particular location on the curve to be the depth corresponding to the selected pixel (or a function of that depth). In another example, the determination of the depth of the wound represented at the particular location on the curve may including calculating a 2D convolution of at least part of depths in the range image and/or depth image. In some examples, the determination of the depth of the wound represented at the particular location on the curve may including determining the depth from the 3D information. Generating a cross section view of the wound may refer to creating a depiction of a cross section view of the wound based on the analysis of the 3D information. The generated depiction may be an image, a collection of images, a 2D image, a collection of 2D images, a video, a curve showing the depth of the wound along the cross section, or any other appropriate medium for representing a cross section view of a wound. By way of example, FIG. 7 illustrates an example of a cross section view 700 of wound 500 generated by analyzing the 3D information generated by mobile communications device 115.

Figure 8A:
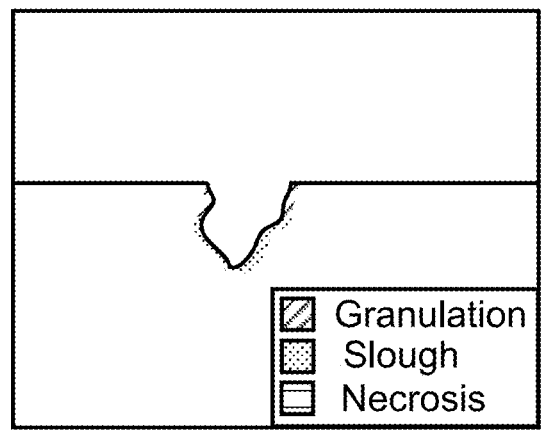
FIG. 8A is an illustration of an example of a first cross section of a wound, consistent with some embodiments of the present disclosure.
Figure 8B:
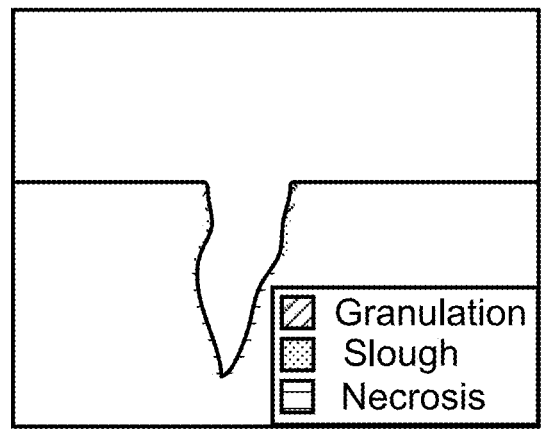
FIG. 8B is an illustration of an example of a second cross section of a wound, consistent with some embodiments of the present disclosure.
Figure 8C:
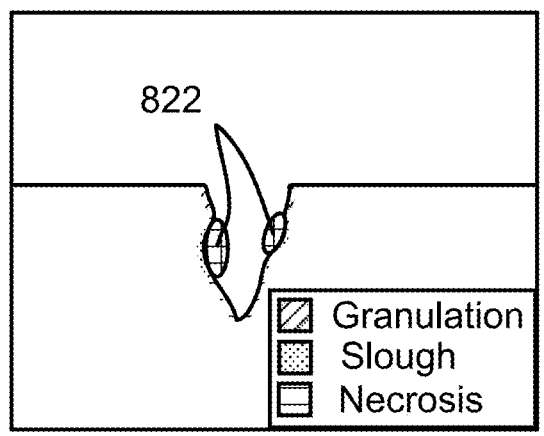
FIG. 8C is an illustration of an example of a third cross section of a wound, consistent with some embodiments of the present disclosure.

In some embodiments, generating the cross section of the wound may include selecting a cross section of the wound from a plurality of cross sections of the wound based on the 3D information and generating the cross section view of the wound by analyzing the 3D information, the cross section view of the wound corresponding to the selected cross section. Selecting a cross section of the wound from a plurality of cross sections based on the 3D information may refer to determining a particular plane intersecting the wound at a particular angle and a particular orientation based on the received 3D information of the wound. For instance, the selected cross section of the wound may correspond to a deepest point of the wound, a shallowest point of the wound, a major or minor axis of the wound, an edge of the wound, an area of the wound which appears infected, or any other area of the wound which may be of interest to a medical professional for further analysis. By way of example, FIGS. 8A, 8B and 8C illustrate three cross sections 800, 810, and 820 of wound 500 at different points in the wound. In some examples, generating the cross section view may include selecting a cross section of wound 500 corresponding to the deepest point in wound 500, which may correspond to cross section 810. In other examples, generating the cross section view may include selecting a cross section of wound 500 corresponding to the shallowest point in wound 500, which may correspond to cross section 800. In yet other examples, generating the cross section view may include selecting a cross section of wound 500 corresponding to an area of the wound which appears infected, such as infected areas 822 of cross section 820.

In some embodiments, generating the cross section view of the wound may include selecting a cross section of the wound from a plurality of cross sections of the wound based on a boundary contour of the wound and generating the cross section view of the wound by analyzing the 3D information, the cross section view of the wound corresponding to the selected cross section. A boundary contour of the wound may refer to the perimeter of the wound. Selecting a cross section of the wound based on the boundary contour of the wound may include selecting a cross section of the wound corresponding to a longest chord of a shape of the boundary contour, a shortest chord of the shape of the boundary contour, a plane perpendicular to one of the longest chord or the shortest chord of the shape of the boundary contour, a plane tangent to the boundary contour of the wound, two or more planes at a particular distance from one of the longest chord or the shortest chord of the shape of the boundary contour, or any other appropriate cross section selection which may be based on the boundary contour of the wound. A chord may refer to a straight line segment whose endpoints both lie on the boundary contour or perimeter of the wound.

Figure 9:
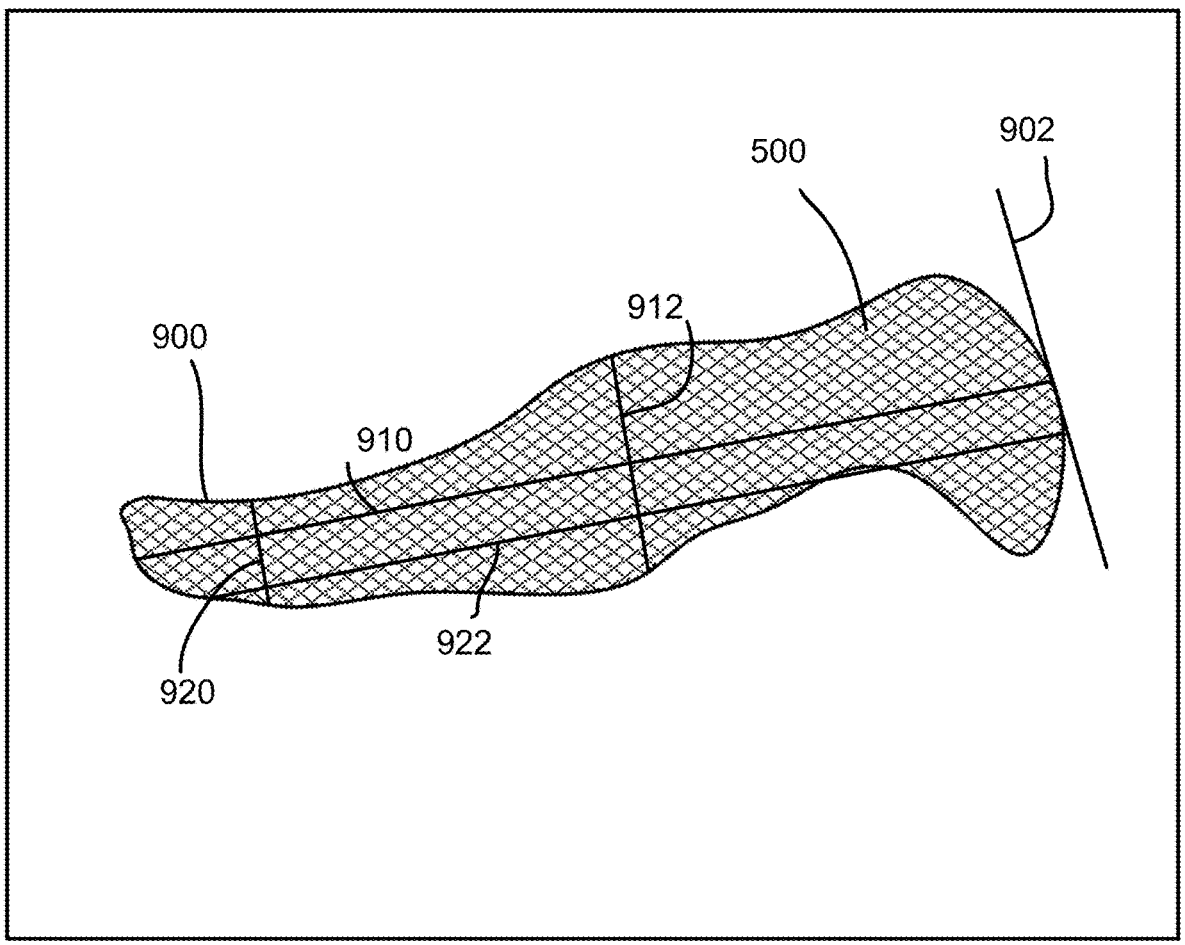
FIG. 9 is an illustration of a front view of a wound, consistent with some embodiments of the present disclosure.

By way of example, FIG. 9 illustrates a front view of wound 500 depicting a boundary contour 900 of wound 500. In some examples, generating the cross section view may include selecting a cross section of wound 500 corresponding to a longest chord 910. In other examples, generating the cross section view may include selecting a cross section of wound 500 corresponding to a shortest chord 920. In yet other examples, generating the cross section view may include selecting a cross section of wound 500 corresponding to a plane perpendicular to one of the longest chord (e.g., chord 912) or the shortest chord (e.g., chord 922). In other examples, generating the cross section view may include selecting a cross section view of wound 500 corresponding to a plane tangent to boundary contour 900 (e.g., tangent 902).

In some embodiments, generating a cross section view of the wound may include obtaining a segmentation of the wound based on a tissue type, selecting a cross section of the wound from a plurality of cross sections of the wound based on the segmentation of the wound, and generating the cross section view of the wound by analyzing the 3D information, the cross section view of the wound corresponding to the selected cross section. Obtaining a segmentation of the wound based on a tissue type may refer to receiving, generating, or otherwise acquiring a division into separate parts or segments of the wound based on different tissue types present in the wound. For instance, a wound may be segmented based on different areas of the wound consisting of different types of tissues. Tissue types may include epithelial tissue, granulation tissue, slough tissue, eschar, necrotic tissue, scab, hematoma, tendon, ligament, bone, infected tissue, non-infected tissue, or any other type of tissue which may be found in a wound. In some embodiments, a cross section of the wound may be selected based on the segmentation of the wound, for example, to generate a cross section view of a wound for one or more particular tissue types, to exclude a particular tissue type from the cross section view, or to ensure one or more particular tissue types are present in the cross section view.

Figure 10:
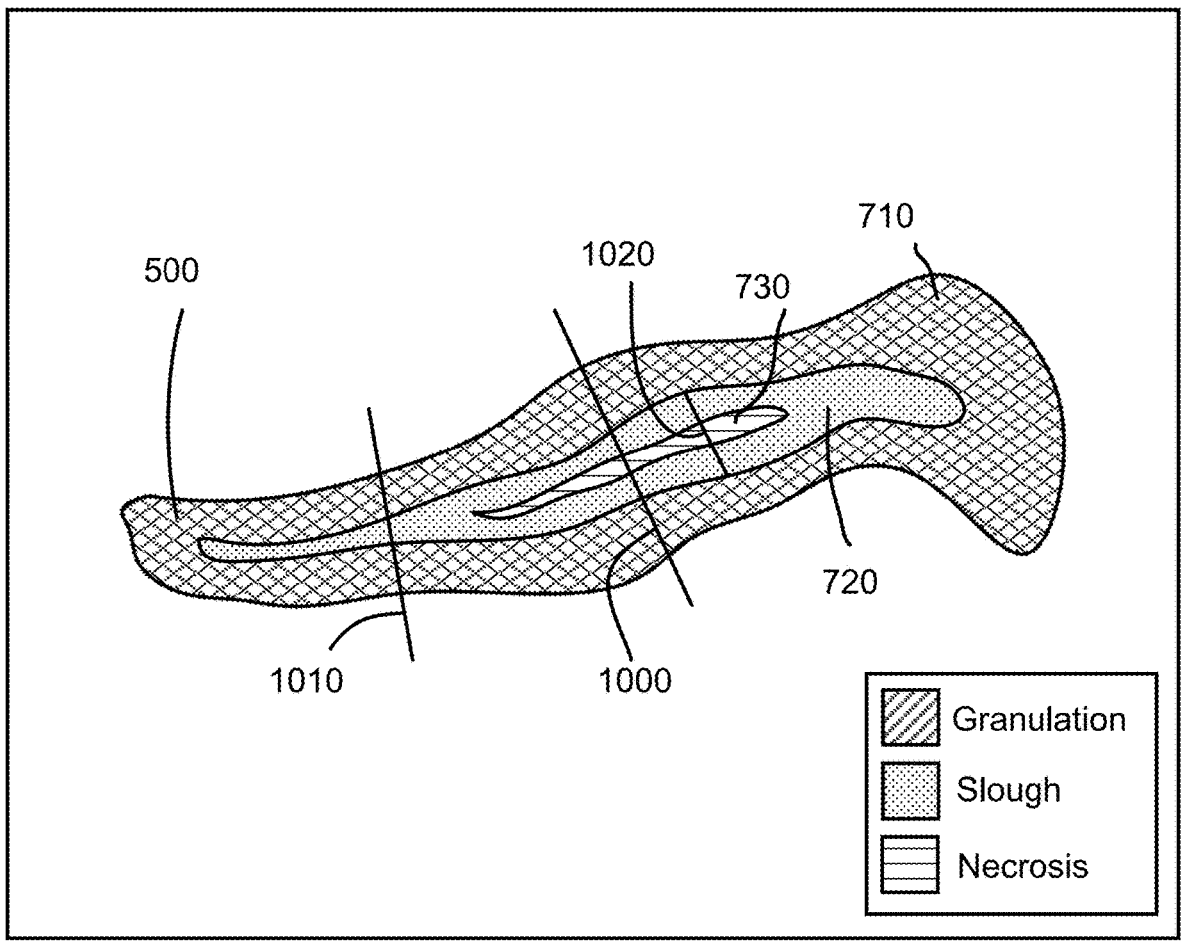
FIG. 10 is an illustration of a front view of a wound segmented by tissue type, consistent with some embodiments of the present disclosure.

By way of example, FIG. 10 illustrates a front view of wound 500 depicting a segmentation of wound 500 based on tissue type. For instance, wound 500 may be segmented into granulation tissue 710, slough tissue 720, and necrosis tissue 730. In some examples, generating the cross section view may include selecting a cross section view of wound 500 which includes granulation tissue, slough tissue, and necrosis tissue, such as cross section 1000. In other examples, generating the cross section view may include selecting a cross section view of wound 500 which includes granulation tissue and slough tissue, but not necrosis tissue, such as cross section 1010. In yet other examples, generating the cross section view may include selecting a cross section view of wound 500 which includes slough tissue and necrosis tissue, but not granulation tissue, such as cross section 1020. In other examples, generating the cross section view may include selecting a cross section view of wound which includes a desired group of tissues, which do not include tissues of a selected group of tissues, which includes a desired combination of tissues (such as a desired ratio of tissues), or any combination of the above.

In some embodiments, the generated cross section view of the wound may include one or more of tissue information for at least a portion of the wound, a visual indication of a wound depth, an estimated pre-wound skin contour, and/or an estimated post-wound skin contour. Tissue information for at least a portion of the wound may include a description of which areas of the wound represented in the cross section view correspond to which tissue types and any other information which may be relevant, for example, how large each portion of the wound is or data about each particular tissue type. A visual indication of a wound depth may include, for example, dimensions, scales, or coloration. Estimated pre-wound and post-wound skin contours may refer to generated estimations of the skin in the area of the wound before the wound existed on the body and after the wound has healed. In some embodiments, the estimated pre-wound and post-wound skin contours may be determined by analyzing the 3D information. By way of example, FIG. 7 illustrates cross section view 700 of wound 500, which may include tissue information for wound 500. For instance, cross section view 700 depicts tissue information corresponding to granulation tissue 710, slough tissue 720, and necrosis tissue 730. Additionally or alternatively, cross section view 700 may include a visual indication of the depth of wound 500 at that point. For instance, numerical indication 740 and scale 750 may both provide a user with an indication of a wound depth. In some embodiments, cross section view 700 may include an estimated pre-wound skin contour 760 and/or an estimated post-wound skin contour 770. In some examples, a machine learning model (for example, a generative model, such as a generative adversarial network, a transformers based model, etc.) may be trained using training examples to determine estimated pre-wound and/or post wound skin contours from 3D information of wounds. An example of such training example may include sample 3D information of a sample wound, together with a desired estimation of the pre-wound and/or a post-wound skin contour for the sample wound, for example in as a function assigning a pre-wound and/or the post-wound skin depth for each position (and/or pixel) of the sample wound, as an overlay in an image of the sample wound, and so forth. The trained machine learning model may be used to analyze the 3D information and determine the estimated pre-wound and/or post-wound skin contours. In some examples, the 3D information of the wound may compared with 3D information of a symmetrical body part and/or of a generic body part corresponding to the body part associated with the wound, and the estimated pre-wound and/or post-wound skin contours may be selected to mimic the symmetrical body part and/or the generic body part. In some examples, the 3D information may include a 3D image of the wound, the area of the wound may be removed from the 3D image (for example using a semantic segmentation algorithm), and an inpainting algorithm may analyze the 3D with the wound removed to generate a 3D image of the pre-wound and/or the post-wound skin. The generated image may be compared with the 3D image of the wound to determine the pre-wound and/or the post-wound skin depth.

Embodiments consistent with the present disclosure may include providing data configured to cause a presentation of the generated cross section view of the wound. The provided data may include data relating to the generated cross section view of the wound, including the generated cross section view of the wound itself, and data for causing a display to present the generated cross section view of the wound to a user, for instance, a medical professional. The data may be provided via physical or virtual displays such as televisions, computer monitors, head-mounted displays, virtual reality headsets, medical monitors, broadcast reference monitors, mobile displays, smartphone displays, video walls, or any other appropriate type of display. By way of example, data may be provided to a device such as mobile communications devices 115, 125, and/or 165 of FIG. 1A to cause a presentation of a generated cross section view of a wound such as cross section view 700 of wound 500 of FIG. 3.

Some embodiments of the present disclosure may include receiving image data captured using the image sensor and calculating a convolution of a first part of the image data to derive a first result value of the convolution of the first part of the image data.

In some embodiments, a depth of the wound at a first position may be determined based on the first result value. The depth of the wound at a first position may refer to a distance between the surface of the skin to the lowest point in the wound at a first position corresponding to the first part of the image data. In one example, in response to a one value of the first result value, a first depth of the wound at the first position may be determined, and in response to another value of the first result value, a second depth of the wound at the second position may be determined, the second depth may differ from the first depth. In another example, the determined depth of the wound at the first position may be a function of the first result value. Some non-limiting examples of such function may include a linear function, a non-linear function, a monotonic function, a non-monotonic function, a polynomial function, an exponential function, a logarithmic function, and so forth. In one example, the function may be obtained by training a machine learning model using training examples to determine depth of wounds from result values of convolutions. An example of such training example may include a sample result value of a convolution of at least part of a sample image of a sample wound, together with a label indicating the depth of the sample wound.

Some embodiments of the present disclosure may include calculating a convolution of a second part of the image data to derive a second result value of the convolution of the second part of the image data, the second part of the image data differing from the first part of the image data. A second part of the image data may refer to a portion of the image data different to the first part of the image data. For instance, this may refer to a different portion of the same image, a different image in a plurality of images, a different portion in a video, or any other different appropriate portion of the image data from which the depth of the wound may be determined based on a value of a convolution. In some embodiments, a depth of the wound at a second position based on the second result value may be determined, the second position differing from the first position. The depth of the wound at a second position may refer to the distance from the surface of the skin to the lowest point in the wound at a second position in the wound corresponding to the second part of the image data and different from the first position.

Some embodiments of the present disclosure may include estimating at least one of an original position of a skin before a formation of the wound or a future position of the skin after healing of the wound by analyzing the 3D information, wherein the provided data may be based on at least one of the estimated original position of the skin or the future position of the skin. Estimating an original position of a skin before a formation of the wound may refer to estimating an outline of the skin in the affected area where the wound is currently before the wound appeared. A future position of the skin after healing of the wound may refer to an estimate of an outline of the skin in the affected area after the wound is cured. In some examples, a machine learning model (for example, a generative model, such as a generative adversarial network, a transformers based model, etc.) may be trained using training examples to determine original positions of the skin and/or future positions of the skin from 3D information of wounds. An example of such training example may include sample 3D information of a sample wound, together with a desired estimation of the original position of the skin and/or future position of the skin corresponding to the sample wound, for example in as a function assigning an original position of the skin and/or a future position of the skin for each position (and/or pixel) of the sample wound, as an overlay in an image of the sample wound (such as an image of a cross section view of the sample view), and so forth. The trained machine learning model may be used to analyze the 3D information and determine the original position of the skin and/or future position of the skin. In some examples, the 3D information of the wound may compared with 3D information of a symmetrical body part and/or of a generic body part corresponding to the body part associated with the wound, and the original position of the skin and/or future position of the skin may be selected to mimic the symmetrical body part and/or the generic body part. In some examples, the 3D information may include a 3D image of the wound, the area of the wound may be removed from the 3D image (for example using a semantic segmentation algorithm), and an inpainting algorithm may analyze the 3D with the wound removed to generate a 3D image of the original position of the skin and/or future position of the skin. In some embodiments, the data provided configured to cause a presentation of the generated cross section view of the wound may be based on at least one of the estimated original position of the skin or the estimated future position of the skin. In some embodiments, at least one of estimating the original position of the skin or estimating the future position of the skin may include implementing an inpainting algorithm based on the 3D information. An inpainting algorithm may refer to an algorithm which may fill in missing parts of an image to present a complete image. An inpainting algorithm may be implemented to "fill in," or estimate, original and future positions of the skin over the wound. The inpainting algorithm may be trained using image data from previous wounds, including images from before the wound, during different stages of the wound's healing, and after the wound has healed. By way of example, FIG. 7 illustrates an example of an estimated original position of the skin 760 and an estimated future position of the skin 770.

In some embodiments, the wound may correspond to a first body part of a patient, the patient having a symmetrical body part to the first body part, and wherein at least one of estimating the original position of the skin or estimating the future position of the skin may include receiving 3D information of the symmetrical body part and analyzing the 3D information of the symmetrical body part and the 3D information of the wound. A body part of a patient may refer to any part of a human being suffering from a wound such as an organ or an extremity. A symmetrical body part to the first body part may refer to a body part which is the counterpart of the body part suffering from the wound. For instance, if the wound corresponds to a patient's hand, the symmetrical body part to the first body part may be the patient's other, healthy hand. Similarly, if the wound corresponds to a patient's nose, and if the wound is present on one side of the nose, the symmetrical body part may correspond to the other, healthy side of the nose. By way of example, estimating original position of the skin 760 and/or the future position of the skin 770 may include receiving 3D information via mobile communications device 115 of a symmetrical body part to the body part wound 500 is located. For instance, if wound 500 is located on a forearm, a user may capture one or more images and/or videos using mobile communications device 115 of the same area of the counterpart healthy forearm and send the one or more images and/or videos to server 145 for analysis.

In some embodiments, the provided data may include a depth of the wound estimated based on at least one of the estimated original position of the skin or the estimated future position of the skin. For instance, the depth of the wound may be estimated by calculating the distance between the lowest point in the wound and the surface of the skin in the estimated original position of the skin or the estimated future position of the skin. The height of the surface of the skin compared to the lowest point in the wound may be different with respect to the estimated original position of the skin and the estimated future position of the skin, as scarring of the skin following healing of the wound may cause the skin to appear different. By way of example, FIG. 7 illustrates a wound depth 762 corresponding to "X mm" when calculated based on estimated original position of the skin 760 and a wound depth 772 corresponding to "Y mm" when calculated based on estimated future position of the skin 770.

In some embodiments, the generated cross section view of the wound may include a visual indication of at least one of the original position of the skin or the future position of the skin. For example, the generated cross section view of the wound may include an outline or some other indication showing the original position of the skin and/or the future position of the skin over the wound. By way of example, FIG. 7 includes outlines 760 and 770 depicting the original position of the skin and the future position of the skin over wound 500, respectively.

Figure 11:
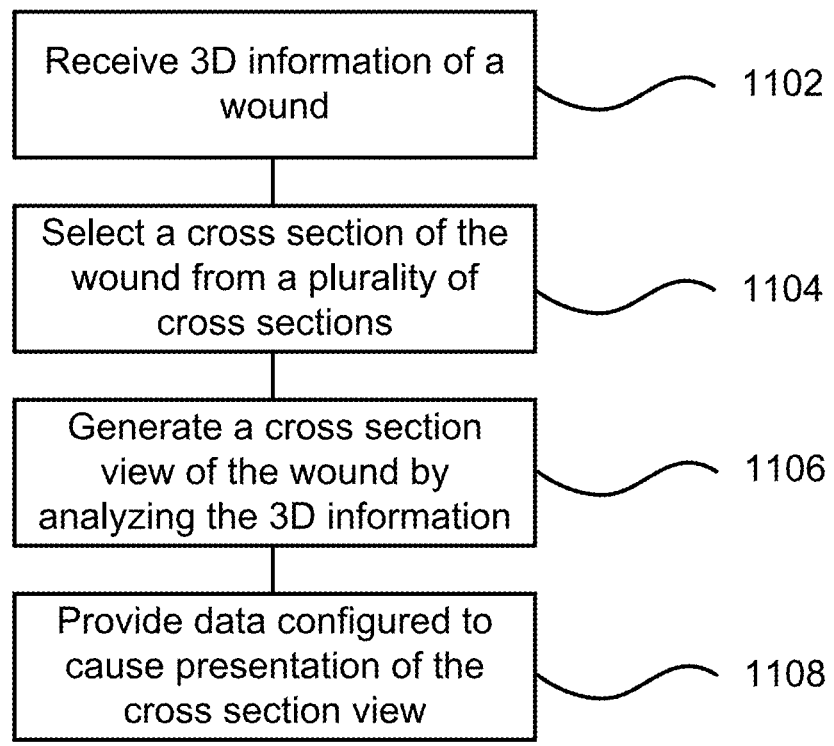
FIG. 11 is a flowchart of an example process for generating cross section views of a wound, consistent with some embodiments of the present disclosure.

FIG. 11 provides a flowchart of an example process 1100 for generating cross section views of a wound including steps 1102 through 1108. Steps 1102 through 1108 may be executed by at least one processor (e.g., processing device 202 of server 145 or mobile communications device 115 of FIG. 2), consistent with some embodiments of the present disclosure.

Process 1100 may begin with step 1102. At step 1102, the at least one processor may receive 3D information of a wound based on information captured using an image sensor (e.g., image sensor 226 of FIG. 2) associated with an image plane substantially parallel to the wound. The image sensor may be associated with a mobile device, such as communications device 115 of FIG. 2.

Once the 3D information is received, process 1100 may proceed to step 1104. At step 1104, the at least one processor may select a cross section of the wound from a plurality of cross sections. The selection of the cross section of the wound may be based on a plurality of factors. These factors may include, for example, the 3D information, a boundary contour of the wound, and a segmentation of the wound based on tissue type.

At step 1106, the at least one processor may generate a cross section view of the wound by analyzing the received 3D information, the cross section view of the wound corresponding to the selected cross section. For instance, if the at least one processor selected a cross section of the wound corresponding to the deepest point of the wound based on the 3D information, the at least one processor, at step 1106, may generate a cross section view of the wound corresponding to this selected cross section.

Once the cross section view has been generated, process 1100 may proceed to step 1108. At step 1108, the at least one processor may provide data configured to cause a presentation of the generated cross section view of the wound (e.g., to mobile communications devices 115, 125, and/or 165, or to server 145, which may include a display or may reroute the data to an appropriate display).

Figure 12:
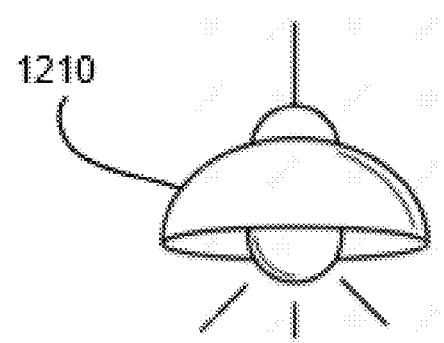
FIG. 12 is an illustration of a mobile communications device capturing an image, consistent with some embodiments of the present disclosure.
Figure 12:
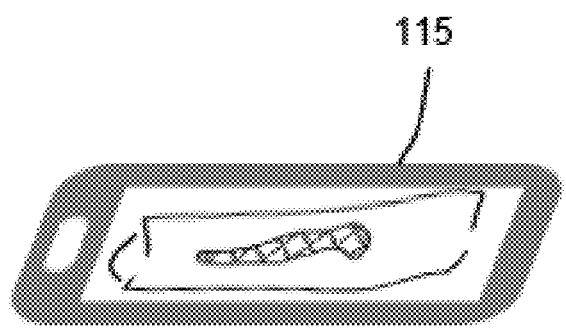
Figure 12:
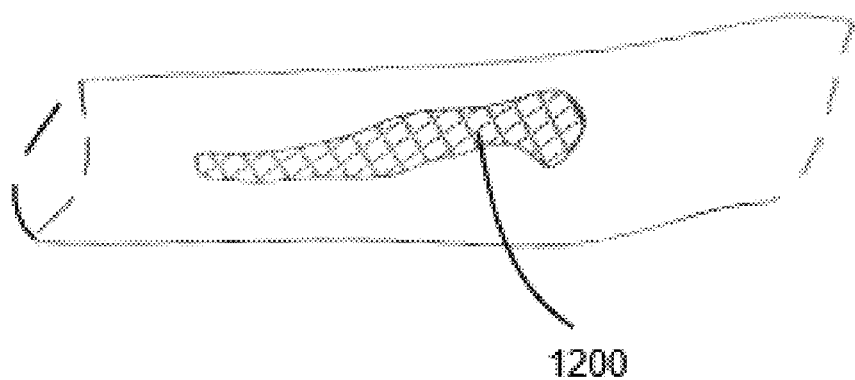

Aspects of this disclosure may relate to systems, methods, devices, and computer readable media storing instructions for analyzing wounds using standard user equipment. As used herein, a wound may include any injury to the human body. For example, wounds may be open wounds resulting from penetration (e.g., puncture wounds, surgical wounds and incisions, thermal, chemical, or electric burns, bites and stings, gunshot wounds, etc.) and/or blunt trauma (e.g., abrasions, lacerations, skin tears), or they may include closed wounds (e.g., contusions, blisters, seromas, hematomas, crush injuries, etc.). Some non-limiting examples of a wound may include a chronic wound, acute wounds, ulcer (such as venous ulcer, arterial ulcer, diabetic ulcer, pressure ulcer, etc.), infectious wound, ischemic wound, surgical wound, radiation poisoning wound, and so forth. As used herein, standard user equipment may refer to any portable device with image capturing capabilities that can communicate with a remote server over a wireless network. Examples of standard user equipment may include smartphones, tablets, smartwatches, smart glasses, wearable sensors and other wearable devices, wireless communication chipsets, personal digital assistants, and any other portable pieces of communications equipment. It should be noted that the terms "standard user equipment," "user equipment," "handheld mobile communications device," "handheld mobile device," "mobile communications device," and "mobile device" may be used interchangeably herein and may refer to any of the variety of devices listed above. By way of example, server 145 of FIGS. 1A and 2 may be configured to analyze a wound 1200 shown in FIG. 12.

Embodiments of the present disclosure may include receiving one or more images of a wound of a patient. In some embodiments, one or more images may be received via a wired or wireless transmission from an external device, such as a mobile communications device, as described in greater detail herein. In some other examples, receiving the one or more images may include reading the one or more images from memory, capturing the one or more images using an image sensor, receiving the one or more images from at least one image sensor of a mobile device, and so forth. The one or more images of a wound of a patient may include pictures taken of a patient suffering from a wound, each of the pictures including at least a portion of the wound, and/or an area of interest for examination of the wound, such as a healthy area surrounding the wound or a symmetrical body part to the body part suffering from the wound. By way of example, server 145 of FIG. 2 may receive one or more images of wound 1200 of FIG. 12 captured by image sensor 226 of mobile communications device 115 via communications network 150 of FIG. 1A.

Figure 15:
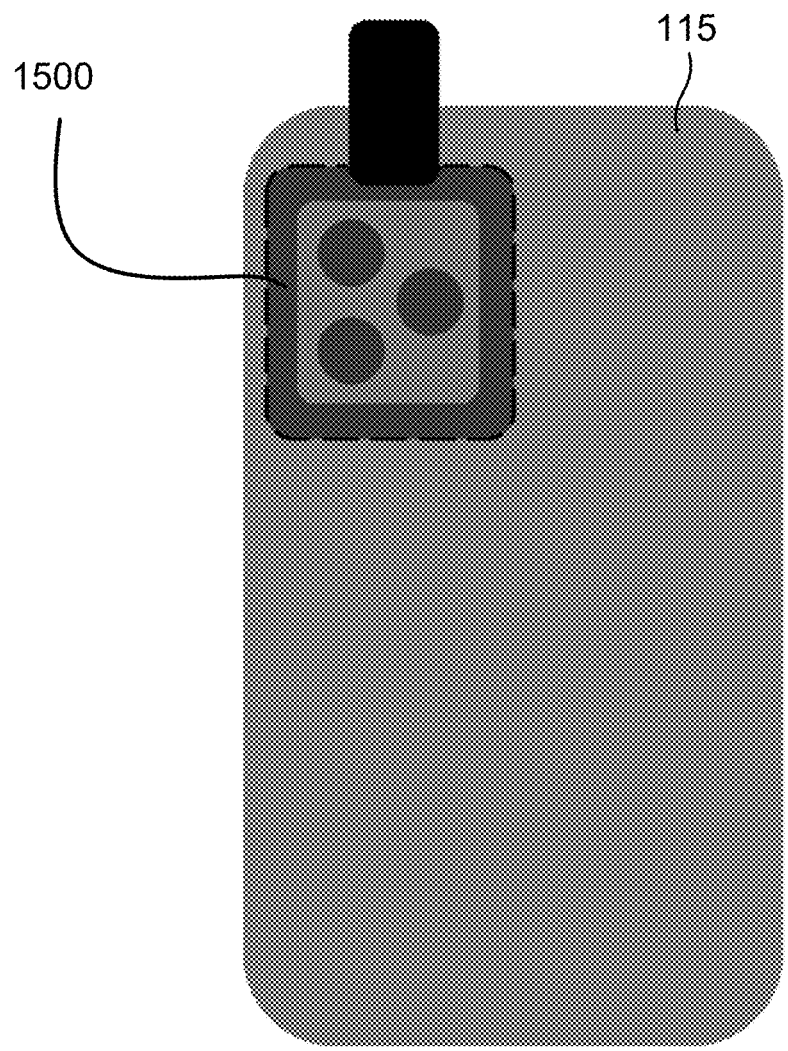
FIG. 15 is an illustration of a physical optical filter affixed to a standard mobile communications device, consistent with some embodiments of the present disclosure.

In some embodiments, the one or more images may be and/or include one or more images captured under artificial ultra-violet light, may be and/or include one or more images captured under artificial infrared light, and/or may be and/or include one or more images captured using a selected physical optical filter. Artificial ultra-violet light may refer to electromagnetic radiation in the ultra-violet range produced by an artificial source such as black lights, curing lamps, germicidal lamps, mercury vapor lamps, halogen lights, high-intensity discharge lamps, fluorescent and incandescent sources, lasers, and/or any other man-made sources of ultra-violet radiation. Artificial infrared light may refer to electromagnetic radiation in the infrared range produced by an artificial source such as electrical appliances, incandescent bulbs, radiant heaters, and/or any other man-made source of infrared radiation. A selected physical optical filter may refer to a device which may selectively transmit light of different wavelengths, as discussed in greater detail herein. By way of example, one or more images may be captured by mobile communications device 115 under a light 1210 which may be, for example, an artificial ultra-violet light, an artificial infrared light, or a standard light. The one or more images may be captured using a selected physical optical filter 1500, as shown in FIG. 15 and discussed in greater detail below.

Figure 13A:
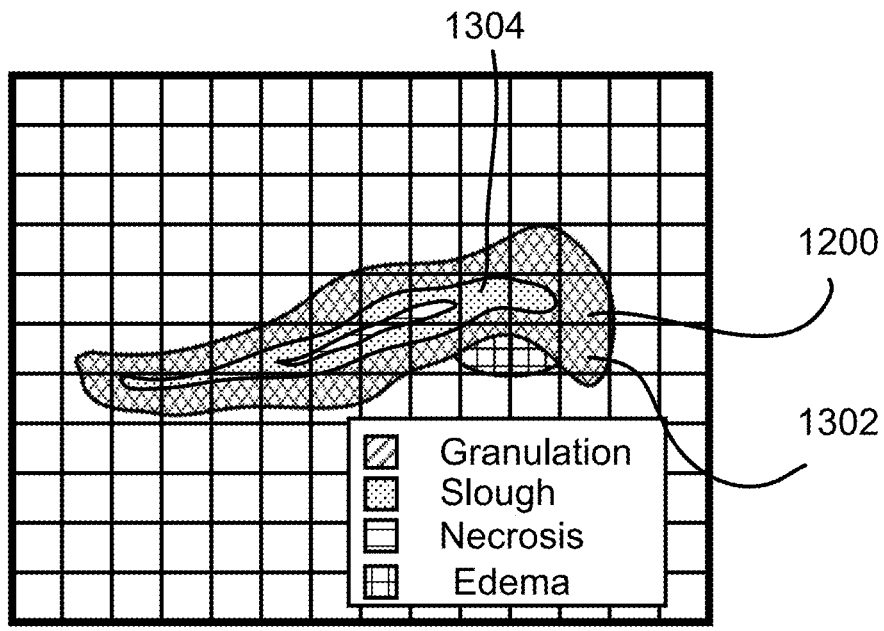
FIG. 13A is an illustration of an infected wound segmented into pixels, consistent with some embodiments of the present disclosure.
Figure 13B:
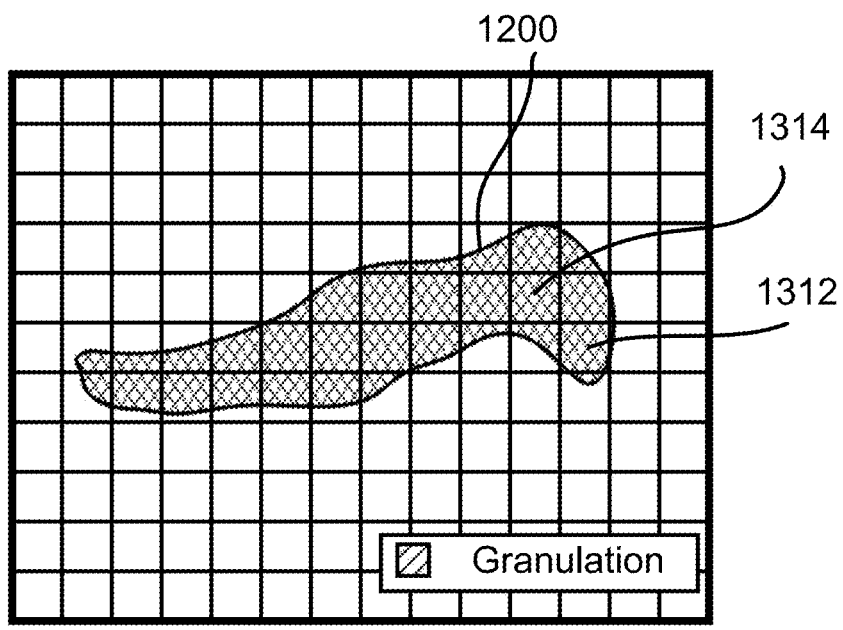
FIG. 13B is an illustration of a healthy wound segmented into pixels, consistent with some embodiments of the present disclosure.

Embodiments of the present disclosure may include analyzing the one or more images (for example as described above) to determine a condition of the wound. In one example, a machine learning model may be trained using training examples to determine conditions of wounds from images. An example of such training example may include a sample image of a sample wound, together with a label indicating the condition of the sample wound. The trained machine learning model may be used to analyze the one or more images to determine the condition of the wound. In another example, a visual classification algorithm may classify the one or more images to one of a plurality of alternative classes, and each class may correspond to a different condition of the wound. In some examples, the embodiments of the present disclosure may include analyzing the one or more images to determine, based on at least a difference between values of two pixels of the one or more images, a condition of the wound. A pixel may refer to the smallest unit of a digital image or graphic which may be displayed and represented on a digital display device. A difference between values of two pixels may refer to a difference in the coloration of the two pixels, for instance, a difference in RGB color values of each pixel. A condition of a wound may refer to the state of the wound, for instance, if the wound is infected, clean, healing adequately, fully or partially healed, showing signs of heat, redness, swelling, or any other physical state a wound may be in. In one example, a numerical value representing a different between the values of two pixels (for example, difference in intensity, difference in a particular color component, or another difference) may be determined by comparing the values of the two pixels. Further, in response to a first determined numerical value, a first condition of the wound may be determined, and in response to a second determined numerical value, a second condition of the wound may be determined, the second condition may differ from the first condition. In some examples, a machine learning model may be trained using training examples to determine a condition of a wound from a difference between values of two pixels. An example of such training example may include a sample difference between two pixels of a sample image of a sample wound, together with a label indicating the condition of the sample wound. The trained machine learning model may be used to analyze the difference between the values of the two pixels to determine the condition of the wound. In one example, the condition of a wound may be determined based on a difference between values of two pixels by, for example, determining that a value of one pixel represents a healthy portion of a wound and comparing said value of the pixel to a value of another pixel of the wound, which may correspond to a non-healthy portion of the wound. By way of example, FIGS. 13A and 13B illustrate a captured image of wound 1200 segmented into pixels. The values of the illustrated pixels may be compared, and a difference between the RGB values may indicate the condition of wound 1200. For instance, a difference between the values of pixels 1302 and 1304, as shown in FIG. 13A, may indicate that a wound is infected. Alternatively, a difference between the values of pixels 1312 and 1314, as shown in FIG. 13B, may indicate that a wound is healing adequately.

In some embodiments, an indication of a past condition of the wound at a particular time period may be received. The particular time period may be at least one day before the capturing of the one or more images of the wound. In other examples, the particular time period may be at least one hour, at least two hours, at least one day, at least two days, at least a week, etc., before the capturing of the one or more images of the wound. In some examples, receiving the indication of the past condition of the wound may include at least one of reading the indication from memory, receiving the indication from an external device, receiving the indication from a user (for example through a user interface), generating the indication (for example by analyzing images of the wound captured at the particular time period), and so forth. In some examples, images of the wound captured at the particular time period may be analyzed to determine the past condition of the wound at the particular time period, for example as described above in relation to the analysis of the one or more images to determine the condition of the wound. In some embodiments, the determination of the condition of the wound may be based on the past condition of the wound and the analysis of the one or more images. For example, when the condition of the wound determined by the analysis of the one or more images is incompatible with the past condition of the wound, further processing may be made to correct the determination of the condition of the wound. In another example, the past condition of the wound may be used to determine a prior probabilities for the condition of the wound, for example using a Markov model, and the determination of the condition of the wound based on the analysis of the one or more images may be further based on the prior probabilities. In some examples, a machine learning model may be trained using training examples to determine conditions of wounds from images of the wounds and from past conditions of the wounds. An example of such training example may include a sample image of a sample wound and a sample indication of a past condition of the sample wound, together with a label indicating the condition of the sample wound. The trained machine learning model may be used to analyze the one or more images and the indication of the past condition of the wound to determine the condition of the wound.

Embodiments of the present disclosure may include selecting an action based on the determined condition of the wound and initiating the selected action. In some examples, the action may include at least one of processing the one or more images, providing instructions to a user to capture at least one additional image of the wound, and/or providing particular information associated with the condition of the wound. Processing the one or more images may include any image analysis techniques, including the image analysis techniques discussed above. Particular information associated with the condition of the wound may include any data that may provide a user with information regarding the condition of the wound, for instance, text describing the condition of the wound or a visual representation of the wound with indications of the condition of the wound in different areas. Selecting an action based on the determined condition of the wound may refer to choosing one or more actions from a plurality of actions based on the condition of the wound. For instance, if a wound is determined to have a potentially infected area, an action may be selected that instructs a user to capture at least one additional image of the affected area of the wound. In one example, initiating the selected action may refer to causing a device (for example, the device selecting the action, the device analyzing the one or more images to determine the condition of the wound, an external device, and so forth) to perform the selected action and/or providing a device with instructions relating to the action. In another example, initiating the selected action may include causing a user to perform the action, for example by providing the user with instructions and/or recommendations to perform the action (for example visually, audibly, textually, graphically, through a user interface, and so forth).

Figure 14:
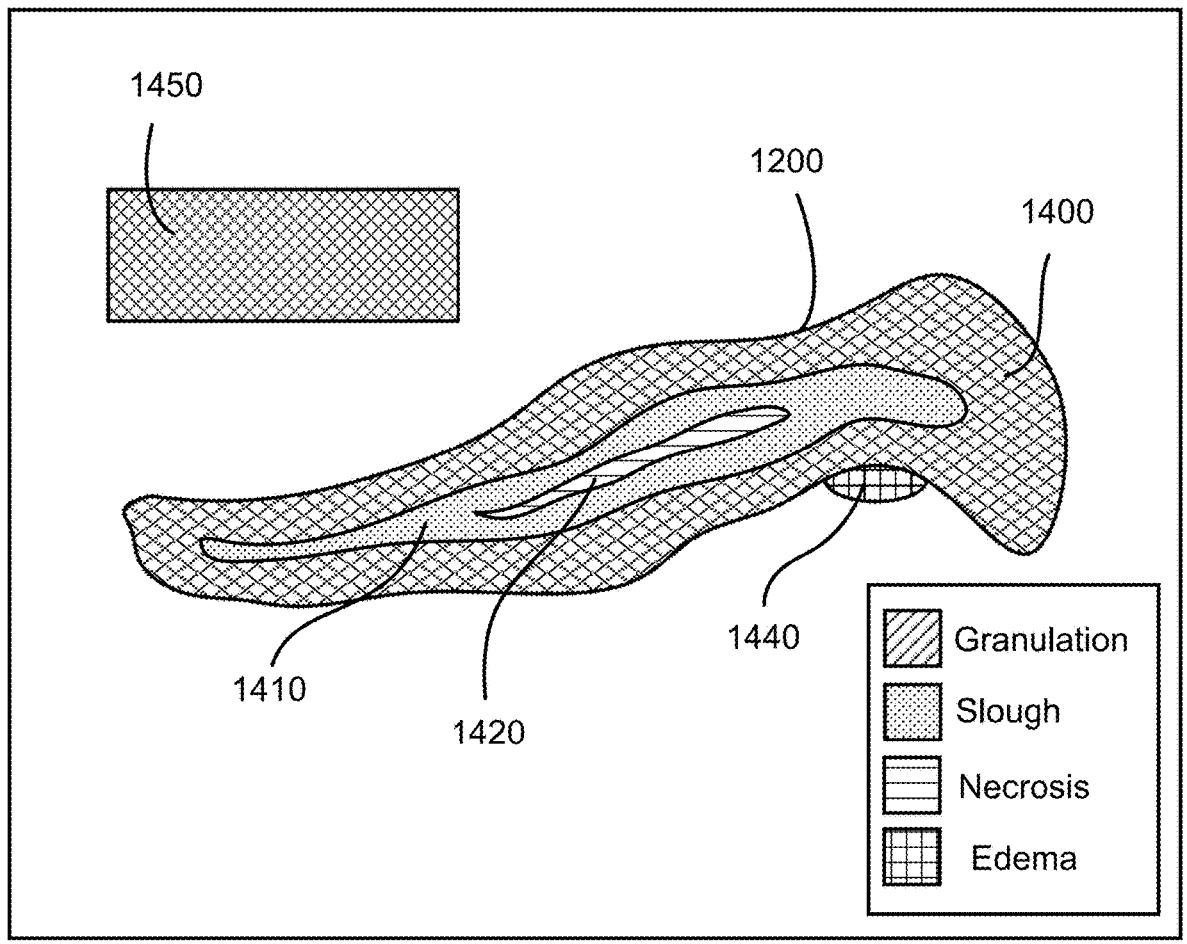
FIG. 14 is an illustration of an infected wound with a calibration element, consistent with some embodiments of the present disclosure.

Embodiments consistent with the present disclosure may include analyzing the one or more images to determine at least one of a shape of the wound, a tissue composition of the wound, a depth of the wound, or a presence of an edema in a region surrounding the wound, and wherein the determination of the condition of the wound may be further based on the determined at least one of the shape of the wound, the tissue composition of the wound, the depth of the wound, or the presence of the edema in the region surrounding the wound. A shape of the wound may refer to a 2D or 3D form made by the wound on the body of a patient. A tissue composition of the wound may refer to a segmentation of the wound based on a tissue type, such as epithelial tissue, granulation tissue, slough tissue, eschar, necrotic tissue, scab, hematoma, tendon, ligament, bone, infected tissue, non-infected tissue, or any other type of tissue which may be found in a wound. A depth of the wound may refer to the distance between a point along the bottom of a wound and one of the surface of the skin surrounding the wound, an estimated original position of the skin, or an estimated future position of the skin. An edema may refer to swelling caused by fluid trapped in the patient's tissues. By way of example, image 1400, as depicted in FIG. 14, may be analyzed to determine a shape of wound 1200, a tissue composition of wound 1200 (e.g., granulation tissue 1410, slough tissue 1420, and necrosis tissue 1430), a depth of wound 1200, and/or a presence of an edema in a region surrounding wound 1200, such as edema 1440.

In some embodiments, the one or more images may include at least a first image and a second image, the first image being an image captured using a first physical optical filter and the second image being an image captured using a second physical optical filter, wherein the second physical optical filter may differ from the first physical optical filter and the determination of the condition of the wound may be further based on an analysis of the first image and the second image. A condition of the wound may be determined based on an analysis of the first image and the second image due to information combined from the two images. For example, the first physical optical filter may enable the capturing of visible colors in the first image, and the second physical optical filter may enable the capturing of infrared light in the second image. Combining the color information from the first image and temperature data associated with the wound from the second image may enable a more accurate determination of the condition of the wound in comparison to the usage of any single one of the two images. In some examples, a machine learning model may be trained using training examples to determine conditions of wounds from pairs of images captured using different physical optical filters. An example of such training example may include one sample image of a sample wound captured using one physical optical filter and another sample image of the sample wound captured using another physical optical filter, together with a label indicating the condition of the sample wound. The trained machine learning model may be used to analyze the first image and the second image to determine the condition of the wound. By way of example, the one or more images may include at least a first image captured using physical optical filter 1500 and at least a second image captured using a different physical optical filter.

In some embodiments, the one or more images may include at least one image depicting at least part of the wound and a calibration element, the calibration element including a form of a known size, a known shape, and/or a known color. In some embodiments, the determination of the condition of the wound may be based on at least one of the known size, the known shape, or the known color of the calibration element. A calibration element may refer to an object that may be captured with at least a portion of a wound in an image and may be used to ascertain a size, shape, and/or color of the at least a portion of the wound. A size, shape, and/or color of the calibration element may be known such that a size, shape, and/or color may be determined for the at least a portion of the wound. By way of example, image 1400 of FIG. 14 depicts a calibration element 1450, which may have a known size, shape, and color, and which may be used to determine the size, shape, and/or color of at least a portion of wound 1200. Another example of a calibration element, as depicted in FIG. 4A, may include colorized surface 132 and/or elements 405 and/or 410 of colorized surface 132, and the image may depict colorized surface 132 and wound 400.

In some embodiments, the one or more images may include one or more images of the wound captured using a mobile communications device. Embodiments consistent with the present disclosure may include causing the mobile communications device to provide an instruction to a user of the mobile communications device to capture an image of the wound without a physical optical filter, to place a physical optical filter on the mobile communication device, and to capture an image of the wound with the physical optical filter. A physical optical filter may be attached to a mobile communications device to manipulate light reaching a camera included in the mobile communications device. The physical optical filter may be shaped to envelop at least one corner of the mobile communications device while covering the camera and may include an adhesive side configured to attach the physical optical filter to the mobile communications device. By way of example, the one or more images may include one or more images of wound 1200 captured using mobile communications device 115. In some embodiments, mobile communications device 115 may provide an instruction to a user to capture an image of wound 1200 without a physical optical filter, then place physical optical filter 1500, as depicted in FIG. 15, on mobile communications device 115, and capture an image of wound 1200 with physical optical filter 1500 placed on mobile communications device 115.

Embodiments consistent with the present disclosure may include receiving and analyzing the image of the wound captured without the physical optical filter and the image of the wound captured with the physical optical filter to determine the condition of the wound. The condition of the wound may be determined from the image of the wound captured without the physical optical filter and the image of the wound captured with the physical optical filter, for example by combining information combined from the two images. For example, the image of the wound captured without the physical optical filter may include visible colors, and the image of the wound captured with the physical optical filter may include infrared data. Combining the color information from the image of the wound captured without the physical optical filter and temperature data associated with the wound from the infrared data may enable a more accurate determination of the condition of the wound in comparison to the usage of any single one of the two images. In some examples, a machine learning model may be trained using training examples to determine a conditions of wounds from pairs of images, each pair may include an image captured with a physical optical filter and an image captured without a physical optical filter. An example of such training example may include one sample image of a sample wound captured without a physical optical filter and another sample image of the sample wound captured using a physical optical filter, together with a label indicating the condition of the sample wound. The trained machine learning model may be used to analyze the image of the wound captured without the physical optical filter and the image of the wound captured with the physical optical filter to determine the condition of the wound.

Embodiments consistent with the present disclosure may include causing the mobile communications device to provide an instruction to the user to place a calibration element in proximity to the wound, the calibration element including a form of a known size, a known shape, or a known color, and using at least one of the known size, the known shape, or the known color in the analysis of the image of the wound captured without the physical optical filter and the image of the wound captured with the physical optical filter. By way of example, mobile communications device 115 may provide an instruction to a user to place calibration element 1450 near wound 1200 to capture both calibration 1450 and wound 1200 in the same image, such as in image 1400.

Embodiments consistent with the present disclosure may include analyzing the one or more images to determine that an urgency level associated with the wound is a first level of urgency and, in response to the determination that the urgency level associated with the wound is the first level of urgency, initiating a particular action. An urgency level associated with the wound may refer to a degree to which a state of the wound requires immediate action or attention. For instance, for a determination that a wound requires immediate attention to prevent further damage, a first level of urgency may be given to the wound. Then, in response to the determination that a first level of urgency has been given to the wound, a particular action may be initiated, for example, the particular action may be configured to cause an advancement of the patient in an order of treatment. That is, a patient may be given treatment in advance of other patients with a lower level of urgency. On the other hand, a wound which does not require immediate attention or less attention may be given a second, third, fourth, or any other appropriate level of urgency. By way of example, a first level of urgency may be determined for wound 1200 due to the presence of slough tissue 1420, necrosis tissue 1430, and/or edema 1440, and a particular action may be initiated, such as advancing the patient in an order of treatment.

In some embodiments, the one or more images may include at least a first image and a second image, the first image being an image captured at least one day before a capturing of the second image, wherein the determination that the urgency level associated with the wound is the first level of urgency may be based on a comparison of the wound in the first image with the wound in the second image, and wherein the particular action may be initiated within one hour of the capturing of the second image. For instance, if a comparison of the wound in the first image and the wound in the second image shows that the wound is deteriorating rapidly, a higher level of urgency may be given to the wound to initiate a particular action sooner. By way of example, a patient may capture an image of wound 1200 on a particular day, and on the next day capture an image of wound 1200, which shows that the wound has developed slough and necrosis tissue and an edema, and accordingly determine a first level of urgency should be assigned to wound 1200.

Embodiments consistent with the present disclosure may include determining that a confidence level associated with the determined condition of the wound is a first confidence level and, in response to the determination that the confidence level associated with the determined condition of the wound is the first confidence level, avoiding initiating the selected action. A confidence level may refer to a degree of certainty that a determined condition of the wound is accurate. For instance, for a given determined condition of a wound which is determined to accurately reflect the actual condition of the wound, a first confidence level may be associated with the determined condition of the wound such that a selected action may not be initiated as no more information on the wound may be needed. Alternatively, for a determined condition of a wound which may not accurately reflect the actual condition of the wound, a second, third, fourth, or any other appropriate confidence level may be associated with the condition of the wound such that the selected action may be initiated, as more information on the wound may be needed.

Figure 16:
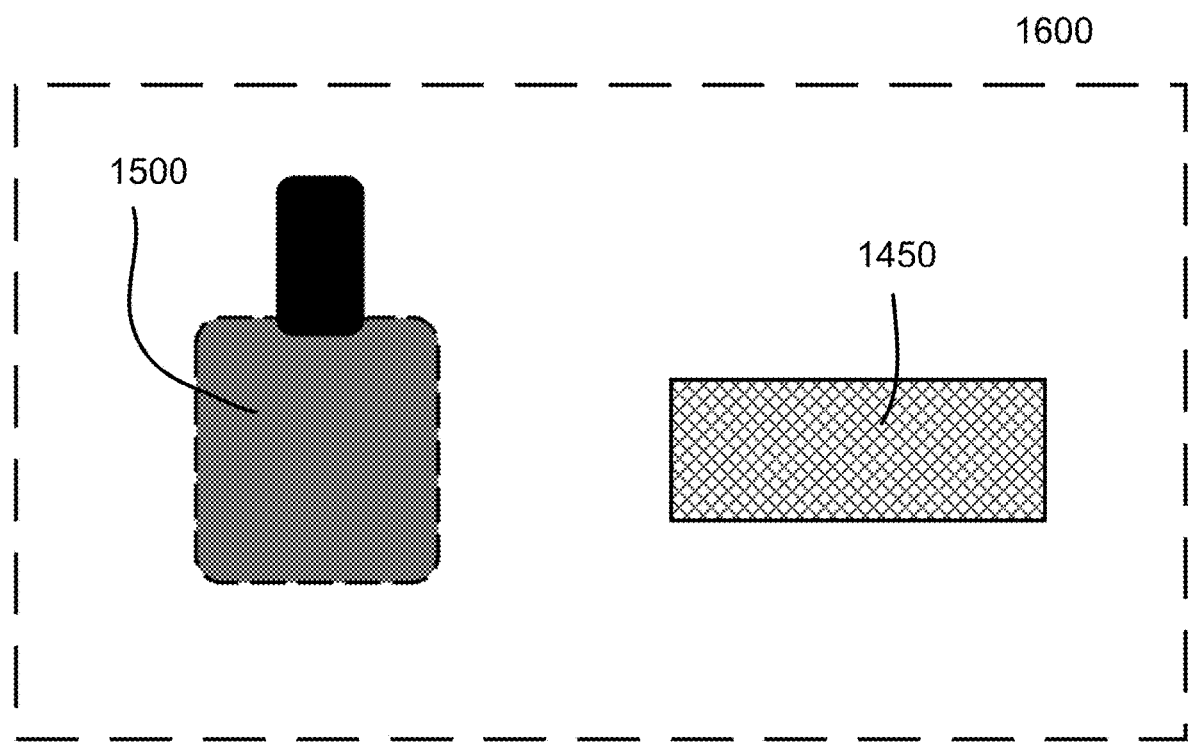
FIG. 16 is an illustration of a kit including a physical optical filter and a calibration element, consistent with some embodiments of the present disclosure.

Aspects of this disclosure may relate to a kit for facilitating capturing of medical images. In some embodiments, the kit may include a physical optical filter configured to be selectively attached to a standard user mobile communications device and to manipulate light reaching a camera included in the standard user mobile communications device when attached to the standard user mobile communications device. As used herein, a kit may refer to a set of articles or equipment needed for a specific purpose. A physical optical filter may refer to a device which may selectively transmit light of different wavelengths. In some embodiments, the physical optical filter may be shaped to envelop at least one corner of the standard user mobile communications device while covering the camera included in the standard user mobile communications device. In some embodiments, the physical optical filter may include an adhesive side configured to attach the physical optical filter to the standard user mobile communications device. By way of example, a kit 1600, as depicted in FIG. 16, may include physical optical filter 1500 which may be affixed onto mobile communications device 115.

Consistent with disclosed embodiments, the kit may include a calibration element, the calibration element including a form of a known size, a known shape, and a known color. A calibration element may refer to an object which may be captured with at least a portion of a wound in an image and may be used to ascertain a size, shape, and/or color of the at least a portion of the wound. A size, shape, and/or color of the calibration element may be known such that a size, shape, and/or color may be determined for the at least a portion of the wound. By way of example, kit 1600 may include calibration element 1450, which includes a known size, shape, and color to aid in the calibration of an image. Another example of a calibration element may include colorized surface 132, as depicted in FIGS. 4A and 4B.

In some embodiments, the physical optical filter may be configured to enable capturing of at least two medical images of a wound by the camera included in the standard user mobile communications device, including capturing at least one image using the physical optical filter and capturing at least one image without the physical optical filter. In some embodiments, the calibration element may be configured to enable color calibration of the at least one image captured using the physical optical filter and to enable calibration of the at least one image captured without the physical optical filter. For instance, a physical optical filter may be completely or partially removable such that a camera included in the standard user mobile communications device may capture at least one image using the physical optical filter and at least one image without the physical optical filter. Calibrating the images based on the calibration element may be performed due to the known color of the calibration element, which may be compared to surrounding colors in the captured images to determine their true colors and modify the captured images based on the determination.

Figure 17:
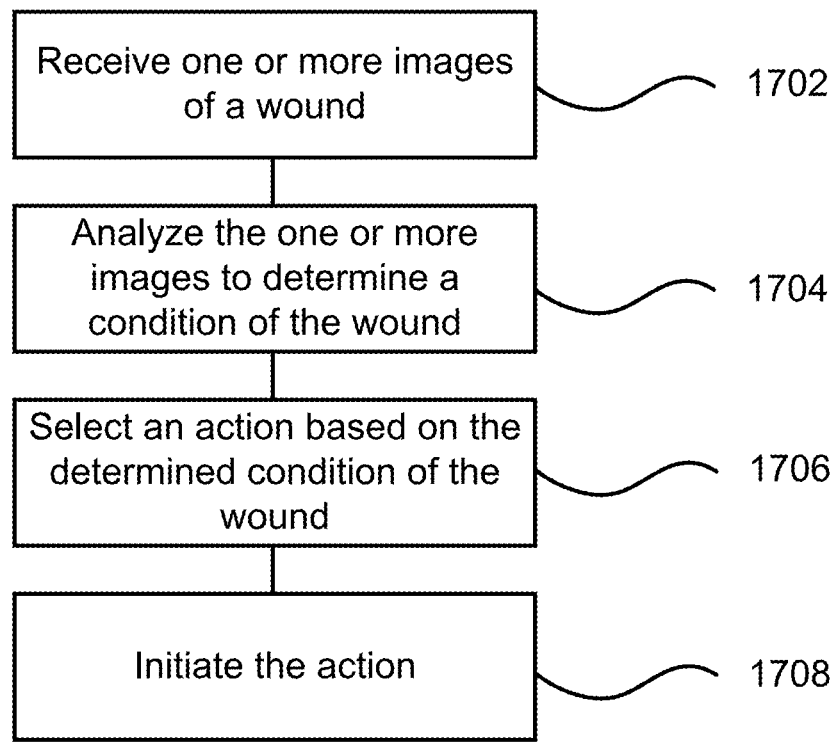
FIG. 17 is a flowchart of an example process for analyzing wounds using standard user equipment, consistent with some embodiments of the present disclosure.

FIG. 17 provides a flowchart of an example process 1700 for generating cross section views of a wound including steps 1702 through 1708. Steps 1702 through 1708 may be executed by at least one processor (e.g., processing device 202 of server 145 or mobile communications device 115 of FIG. 2), consistent with some embodiments of the present disclosure.

Process 1700 may begin with step 1702. At step 1702, the at least one processor may receive one or more images of a wound of a patient. By way of example, the one or more images may have been captured using image sensor 226 of FIG. 2 and sent by mobile communications device 115 to server 145.

Once the one or more images are received, process 1700 may proceed to step 1704. At step 1704, the at least one processor may analyze the one or more images to determine, based on at least a difference between values of two pixels of the one or more images, a condition of the wound.

At step 1706, the at least one processor may select an action based on the determined condition of the wound, wherein the selected action may include at least one of additional processing of the one or more images, providing instructions to a user to capture at least one additional image of the wound, and/or providing particular information associated with the condition of the wound. For instance, if the determined condition of the wound includes an area of the wound which is infected, the selected action may provide instructions to a user to capture at least one additional image of the affected area of the wound. Once the action has been selected, process 1700 may proceed to step 1708. At step 1708, the at least one processor may initiate the selected action.

Figure 18:
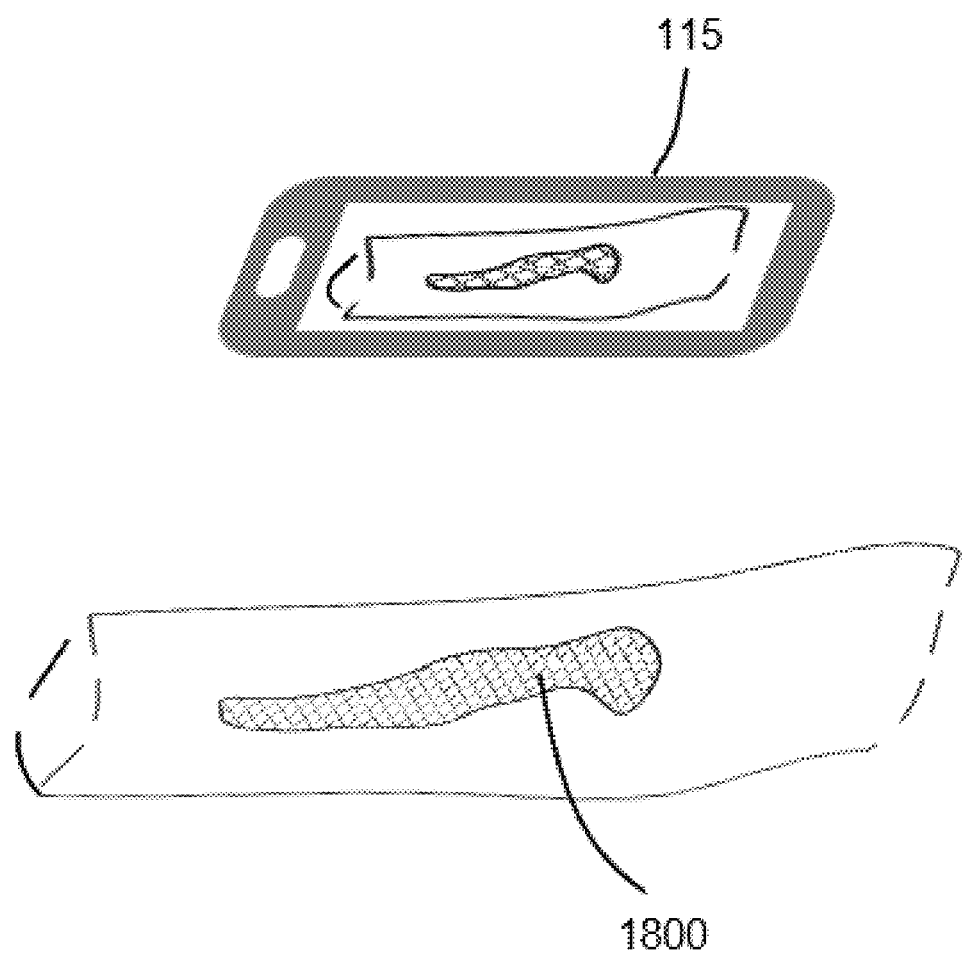
FIG. 18 is an illustration of a mobile communications device capturing an image or video of an example wound, consistent with some embodiments of the present disclosure.
Figure 23:
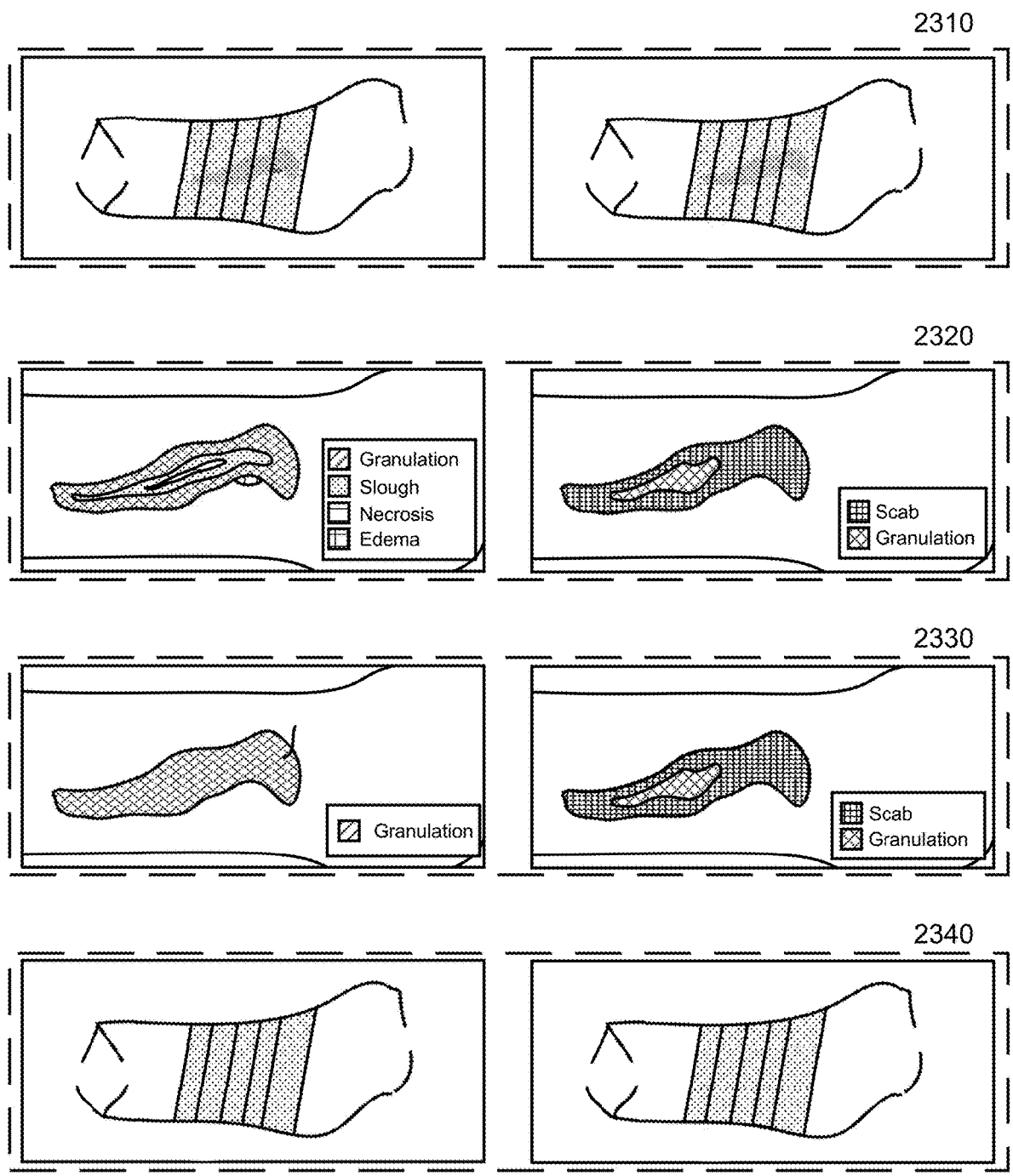
FIG. 23 is an illustration of visual time series views of a wound, consistent with some embodiments of the present disclosure.

Aspects of this disclosure may relate to systems, methods, devices, and computer readable media storing instructions for generating visual time series views of wounds. As used herein, a wound may include any injury to the human body. For example, wounds may be open wounds resulting from penetration (e.g., puncture wounds, surgical wounds and incisions, thermal, chemical, or electric burns, bites and stings, gunshot wounds, etc.) and/or blunt trauma (e.g., abrasions, lacerations, skin tears), or they may include closed wounds (e.g., contusions, blisters, seromas, hematomas, crush injuries, etc.). Some non-limiting examples of a wound may include a chronic wound, acute wounds, ulcer (such as venous ulcer, arterial ulcer, diabetic ulcer, pressure ulcer, etc.), infectious wound, ischemic wound, surgical wound, radiation poisoning wound, and so forth. A visual time series view may refer to a series of images or other visual representations ordered in time. By way of example, server 145 of FIGS. 1A and 2 may be configured to generate visual time series views 2300, 2310, 2320, and 2330 shown in FIG. 23 of a wound 1800, originally depicted in FIG. 18. According to embodiments disclosed herein, one or more images of wound 1800 may be captured by mobile communications device 115.

Embodiments of the present disclosure may include receiving at least a first image data record and a second image data record, the first image data record corresponding to a first point in time and including a first one or more images of a wound captured at the first point in time, and the second image data record corresponding to a second point in time and including a second one or more images of the wound captured at the second point in time. As used herein, an image data record may refer to a collection of related images or information related to the images. Each image data record may be associated with a point in time. For instance, a user of a standard mobile communications device may capture one or more images via a camera included in the mobile communications device at a particular point in time, and the image data record including the one or more images may correspond to said particular point in time. In one example, an image data record may be and/or include a video of a wound captured by a user using a standard mobile communications device, and the one or more images included in the image data record may be and/or include one or more frames of the video. For example, the video may be a video of the wound captured using the standard mobile communications device while the standard mobile communications device moves. In another example, the video may be a video of the wound captured while the wound is moving. In yet another example, the video may be a video of the wound captured using an image sensor included in the standard mobile communications device while at least one parameter of the image sensor changes (such as zoom, focus, and so forth). In an additional example, the video may be a video of the wound captured while the illumination conditions changes. As used herein, a standard mobile communications device may refer to any portable device with image capturing capabilities that can communicate with a remote server over a wireless network. Examples of standard user equipment may include smartphones, tablets, smartwatches, smart glasses, wearable sensors and other wearable devices, wireless communication chipsets, personal digital assistants, and any other portable pieces of communications equipment. It should be noted that the terms "standard user equipment," "user equipment," "handheld mobile communications device," "handheld mobile device," "mobile communications device," and "mobile device" may be used interchangeably herein and may refer to any of the variety of devices listed above. By way of example, server 145 of FIG. 2 may receive a first image data record 1900 of FIG. 19 and a second image data record 2000 of FIG. 20, first image data record 1900 corresponding to a first point in time and including four images 1910, 1920, 1930, and 1940 of wound 1800 captured at the first point in time, and second image data record 2000 corresponding to a second point in time and include four images 2010, 2020, 2030, and 2040 of wound 1800 captured at the second point in time. First image data record 1900 and second image data record 2000, depicted in FIG. 20, may be captured by the same device (such as mobile communications device 115), or by different devices.

In some embodiments, an image data record may be received via a wired or wireless transmission from an external device, such as a mobile communications device, as described in greater detail herein. In other examples, an image data record may be read from memory, may be captured using an image sensor, may be generated (for example, from images and/or videos), and so forth. An image data record of a wound of a patient may include pictures taken of a patient suffering from a wound, each of the pictures including at least a portion of the wound, and/or an area of interest for examination of the wound, such as a healthy area surrounding the wound or a symmetrical body part to the body part suffering from the wound. Additionally or alternatively, an image data record of a wound may include one or more videos of the wound and/or an area of interest for examination of the wound.

Embodiments of the present disclosure may include obtaining an image of the wound from a particular point of view corresponding to the first point in time by analyzing the first image data record. In some embodiments, the image of the wound from the particular point of view corresponding to the first point in time may be an image of the first one or more images of the wound. In such embodiments, obtaining an image of the wound from a particular point of view corresponding to the first point in time may include selecting an image of the wound from the first one or more images of the wound captured at the first point in time. Alternatively, the image of the wound from the particular point of view corresponding to the first point in time may be a simulated image of the wound based on the first image data record. Generating a simulated image of the wound based on an image data record is described in greater detail below. A particular point of view may refer to a view of the wound including a particular illumination, viewing angle, orientation, image plane, distance, coloration, and/or any other property of an image which may need to be controlled from one image to the next in a visual time series view of the wound for a medical practitioner to adequately examine the wound. By way of example, server 145 of FIG. 2 may obtain an image of wound 1800 from a particular point of view corresponding to the first point in time by analyzing image data record 1900 of FIG. 19. For instance, server 145 may select one of images 1910, 1920, 1930, and/or 1940 to generate a visual time series view of wound 1800.

In some embodiments, obtaining an image of a wound from a particular point of view corresponding to a first point in time may include analyzing images of the wound from other point of views corresponding to the first point in time to generate the image of the wound from the particular point of view corresponding to the first point in time. Similarly, obtaining an image of a wound from a particular point of view corresponding to a second point in time may include analyzing images of the wound from other points of view corresponding to the second point in time to generate the image of the wound from the particular point of view corresponding to the second point in time. For example, a machine learning model (for example, a generative model, such as generative adversarial network, transformers based generative model, etc.) may be trained using training examples to generate images of desired points of view based on images of other points of view. An example of such training examples may include a sample image of a sample wound from a sample point of view and an indication of the desired point of view, together with an image of the sample wound from the desired point of view. The trained machine learning model may be used to analyze at least one image of an image data record corresponding to one point in time (such as the first point in time or the second point in time) to generate an image of the wound from the particular point of view corresponding to the that point in time. In some other examples, the one or more images included in an image data record may include frames of a video of the wound, the particular point of view may correspond to a point of view in between two points of views corresponding to two consecutive frames of the video, and a video inpainting algorithm may be used to generate a new frame of the video between the two consecutive frames and corresponding to the particular point of view. In some other examples, images of an image data record may be used to populate a 3D tensor, where each specific image may populate a slice of the tensor corresponding to a point of view associated with the specific image, and interpolation algorithm may be used to complete a slice of the 3D tensor corresponding to the particular point of view, therefore generating the image of the wound from the particular point of view corresponding to the point in time associated with the image data record.

Embodiments of the present disclosure may include generating a simulated image of the wound from the particular point of view corresponding to the second point in time by analyzing the second image data record, wherein the second one or more images of the wound do not include an image of the wound from the particular point of view. In some embodiments, the second one or more images of the wound may not include an image of the wound from the particular point of view. In such embodiments, a simulated image of the wound from the particular point of view must be generated to be able to generate a visual time series view of the wound including the same particular view throughout the two or more included images. Analyzing the second image data record to generate the simulated image of the wound from the particular point of view corresponding to the second point in time may refer to selecting one or more images of the second one or more images of the wound which may be similar to the image of the wound from the particular point of view corresponding to the first point in time and extracting data from the selected one or more images such that a simulated image of the wound at the second point in time may be generated from the extracted data, the simulated image of the wound corresponding to the particular point of view. For instance, data may be extracted from the selected one or more images of the wound of the second one or more images of the wound such that a simulated image may be generated including a same particular illumination, viewing angle, orientation, image plane, distance, coloration, and/or other appropriate property as the image of the wound corresponding to the first point in time. To this effect, both the simulated image of the wound corresponding to the second point in time and the image of the wound corresponding to the first point in time may share a particular point of view, even though no image of the second one or more images shared the particular point of view of the image of the wound corresponding to the first point in time. In other examples, the second image data record may be analyzed to generate the simulated image of the wound from the particular point of view corresponding to the second point in time as described above.

Figure 20:
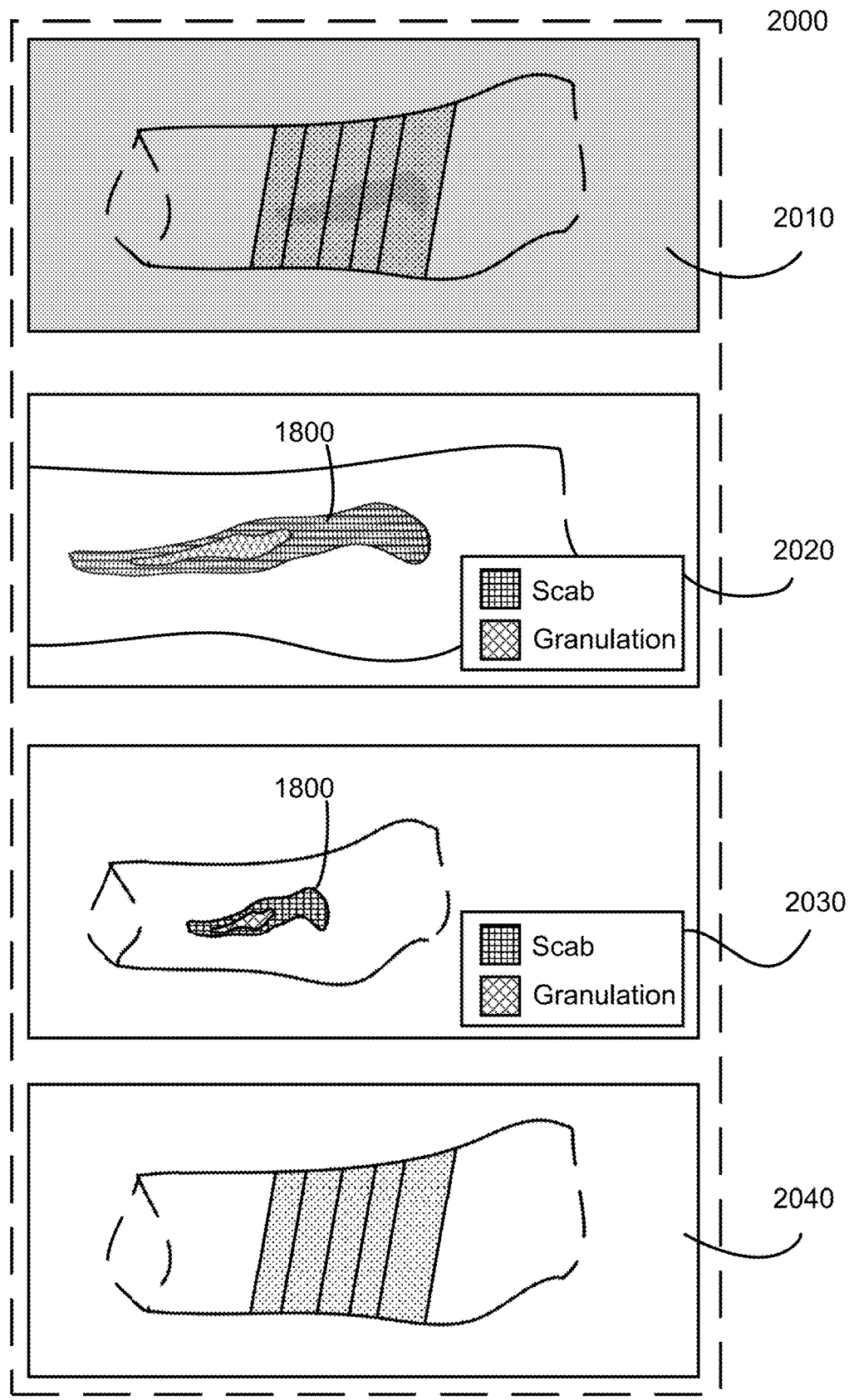
FIG. 20 is an illustration of an image data record corresponding to a second point in time, consistent with some embodiments of the present disclosure.
Figure 21:
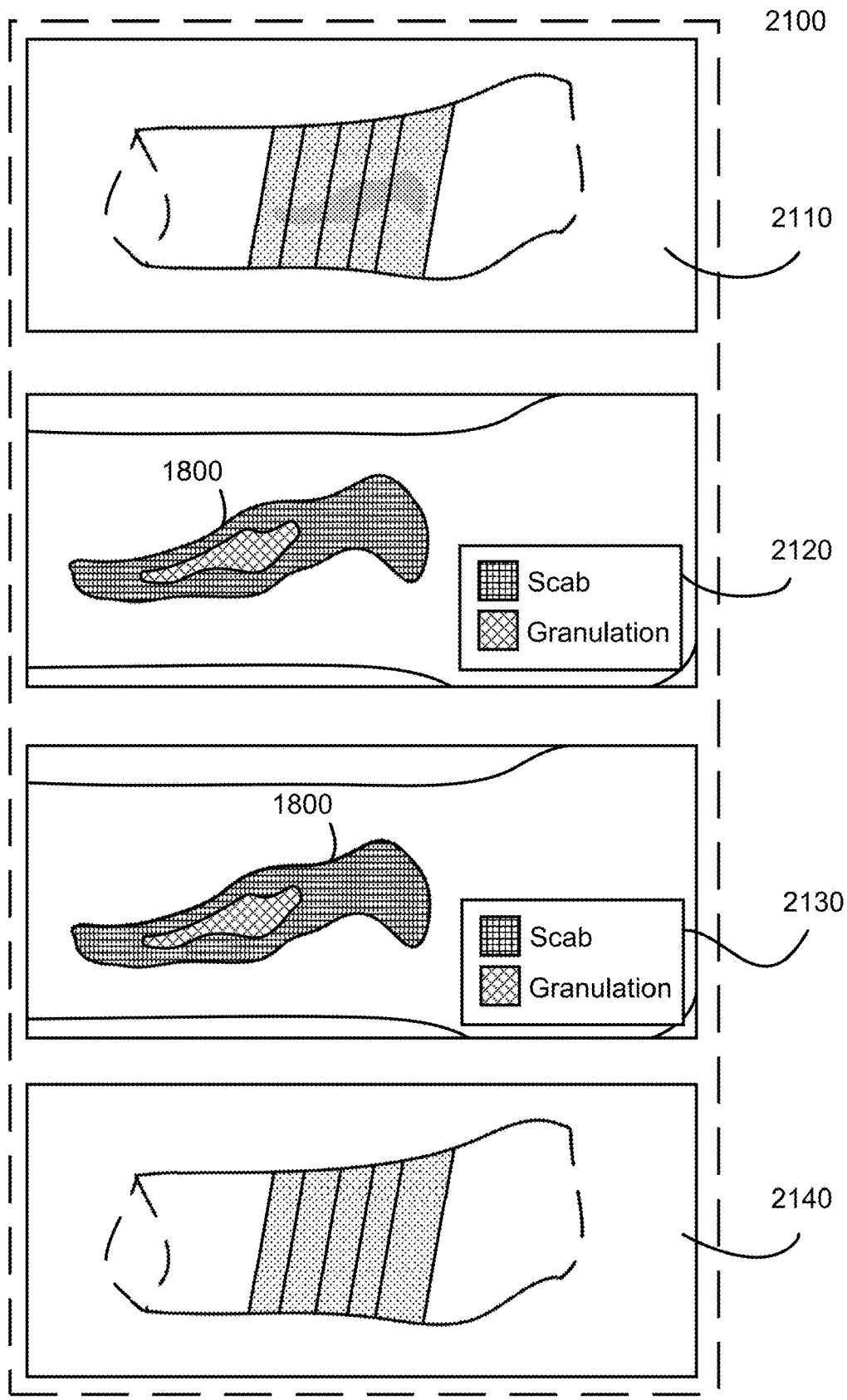
FIG. 21 is an illustration of a simulated image data record corresponding to a second point in time, consistent with some embodiments of the present disclosure.

By way of example, a simulated image of wound 1800 from the particular point of view corresponding to the second point in time associated with image data record 2000, as depicted in FIG. 20. In some embodiments, image data record 2000 may not include an image of wound 1800 from a particular point of view. For instance, server 145 may select image 1920 to generate visual time series view 2320 of FIG. 23, and image data record 2000 may not include an image of wound 1800 from the particular point of view of image 1920. In that circumstance, server 145 may generate a simulated image 2120 of wound 1800 from the particular point of view corresponding to the second point in time by analyzing at least image 2020 of image data record 2000. Similarly, a simulated image 2110, as depicted in FIG. 21, from the particular point of view of image 1910 may be generated by analyzing image 2010, and a simulated image 2130 from the particular point of view of image 1930 may be generated by analyzing image 2030. On the other hand, an image 2040 may already have the particular point of view of image 1940 and may be included in image data record 2100 as-is or with minor modifications.

In some embodiments, the second image data record may include motion data captured using an accelerometer associated with an image sensor used to capture the second one or more images of the wound, and analyzing the second image data may include analyzing the motion data. Motion data may refer to information describing a motion of an image sensor associated with the device used to capture the second one or more images of the wound included in the second image data record during the capturing of the second one or more images of the wound. An accelerometer may refer to an instrument which may measure acceleration or motion. In some embodiments, analyzing the second image data record to generate the simulated image of the wound may include analyzing the motion data. For instance, a motion or acceleration of the image sensor during the capturing of the second one or more images of the wound may be used to determine the point of view corresponding to different images included in the second image data record when generating the simulated image.

In some embodiments, generating the simulated image of the wound from the particular point of view corresponding to the second point in time may include generating the simulated image to have selected illumination characteristics. Illumination characteristics may include levels of lighting or light in an image. For example, the illumination characteristics may be global for the entire image, or limited to a specific region of the image (for example, to simulate shadows). In such embodiments, generating the simulated image of the wound from the particular point of view corresponding to the second point in time may further include analyzing the image of the wound from the particular point of view corresponding to the first point in time to select the selected illumination characteristics. For instance, illumination characteristics of the image of the wound from the particular point of view corresponding to the first point in time may be determined to provide the generated simulated image of the wound from the particular point of view corresponding to the second point in time with the same or similar illumination characteristics. By way of example, image 2010 of FIG. 20 may have different illumination characteristics than image 1910 of FIG. 19. As such, generating simulated image 2110 from the particular point of view of image 1910 may include further analyzing image 1910 to determine an illumination characteristic and apply said illumination characteristic to image 2010 to generate simulated image 2110, as depicted in FIG. 21.

Figure 19:
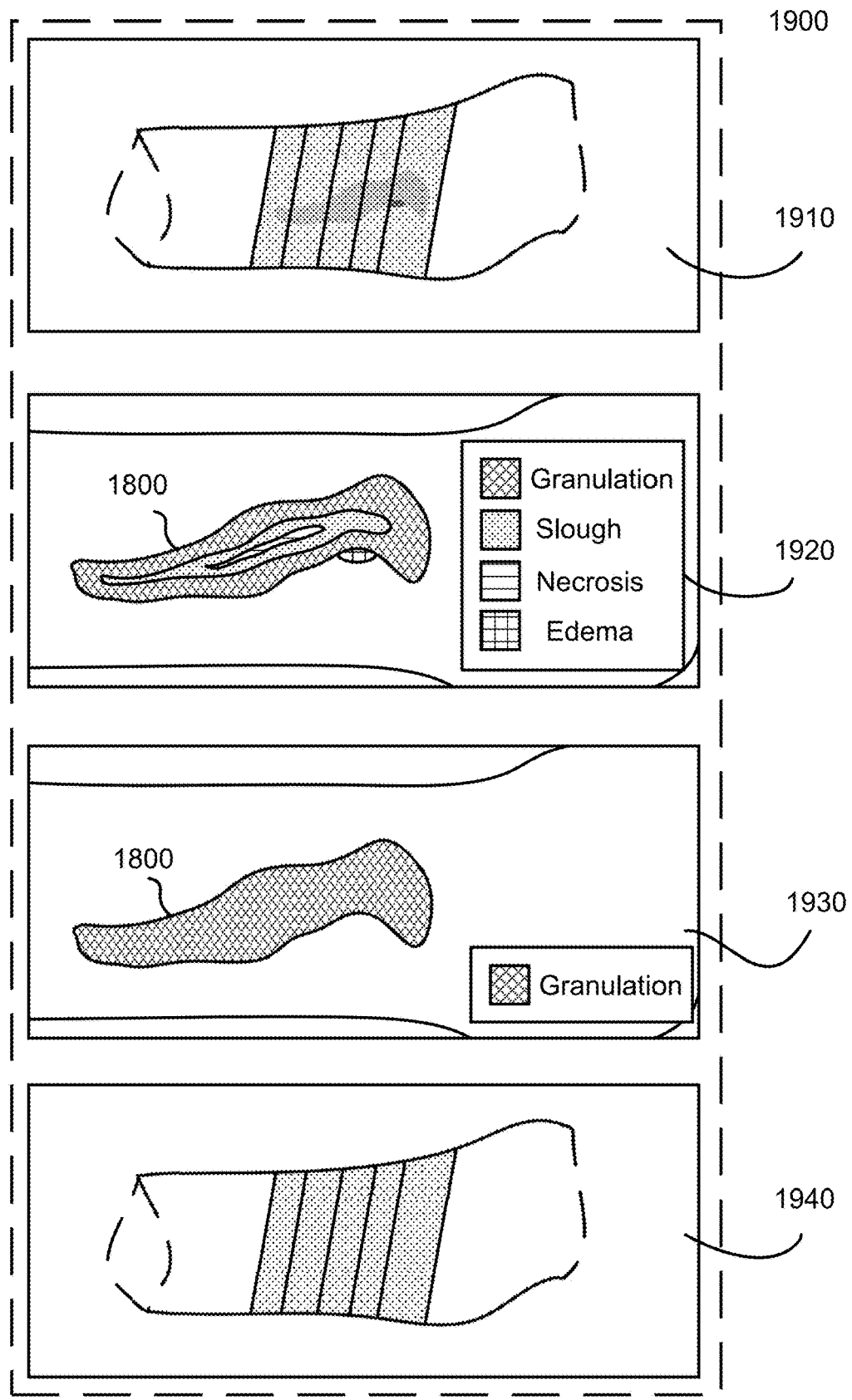
FIG. 19 is an illustration of an image data record corresponding to a first point in time, consistent with some embodiments of the present disclosure.

In some embodiments, the images of the wound from the particular point of view corresponding to the first point in time and to the second point in time may both correspond to a same distance from the wound. For instance, a distance of the image sensor to the wound in the image of the wound from the particular point of view corresponding to the first point in time may be equal to a distance of the simulated image sensor to the wound in the simulated image of the wound from the particular point of view corresponding to the second point in time. Additionally, generating the simulated image of the wound from the particular point of view corresponding to the second point in time may include generating the simulated image of the wound from the particular point of view corresponding to the second point in time by causing a distance from the wound in the simulated image to be equal to the distance from the wound associated with the image of the wound from the particular point of view corresponding to the first point in time. That is, for example, a distance from the simulated image sensor to the wound in the simulated image of the wound from the particular point of view corresponding to the second point in time may be modified to be equal to the distance from the image sensor to the wound in the image of the wound from the particular point of view corresponding to the first point in time during generation of the simulated image. By way of example, image 2030 of FIG. 20 may be at a different distance to wound 1800 than image 1910 of FIG. 19 is to wound 1800. As such, generating simulated image 2110 from the particular point of view of image 1910 may include further analyzing image 1910 to determine the distance to wound 1800 and may require modifying image 2030 to generate simulated image 2110, which may have a same distance from wound 1800 as image 1930. In some examples, a regression model may be used to analyze the image of the wound from the particular point of view corresponding to the first point in time to determine the distance from the wound associated with the image of the wound from the particular point of view corresponding to the first point in time. In one example, a size of a wound in the simulated image may be selected and/or modified to correspond to the determined distance.

In some embodiments, the images of the wound from the particular point of view corresponding to the first point in time and to the second point in time both have a same spatial orientation. For instance, a spatial orientation of the image sensor with relation to the wound in the image of the wound from the particular point of view corresponding to the first point in time may be equal to a spatial orientation of the image sensor with relation to the wound in the simulated image of the wound from the particular point of view corresponding to the second point in time. In some embodiments, however, the spatial orientations may differ, for instance, if a visual time series view of a wound is intended to show a wound from multiple angles. Additionally, generating the simulated image of the wound from the particular point of view corresponding to the second point in time includes generating the simulated image of the wound from the particular point of view corresponding to the second point in time by causing a spatial orientation in the simulated image to be equal to a spatial orientation associated with the image of the wound from the particular point of view corresponding to the first point in time. That is, for example, a spatial orientation of the simulated image sensor in relation to the wound in the simulated image of the wound from the particular point of view corresponding to the second point in time may be modified to correspond to the spatial orientation of the image sensor in relation to the wound in the image of the wound from the particular point of view corresponding to the first point in time during generation of the simulated image. By way of example, image 2020 of FIG. 20 may have a different spatial orientation than that of image 1920 of FIG. 19. As such, generating simulated image 2120 from the particular point of view of image 1920 may include further analyzing image 1920 to determine the spatial orientation of image 1920 and applying said spatial orientation to image 2020 to generate simulated image 2120. In some examples, a regression model may be used to analyze the image of the wound from the particular point of view corresponding to the first point in time to determine the spatial orientation of the wound associated with the image of the wound from the particular point of view corresponding to the first point in time. In one example, an affine transformation may be applied to the wound in the simulated image to transform it to correspond to the determined spatial orientation.

Figure 22:
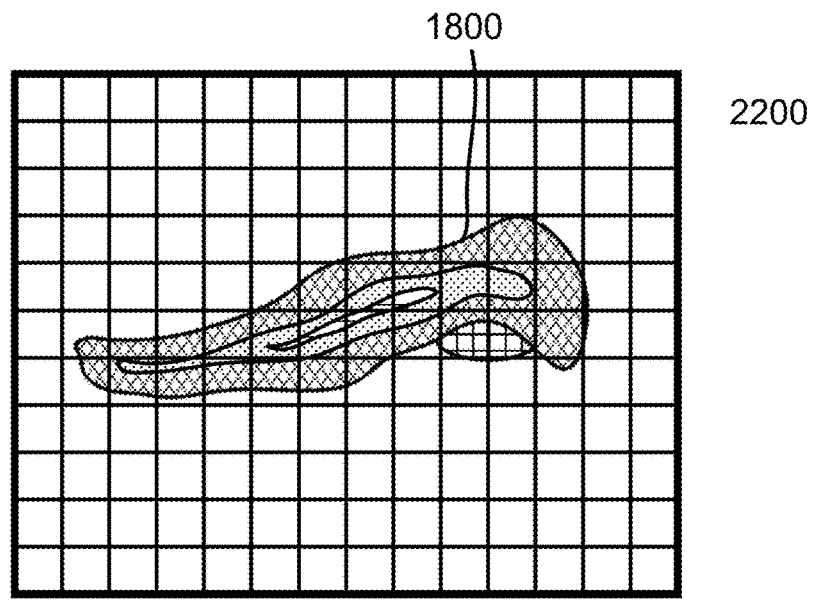
FIG. 22 is an illustration of a pixelated image and simulated image, consistent with some embodiments of the present disclosure.
Figure 22:
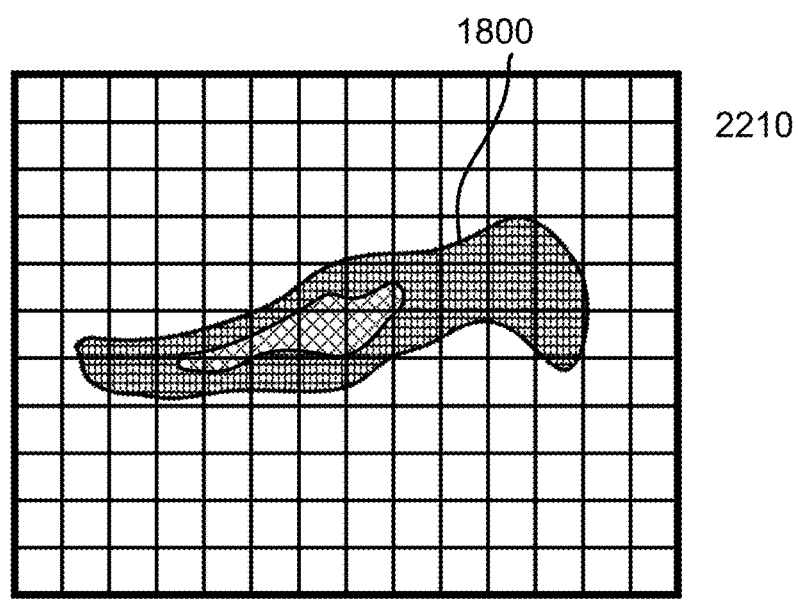

In some embodiments, pixels of at least one matching pair of pixels of the image of the wound from the particular point of view corresponding to the first point in time and from the simulated image of the wound from the particular point of view corresponding to the second point in time correspond to a same physical length. That is, for example, when generating the simulated image of the wound from the particular point of view corresponding to the second point in time, the simulated image may be resized in order to match a set of pixels in the simulated image to a similar set of pixels in the image of the wound from the particular point of view corresponding to the first point in time such that a physical length in the simulated image corresponds to same physical length in the image corresponding to the first point in time. By way of example, pixels of images 2200 and 2210, as depicted in FIG. 22 may correspond to a same physical length such that wound 1800 may maintain a same particular view throughout a visual time series view.

In some embodiments, each particular image of the wound from the particular point of view corresponding to the first point in time and to the second point in time include a visual indicator of a region of the wound corresponding to a particular tissue type in the particular image. Tissue types may include epithelial tissue, granulation tissue, slough tissue, eschar, necrotic tissue, scab, hematoma, tendon, ligament, bone, infected tissue, non-infected tissue, or any other type of tissue which may be found in a wound. A visual indicator may include, for example, text, coloration, shading, or any other type of visual aid which may differentiate one region of a wound with another. In one example, a semantic segmentation algorithm may be used to analyze the images and identify the region of the wound corresponding to the particular tissue type. In some embodiments, each particular image of the wound from the particular point of view corresponding to the first point in time and to the second point in time may include a visual indicator of a depth of the wound at a particular location. A visual indicator of a depth of the wound may include, for example, dimensions, scales, or coloration. By way of example, images 1920, 1930, 2020, 2030, 2120, and 2130 depict a visual indicator of regions of wound 1800 corresponding to particular tissue types. In one example, a regression algorithm may be used to analyze the images and identify the depth of the wound at the particular location. Other algorithms for determining the depth of the wound which may be used are described herein.

Embodiments of the present disclosure may include generating a visual time series view of the wound including at least the image of the wound from the particular point of view corresponding to the first point in time and the simulated image of the wound from the particular point of view corresponding to the second point in time. A visual time series view of the wound may refer to a series of images, other visual representations, and/or data relating to the wound ordered in time. In one example, the visual time series of the wound may be a video of the wound including a frame depicting the wound from the particular point of view corresponding to the first point in time and a frame depicting the wound from the particular point of view corresponding to the second point in time. The visual time series view of the wound may include at least the image of the wound from the particular point of view corresponding to the first point in time and the simulated image of the wound from the particular point of view corresponding to the second point in time, ordered from the first point in time to the second point in time, or from the second point in time to the first point in time. The visual time series view of the wound may include one or more images corresponding to a third point in time, a fourth point in time, and any appropriate number of points in time. In some embodiments, each image of the images in the visual time series view of the wound may correspond to a point in time, and the images in the visual time series view of the wound may be ordered based on the corresponding points in time. By way of example, visual time series views 2310, 2320, 2330, and 2340 include images of wound 1800 from a particular point of view corresponding to a first point in time and a second point in time. For instance, visual time series view 2310 includes image 1910 and simulated image 2110 ordered based on corresponding points in time.

Consistent with some embodiments of the present disclosure, the images of the wound from the particular point of view corresponding to the first point in time and to the second point in time may both correspond to a same treatment phase of a treatment cycle of the wound. A treatment cycle may refer to a series of steps that a wound may undertake during treatment. For instance, a wound may require daily treatment/cleaning and bandage changing, so a treatment cycle may include removing the bandages from the wound, cleaning and/or otherwise treating the wound, and applying new bandages to the wound. A treatment phase of the treatment cycle of the wound may refer to a step of the treatment cycle. For instance, a treatment phase may refer to the removal of the bandages from the wound, the cleaning and/or treatment of the wound, and the application of new bandages to the wound. The images of the wound from the particular point of view corresponding to the first point in time and to the second point in time may therefore both correspond to the same treatment phase of a treatment cycle of the wound. For example, both images may depict the wound before the bandages are removed, after the bandages are removed but before cleaning/treatment, after cleaning/treatment, or after the new bandages are applied. In some embodiments, one or more pairs of images of the wound from the particular point of view corresponding to the first point in time and to the second point in time may be generated, wherein each pair of images of the wound correspond to a different treatment phase of a treatment cycle of the wound. In some embodiments, the images of the wound from the particular point of view corresponding to the first point in time and to the second point in time may both correspond to the wound before or after debridement, before or after dressing, or before or after an application of a medication to the wound. Debridement may refer to the removal of nonviable material, foreign bodies, and poorly healing tissue from a wound. Dressing may refer to the application of bandaging to the wound and/or the area surrounding the wound.

By way of example, images of wound 1800 may correspond to a treatment phase of a treatment cycle of wound 1800. For instance, images 1910, 2010, and 2110 may correspond to wound 1800 before undressing, images 1920, 2020, and 2120 may correspond to wound 1800 before debridement, images 1930, 2030, and 2130 may correspond to wound 1800 after debridement, and images 1940, 2040, and 2140 may correspond to wound 1800 after dressing.

In some embodiments, generating the simulated image of the wound from the particular point of view corresponding to the second point in time may include analyzing the image of the wound from the particular point of view corresponding to the first point in time to determine a treatment phase of the treatment cycle of the wound corresponding to the image of the wound from the particular point of view corresponding to the first point in time and generating the simulated image of the wound from the particular point of view corresponding to the second point in time to correspond to the determined treatment phase. That is, for example, the image of the wound from the particular point of view corresponding to the first point in time may be analyzed to ascertain which treatment phase of a treatment cycle the wound is in in order to generate a simulated image of the wound from the particular point of view corresponding to the second point in time which matches the treatment phase of the image of the wound corresponding to the first point in time. In one example, a classification algorithm may be used to analyze the image of the wound from the particular point of view corresponding to the first point in time to classify it to one of a plurality of alternative classes. Each class may correspond to a treatment phase of the treatment cycle of the wound, and the classification of the image to the class may thereby determine the treatment phase of the treatment cycle of the wound.

Some embodiments of the present disclosure may include calculating a convolution of a part of an image of the first one or more images to derive a first result value, calculating a convolution of a part of an image of the second one or more images to derive a second result value, and determining a value of at least one pixel of the simulated image of the wound from the particular point of view corresponding to the second point in time based on the first result value and the second result value. In one example, the value of the at least one pixel of the simulated image of the wound from the particular point of view corresponding to the second point in time may be a function of the first result value and the second result value. In another example, in response to one combination of the first result value and the second result value, a first value may be determined for the at least one pixel of the simulated image of the wound from the particular point of view corresponding to the second point in time, and in response to a second combination of the first result value and the second result value, a second value may be determined for the at least one pixel of the simulated image of the wound from the particular point of view corresponding to the second point in time.

Some embodiments of the present disclosure may include analyzing a first image of the first one or more images to detect a region of the wound corresponding to a particular tissue type in the first image, analyzing a second image of the second one or more images to detect a region of the wound corresponding to the particular tissue type in the second image, and determining a value of at least one pixel of the simulated image of the wound from the particular point of view corresponding to the second point in time based on the region of the wound corresponding to the particular tissue type in the first image and the region of the wound corresponding to the particular tissue type in the second image. A value of a pixel may refer to a coloration of a pixel, for instance, an RGB color value of a pixel. For example, a length of the detected region of the wound corresponding to the particular tissue type in the second image may be used to determine a size of a region corresponding to the particular tissue type in the simulated image, and a location of the region of the wound corresponding to the particular tissue type in the first image may be used to determine a location of the region corresponding to the particular tissue type in the simulated image. The location and size of the region corresponding to the particular tissue type in the simulated image may be used to determine whether the at least one pixel of the simulated image of the wound is in the region corresponding to the particular tissue type in the simulated image, and the value of the at least one pixel may be determined based on whether the at least one pixel of the simulated image of the wound is in the region corresponding to the particular tissue type in the simulated image.

Figure 24:
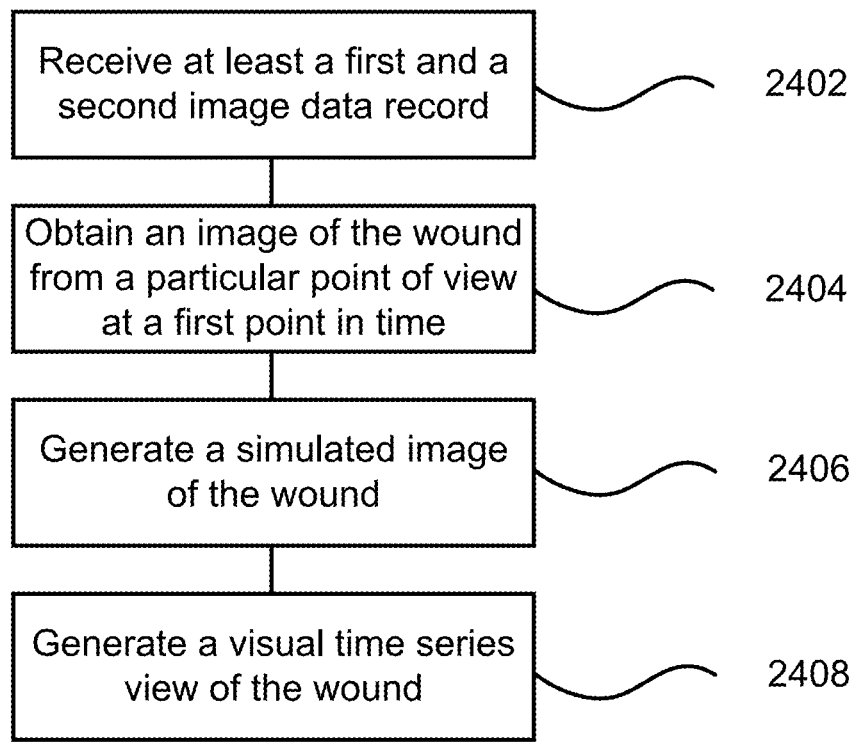
FIG. 24 is an example process for generating visual time series views of wounds, consistent with some embodiments of the present disclosure.

FIG. 24 provides a flowchart of an example process 2400 for generating visual time series views of wounds including steps 2402 through 2408. Steps 2402 through 2408 may be executed by at least one processor (e.g., processing device 202 of server 145 or mobile communications device 115 of FIG. 2), consistent with some embodiments of the present disclosure.

Process 2400 may begin with step 2402. At step 2402, the at least one processor may receive at least a first image data record and a second image data record, the first image data record corresponding to a first point in time and including a first one or more images of a wound captured at the first point in time, and the second image data record corresponding to a second point in time and including a second one or more images of the wound captured at the second point in time, the images being captured by, for example, image sensor 226 of FIG. 2, which may be associated with a mobile device, such as communications device 115.

Once the first and second image data records are received, process 2400 may proceed to step 2404. At step 2404, the at least one processor may obtain an image of the wound from a particular point of view corresponding to the first point in time by analyzing the first image data record.

At step 2406, the at least one processor may generate a simulated image of the wound from the particular point of view corresponding to the second point in time by analyzing the second image data record, wherein the second one or more images of the wound do not include an image of the wound from the particular point of view.

Once the simulated image has been generated, process 2400 may proceed to step 2408. At step 2408, the at least one processor may generate a visual time series view of the wound including at least the image of the wound from the particular point of view corresponding to the first point in time and the simulated image of the wound from the particular point of view corresponding to the second point in time.

Embodiments consistent with the present disclosure provide systems, methods, devices, and computer readable media for rearranging and selecting frames of a medical video. For ease of discussion, in some instances related embodiments are described below in connection with a system or method with the understanding that the disclosed aspects of the system and method apply equally to each other as well as devices and computer readable media. Some aspects of a related method may occur electronically over a network that is either wired, wireless, or both. Other aspects of such a method may occur using non-electronic means. In the broadest sense, the methods and computer readable media are not limited to particular physical and/or electronic instrumentalities, but rather may be accomplished using many differing instrumentalities. In some embodiments, the medical video may include a wound. A wound as referred to herein may include any injury to the human body. For example, wounds may be open wounds resulting from penetration (e.g., puncture wounds, surgical wounds and incisions, thermal, chemical, or electric burns, bites and stings, gunshot wounds, etc.) and/or blunt trauma (e.g., abrasions, lacerations, skin tears), or they may include closed wounds (e.g., contusions, blisters, seromas, hematomas, crush injuries, etc.). Some non-limiting examples of a wound may include a chronic wound, acute wound, ulcer (such as venous ulcer, arterial ulcer, diabetic ulcer, pressure ulcer, etc.), infectious wound, ischemic wound, surgical wound, radiation poisoning wound, and so forth.

Disclosed embodiments may involve obtaining a desired property of a simulated trajectory of a virtual camera. A virtual camera as used herein may refer to a camera that does not necessarily exist as a physical camera, but is made by software to appear to do so. That is, a virtual camera may be computer-generated, and may be used, accessed, or stored by means of a computer and/or computer network (e.g., system 100 in FIG. 1A and components thereof). For example, a virtual camera may never exist, while a video may be generated to appear as if a virtual camera with particular characteristics (such as position, orientation, motion, trajectory, zoom, focus, spectral sensitivity, focal length, field of view, resolution, color depth, frame rate, and so forth) captured the video. A trajectory may include any two dimensional or three dimensional pathway between two or more points in physical space, and a simulated trajectory may include any two dimensional or three dimensional path between two or more points in a virtual space (e.g., a simulation of a physical space run by computer software). When referring to a simulated trajectory of a moving camera or a virtual camera, a trajectory may also include a viewing angle of the respective camera along the path of the respective trajectory. For example, in some embodiments, a trajectory of a moving camera includes a path followed by the moving camera from a first position to a second position in physical space, and the simulated trajectory includes a generated path between the first position and the second position, for example in a corresponding virtual space, in a physical space, and so forth. The simulated trajectory between the first position and the second position may be computer generated and may be configured to include a specific set of viewing angles of a wound.

Consistent with some embodiments of the present disclosure, the trajectory of a moving camera and a corresponding simulated trajectory may be different. For example, although a trajectory of a moving camera and a trajectory of a counterpart virtual camera may both include the same start position and end position, the path between the two positions in the simulated trajectory, as well as the viewing angle of the virtual camera along the path, may be different than that of the physical trajectory. For example, in some embodiments, the trajectory of the moving camera may include a diversion rendering at least a portion of the trajectory non-linear, and in one example the simulated trajectory does not include the diversion. Thus, the corresponding portion of the simulated trajectory may differ from the trajectory of the moving camera. In one example, the corresponding portion of the simulated trajectory may be linear, while the trajectory of the moving camera may be non-linear. In another example, the corresponding portion of the simulated trajectory may be smooth, while the trajectory of the moving camera may be uneven. For example, the simulated trajectory may be configured to provide at least one view of a wound of a patient. While moving along the simulated trajectory, the virtual camera may record or provide a feed of a video of the wound. Consistent with disclosed embodiments, a simulated trajectory may include both linear and non-linear portions. For example, in some embodiments, at least a portion of the simulated trajectory may be selected to be substantially on an arc of a circle, the wound being located at or near the center of the circle. The center of the circle may be positioned along the viewing angle of the virtual camera, such that the virtual camera is angled directly at or near the wound, consistent with some embodiments of the present disclosure.

In some embodiments, the simulated trajectory may be a standard wound viewing trajectory. That is, the trajectory of the virtual camera may be configured as to conform to a standard for capturing medical videos associated with one or more healthcare providers, such as an association of medical practitioners, a governing authority associated with the practice of medicine, or any other entity associated with the provision of healthcare (e.g., one or more individual hospitals, clinics, practice areas, etc.). A standard consistent with the present disclosure may have specific requirements for a particular property or range of properties that a trajectory must conform with in order to comply with the standard. For example, some non-limiting examples of properties associated with standard wound viewing trajectories may include specific directions, viewing angles, viewing distances, speeds, illumination conditions, lengths, and the like, as discussed with further detail herein.

Figure 25A:
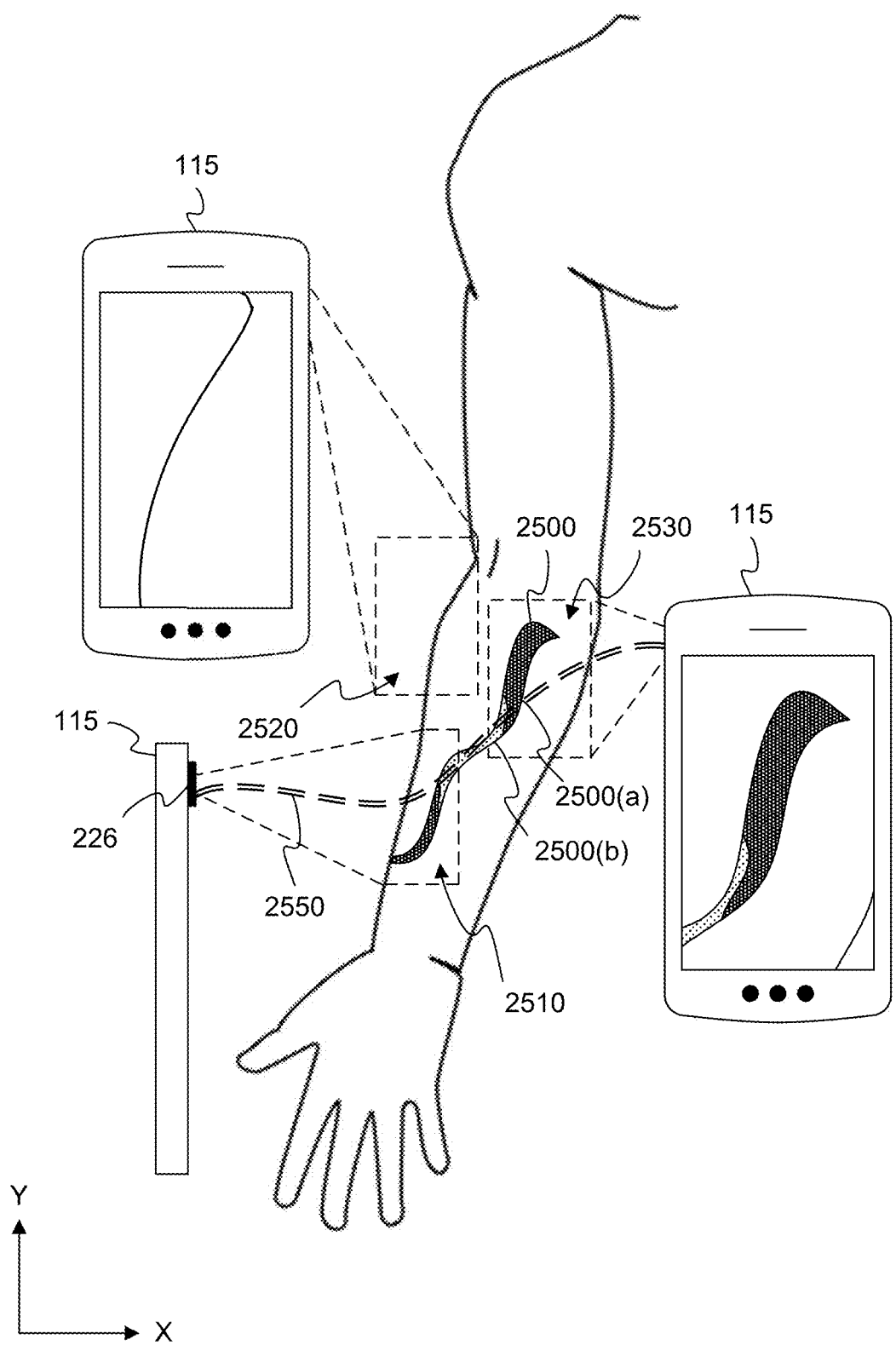
FIG. 25A is an illustrative X-Y view of an example simulated trajectory of a virtual camera for creating a new video of a wound of a patient, consistent with some embodiments of the present disclosure.
Figure 25B:
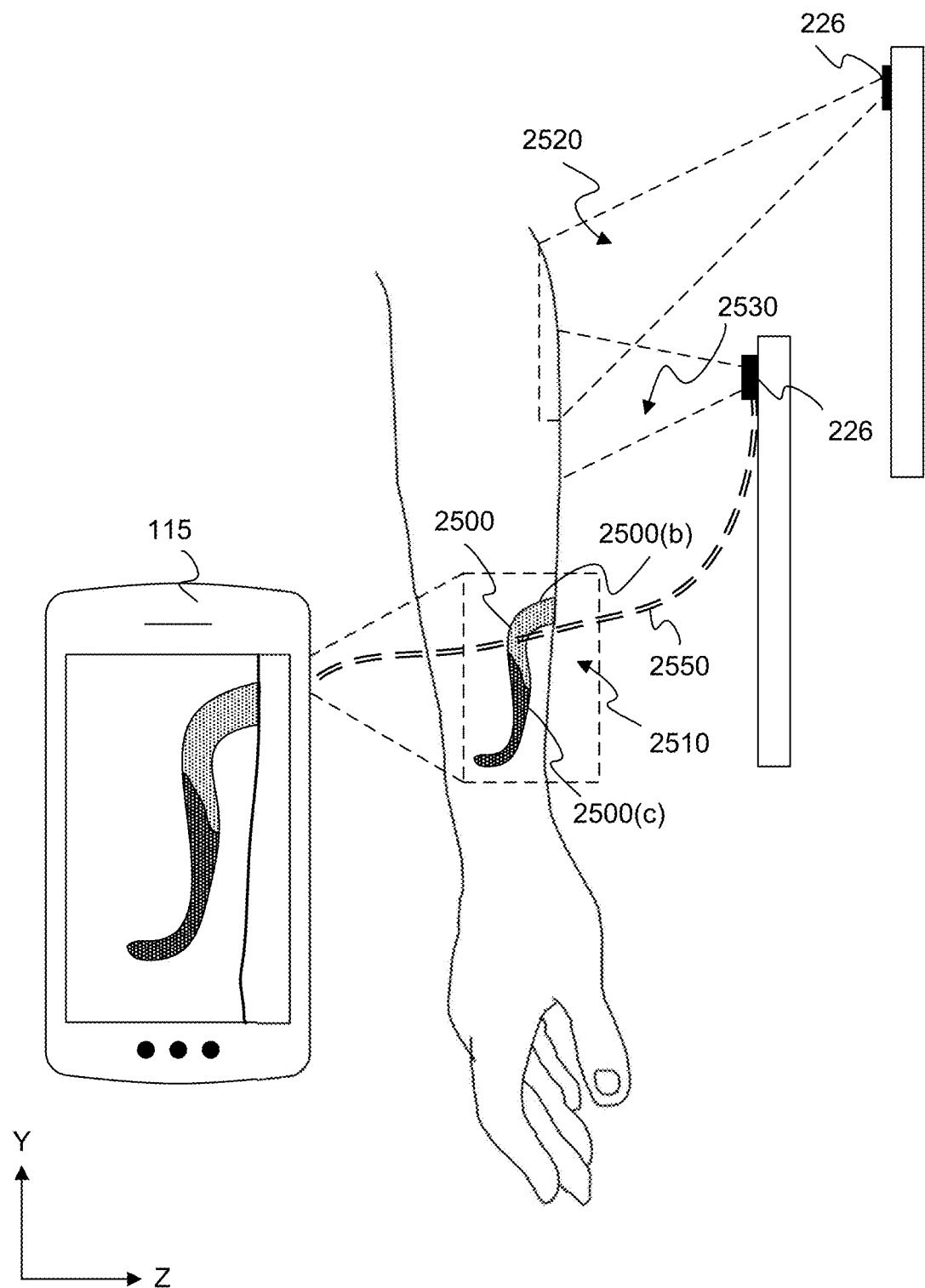
FIG. 25B is an illustrative Y-Z view of an example simulated trajectory of a virtual camera for creating a new video of a wound of a patient, consistent with some embodiments of the present disclosure.
Figure 25C:
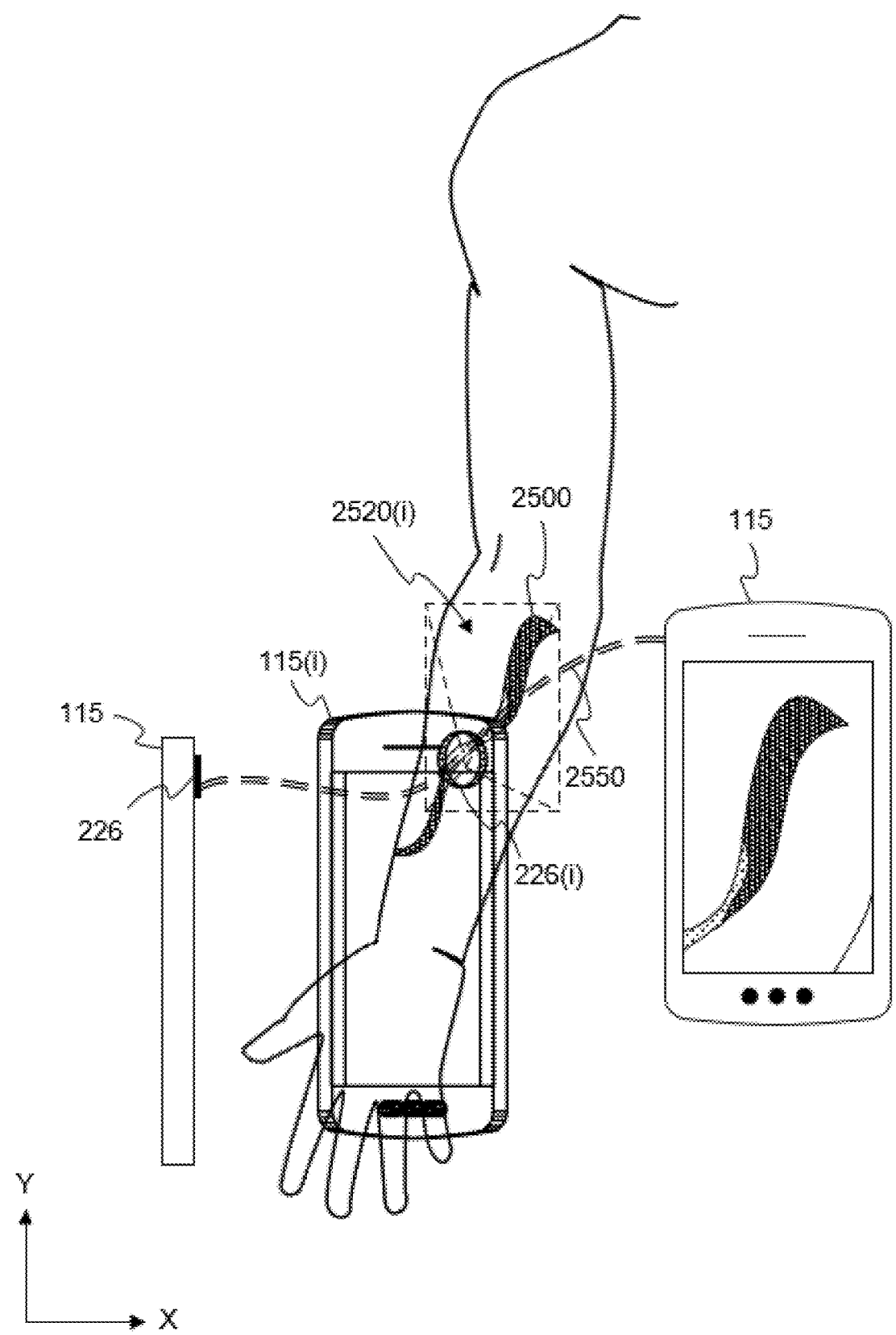
FIG. 25C is another illustrative Y-Z view of an example virtual camera moving along a simulated trajectory for creating a new video of a wound of a patient, consistent with some embodiments of the present disclosure.

By way of example, FIGS. 25A and 25B provide a view of a wound 2500 on an arm of a patient in an X-Y plane and a Y-Z plane, respectively, and illustrate an example of a simulated trajectory of a virtual camera delineated by double dashed lines 2550, consistent with some embodiments of the present disclosure. For illustrative purposes and ease of discussion, FIG. 25C provides yet another view of wound 2500 on the arm of the patient in the X-Y plane, with virtual device 115(*i*) having virtual camera 226(*i*) illustrated translucently therein and being positioned along simulated trajectory 2550. Virtual camera 226(*i*) may be a virtual version of image sensor 226 of mobile communications device 115 and may be simulated by one or more programs stored in at least one data structure (e.g., memory device 234 of mobile communications device 115 and/or database 146 of server 145 as illustrated in FIG. 2) when executed by at least one processor (e.g., processing device 202 of mobile communications device 115 and/or server 145) to capture a virtual video of wound 2500. Simulated trajectory 2550 may include a first position and a second position, the first position corresponding to a position of image sensor 226 as it captures image 2510, and the second position corresponding to a position of image sensor 226 as it captures image 2530.

Virtual camera 226(i), as illustrated in FIG. 25C, may, in the first position, have a viewing angle directed to the radial portion of the patient's forearm and, in the second position, have a viewing angle directed to the base of the patient's inner forearm. The viewing angle of virtual camera 226(i) may be maintained such that it remains directed at wound 2500 as it moves from the first position to the second position. FIGS. 25A and 25B also illustrate mobile communications device 115 in a third position that is not included in simulated trajectory 2550, in which image sensor 226 captures image 2520. This third position may correspond to a position of image sensor 226 that travels along a trajectory other than physical trajectory 2550 between capturing image 2510 and 2530. Simulated trajectory 2550 may include linear and non-linear portions. For example, at least one portion of simulated trajectory 2550 may include an arc of a circle being centered at or near at least one portion of wound 2500. For example, an arc of trajectory may be centered on a specific point on wound 2500, a boundary of wound 2500, a contour of wound 2500, an axis tangentially aligned with a boundary of wound 2500, etc., or it may be centered around a specific point or axis near wound 2500, such as a calibrator (e.g., colorized surface 132 as illustrated in FIG. 4A) or around an axis coinciding with or parallel with the patent's forearm (e.g., the ulna or radius).

As discussed above, embodiments consistent with the present disclosure may involve obtaining at least one desired property of the simulated trajectory. For example, the desired property of the simulated trajectory may be read from memory, may be received from an external device, may be obtained from a user (for example, using a user interface), may be determined automatically (for example, by analyzing a video, for example using an egomotion algorithm, for example to mimic a trajectory associated with the video), and so forth. A property of the simulated trajectory may include any physical or digital parameter associated with the path of the trajectory (e.g., length, curvature, direction, etc.), the positioning and movement of the camera (e.g., speed, direction, viewing angle, time of movement, etc.), configurations of the camera and associated components (e.g., image resolution, frame rate, gain, ISO speed, stereo base, lens, focus, zoom, color correction profile, flash, etc.), programs and programming configurations (e.g., in FIG. 2, sensor processing instructions 242, capturing instructions 254, application specific instructions 260, etc.) associated with a device capturing the video (e.g., image sensor 226), virtual device capturing the virtual video (e.g., virtual camera 226(i)), and/or image processing device (e.g., processor 202 of communications device 115 or server 145, as illustrated in FIG. 2), and so forth. A specific set of properties may be desired, for example, to improve the quality of the video, or to comply with a particular standard associated with the video.

In some embodiments consistent with the present disclosure, the desired property of the simulated trajectory of the virtual camera may include a desired moving direction of the virtual camera. Consistent with the present disclosure, the direction may be based on a standard that requires videos to be captured along a specific direction (e.g., left to right), or it may be based on physical properties of the patient and/or the wound to be captured. For example, in some embodiments, obtaining the desired property of the simulated trajectory may comprise selecting the desired moving direction of the virtual camera based on a contour of the wound. In one example, the direction of the trajectory's path may be selected to align or closely align with a contour of the wound (e.g., a boundary of the wound or a boundary of a tissue type in the wound), such that the trajectory's path is configured such that the contour of the wound remains at least partially centered in the virtual camera's frame of view as the virtual camera moves along the simulated trajectory. In another example, the contour of the wound may be analyzed to determine a lengthwise direction corresponding to the wound, and the desired moving direction may be in the determined lengthwise direction, perpendicular to the determined lengthwise direction, in a selected angle with respect to the determined lengthwise direction, and so forth.

Consistent with some embodiments of the present disclosure, the desired property of the simulated trajectory of the virtual camera may include a desired velocity of the virtual camera, and/or the desired property may include a desired distance of the virtual camera from the wound. The speed of the virtual camera and the desired distance of the virtual camera from the wound may be constant throughout the entire trajectory, or the speed and desired distance may vary based on any one or more properties associated with the wound, patient, camera, device, or so forth. For example, a lower speed and/or shorter distance may be desired in order to capture more detailed images of a wound. In one example, the image quality of one or more segments of the wound in particular (e.g., a segment corresponding to a tissue type) may be desired. Thus, a distance and/or speed of the camera in at least one portion of the trajectory corresponding with the one or more particular segments may be reduced to improve the quality and/or detail of the portion of the virtual video containing the one or more particular segments. In other examples, a desired distance may be selected based on the focal length of the camera or due to the dimensions of the wound. In yet another example, the velocity of the virtual camera may be selected based on the time dependent properties of the camera (e.g., frame rate, gain, ISO speed, etc.) or on the dimensions of the wound. Some additional non-limiting examples of factors affecting the desired velocity of the virtual camera and/or desired distance of the virtual camera from the wound may include illumination conditions (for example, having lower velocity and/or shorter distance when the illumination conditions are poor), condition of the wound, tissue composition of the wound, depth of the wound, and so forth.

By way of example, in FIGS. 25A-C, wound 2500 has a snake-like shape that has one end located near the radial side of the patient's wrist and another end located on the base of the patient's inner forearm. In some embodiments, the direction of movement of virtual camera 226(i), as illustrated in FIG. 25C, may be selected to roughly follow (or to precisely follow, in some embodiments) the contour of wound 2500, such that the virtual video captured by virtual camera 226(i) includes images of wound 2500. In some embodiments, virtual camera 226(i) may travel at variable velocity and at a variable distance from wound 2500 along trajectory 2550, consistent with some embodiments with the present disclosure. For example, wound 2500 may include segments 2500(a)-(c), where a high amount of detail corresponding to the video of segment 2500(b) is desired. The velocity of virtual camera 226(i) may be reduced as segment 2500(b) passes through the frame of the virtual image captured by virtual camera 226(i) as virtual camera 226(i) moves through the corresponding portion of simulated trajectory 2550. The corresponding portion of simulated trajectory 2550 may, in some embodiments, be associated with a shorter distance from wound 2550 in order for virtual camera 226(i) to collect images with more detail.

Some embodiments consistent with the present disclosure may include analyzing at least one image of the wound to determine a condition of at least part of the wound. Consistent with the present disclosure, a condition of a wound as referred to herein may refer to a medical condition (e.g., infection), healing stage, or any other physical parameter associated with a wound. A condition associated with a wound may, for example, be determined by a medical professional (e.g., medical practitioner 120 in FIG. 1A) and placed into a record corresponding to the wound (e.g., saved in database 146). However, some embodiments of the disclosure may include using machine learning, as previously discussed herein, to determine a condition of a wound or to estimate and/or interpolate a condition of a wound. For example, in some embodiments, a machine learning model (e.g., a classification model) may be trained using training examples to determine one or more conditions of a wound in one or more images. Examples of training examples for determining a condition of a wound may include sample images of wounds having known conditions (e.g., an infected wound with predetermined measurements, color, tissue types, etc.). The trained machine learning model may be used to analyze the at least one image of the wound to determine a condition of the wound. In some embodiments, the at least one analyzed image may be an image in the captured video, one or more separate captured videos, one or more separately captured images, or one or more images in a virtual video.

In some embodiments, the simulated trajectory of the virtual camera may be determined based on a condition of the at least part of the wound. The condition of the at least part of the wound may correspond to a particular segment of the wound, or the condition itself may constitute a segment of a wound. Determining the simulated trajectory based on the condition of the wound may, for example, involve obtaining one or more desired properties of a simulated trajectory configured to capture a video containing quality image data associated with the condition. In some embodiments, the simulated trajectory may be configured to correspond with a physical parameter and/or dimension of the specific condition. For example, the desired properties of the trajectory may include one or more directions and/or distances configured to enable the virtual camera to capture a video containing images of the at least a portion of the wound with the condition. In some embodiments, the at least one simulated trajectory may be determined based on a characteristic of the condition (e.g., a type of infection). In one example, a wound may be infected, and at least a portion of the desired trajectory may involve a low speed and/or distance of the virtual camera as it moves along one or more directions configured to roughly follow a contour of the infected segment of the wound. By way of example, segment 2500(b) may be an infected portion of wound 2500, and a specific desired velocity of virtual camera 226(i) and distance of camera 226(i) from segment 2500(b) may be selected in order to obtain a virtual video of segment 2500(b) with a high amount of detail.

Some embodiments consistent with the present disclosure may include analyzing at least one image of the wound to identify a first region of the wound corresponding to a first tissue type and a second region of the wound corresponding to a second tissue type. Identifying a region of the wound based on a tissue type may refer to receiving, generating, or otherwise acquiring a division into separate parts or regions of the wound based on different tissue types present in the wound. For instance, a wound may be segmented into regions based on different areas of the wound consisting of different types of tissues. Tissue types may include epithelial tissue, granulation tissue, slough tissue, eschar, necrotic tissue, scab, hematoma, tendon, ligament, bone, infected tissue, non-infected tissue, or any other type of tissue which may be found in a wound. For example, in some embodiments, a machine learning model (e.g., a semantic segmentation model, etc.) may be trained using training examples to identify one or more regions of a wound corresponding to one or more tissue types. Examples of training examples for a tissue type may include sample images of wounds having known tissue types (e.g., images of tendons, ligaments, bones, etc.). The trained machine learning model may be used to analyze the at least one image of the wound to identify at least one region of the wound corresponding to a particular tissue type. As discussed above, the at least one analyzed image may be an image in the captured video, one or more separate captured videos, one or more separately captured images, or one or more images in a virtual video.

In some embodiments, the simulated trajectory of the virtual camera may be determined based on a dimension of the first region of the wound, the first tissue type, a dimension of the second region of the wound, and the second tissue type. Determining the simulated trajectory based on the dimensions of a tissue type may include, for example, obtaining one or more desired properties of a simulated trajectory configured to capture a video containing images of at least a portion of the first region and/or the second region. In some embodiments, for example, the simulated trajectory may be configured to capture at least one image with the entire dimension or at least a portion of the dimension in the frame. For example, in some embodiments, a constant number of frames may be allocated for the new video of the wound (for example, to keep the length of the video fixed). To allocate the frames to a first portion of the simulated trajectory associated with the first region of the wound and to a second portion of the simulated trajectory associated with the second region of the wound, a weight for each portion may be calculated based on the dimension of the region and the tissue type corresponding to the region associated with the portion, and a ratio of the constant number of frames proportional to the weight corresponding to the portion may be allocated to the portion. In one example, each tissue type may correspond to a predetermined factor, and the weight corresponding to a portion of the simulated trajectory may be a multiplication of the corresponding factor and dimension. In another example, a numerical parameter may be determined based on the tissue type, and the weight corresponding to a portion of the simulated trajectory may be calculated using a parametric function of the corresponding dimension using the determined numerical parameter. By way of example, in FIG. 25A-C, wound 2500 may include tissue segments 2500(a)-(c). In some embodiments, segments 2500(a) and 2500(c) may correspond to a first tissue type, and segment 2500(b) may correspond to a second tissue type. In one example, segments 2500(a) and 2500(c) may be made of scab tissue, whereas segment 2500(b) may be exposed epithelial tissue. If, for example, a video examining the epithelial tissue of segment 2500(b) is desired, then simulated trajectory 2550 may be specifically configured to capture a high quality video of segment 2500(b) using the dimensions of segments 2500(a)-2500(b), Embodiments consistent with the present disclosure may involve receiving a first video of a wound captured by a moving camera. The first video may include a plurality of frames. Consistent with some embodiments of the present disclosure, the plurality of frames may include at least two frames corresponding to the simulated trajectory of the virtual camera. In some embodiments, the first video may be analyzed to select the at least two frames corresponding to the simulated trajectory of the virtual camera using the at least one desired property of the simulated trajectory. In some examples, embodiments of the present disclosure may involve determining at least one property associated with the plurality of frames in the first video (e.g., using image processing as discussed previously herein). The at least one property of the plurality of image frames may be compared with at least one desired property of the simulated trajectory to determine that the at least two frames correspond to the simulated trajectory. By way of example FIG. 25A, the first video may be a video captured by image sensor 226 of mobile communications device 115. The trajectory of image sensor 226 may include the position where image sensor 226 captures image 2510, another position where image sensor 226 captures image 2520, and yet another position where image sensor 226 captures image 2530. The video captured by image sensor 226 may include frames including image 2510, image 2520, and image 2530. In some embodiments, at least one processor (e.g., processor 202 of mobile communications device 115 or server 145, as illustrated in FIG. 2) may be configured to perform image processing on images 2510, 2520, and 2530 (e.g., by calculating a convolution to derive a result value) to determine certain properties of images 2510, 2520, and 2530. Based on a comparison between the determined properties and the desired properties of trajectory 2550, the at least one processor may determine that images 2510 and 2530 correspond to simulated trajectory 2550.

In some disclosed embodiments, the simulated trajectory may be selected based on a second video of a wound captured at a different time. For example, in some embodiments, the simulated trajectory may be configured to follow a similar trajectory that was previously used to capture a video of the wound. In this sense, the simulated trajectory of the virtual camera may appear to be a recreation of the previously captured video. In some embodiments, the wound in the second video captured at a different time may be the same wound as the wound in the first video. However, in some embodiments, the two wounds may be different, with enough similar features such that the trajectory of the moving camera from the second video is desired to capture a virtual video using frames from the first video (e.g., similar patients, similar injuries, similar limbs, etc.). Some disclosed embodiments may also include causing a display of the second video in conjunction with a display of a new video created with the simulated trajectory, as discussed in further detail below. The second video may be displayed, for example, alongside a playback of the new video as to provide a user with a comparison view of the wound in the first video and the wound in the second video, for example in a user interface. In another example, the second video may be displayed as an overlay over a playback of the new video.

By way of example, in FIGS. 25A-C, as previously discussed herein, a first video may be obtained using image sensor 226 of mobile communications device 115. Simulated trajectory 2550 may be determined, for example, by obtaining one or more desired properties of trajectory 2550. In some, embodiments, however, simulated trajectory 2550 may be based on the trajectory of a camera in a previously captured video. That is, simulated trajectory may be based on a video recorded along trajectory 2550, the second video including images taken in the same position as images 2510 and 2530.

Some embodiments may include using the desired property of the simulated trajectory of the virtual camera to select an order for the selected at least two frames. In some examples, the order of the selected at least two frames may selected in the same order that they were captured in the first video. For example, in FIGS. 25A-C, assuming the at least two frames include images 2510 and 2530, frames 2510 and 2530 may be selected in the order they were captured. However, in some embodiments, images 2510 and 2530 may be selected in the opposite order, for example if the desired direction of trajectory 2550 is in a direction that is opposing the direction traveled by image sensor 226 or if frames 2510 and 2530 are otherwise captured in a different order then they are to appear in the virtual video along simulated trajectory 2550. In other examples, when the selected at least two frames are at least three frames, the selected order may include any possible rearrangement of the at least three frames. For example, a middle frame of the at least three frames (in the order of capturing of the frames) may be the first frame in the selected order, may be the last frame in the selected order, may be a middle frame in the selected order, and so forth. Likewise, a first frame or a last frame of the at least three frames (in the order of capturing of the frames) may be the first frame in the selected order, may be the last frame in the selected order, may be a middle frame in the selected order, and so forth.

Embodiments consistent with the present disclosure may include rearranging the at least two frames based on the selected order to create a new video of the wound that represents the simulated trajectory of the virtual camera. A new video reflecting the simulated trajectory of the virtual camera may include a video that, as viewed by a user, may appear as having been captured by an actual camera that captured the at least two frames along the simulated trajectory. As discussed above, the selected order of the at least two frames may be any order, regardless of which order the frames were captured in, in accordance with the desired properties of the simulated trajectory. Thus, the new video created to reflect the simulated trajectory may include any number of selected frames from an actual video arranged in any order, so long as the selected frames include the desired properties of the simulated trajectory.

In some embodiments consistent with the present disclosure, creating the new video comprises generating at least one synthetic frame by analyzing the first video, and wherein the new video includes the at least one synthetic frame. Generating a synthetic frame may involve interpolation, where the frame is synthesized in between existing frames, or it may involve extrapolation, where the frame is synthesized subsequent to existing frames. In some embodiments, a machine learning model (e.g., a generative model, such as a generative adversarial network, a transformers-based model, etc.) may be trained using training examples to generate synthetic frames. Examples of training examples may include any video including a plurality of frames, as the model can use a portion of the frames in any video as a training data set with at least a portion of the remaining frames as desired frames for generation. Specifically, a machine learning model for generating synthetic frames of a medical video may, for example, be trained using any number of videos of wounds. The trained machine learning model may be used to analyze the first video. By way of example, in FIGS. 25A-C, the first video may include frames 2510 and 2530, as previously discussed. In some embodiments, at least one processor (e.g., processor 202 of mobile communications device 115 or device 145) may implement a machine learning model in analyzing the first video including frames 2510 and 2530 to generate a new frame, for example frame 2520(i). In another example, one or more synthetic frames may be generated to correspond to a particular point of view, for example as described herein.

In some embodiments consistent with the present disclosure, creating a new video may include modifying frames of the first video using at least one correction factor. For example, in some embodiments, creating a new video may include receiving a first correction factor associated with a first portion of the new video of the wound and second correction factor associated with a second portion of the new video of the wound, and wherein creating the new video of the wound includes modifying frames of the first portion of the new video of the wound based on the first correction factor and modifying frames of the second portion of the new video of the wound based on the second correction factor. A correction factor may include a factor that may be applied to a given output to correct for a known amount of error, for differing illumination conditions, for differing distances from the wound, for differing sizes of wounds, and so forth. In some disclosed embodiments, some of the properties of the desired result video may be known. For example, in some embodiments, machine learning models may be trained with training examples of medical videos to determine a known amount of error between properties of a result new video and a desired new video.

For example, in some embodiments, the amount of error between result illumination conditions of the new video and illumination of desired illumination conditions of a new video may be known. Accordingly, in some embodiments, a first correction factor corresponds to a first illumination condition and the second correction factor corresponds to a second illumination condition. By applying the correction factors to the new video, the desired illumination conditions for the new video may be achieved. In another example, the amount of error associated with a resulting distance of at least camera from a wound in a created new video may be known. Accordingly, in some embodiments, a first correction factor corresponds to a first distance from the wound and a known second correction factor corresponds to a second distance from the wound. By applying the correction factors to the first video, the desired distance of the camera from the wound as it appears in the created new video may be achieved.

As previously discussed, some embodiments may include analyzing at least one image of the wound to identify a first region of the wound corresponding to a first tissue type and a second region of the wound corresponding to a second tissue type. For instance, a wound may be segmented into regions based on different areas of the wound consisting of different types of tissues, thereby distinguishing between different portions of the wound with different tissue types (for example, using a semantic segmentation algorithm). To be clear, some embodiments include, determining the first portion of the new video of the wound based on the first region of the wound and a second portion of the new video of the wound based on the second region of the wound and determining the first correction factor based on the first tissue type and the second correction factor based on the second tissue type. In some embodiments, correction factors may be determined based on the same or different tissue types. In one example, each tissue type may be associated with a predetermined correction factor. In another example, a correction factor for a portion of the new video corresponding to a region of the wound and a tissue type may be determined based on a function of the tissue type and at least one additional parameter (such as a dimension of the region of the wound, a tissue type of another region of the wound adjacent to the region of the wound, an illumination condition, and so forth).

Figure 26:
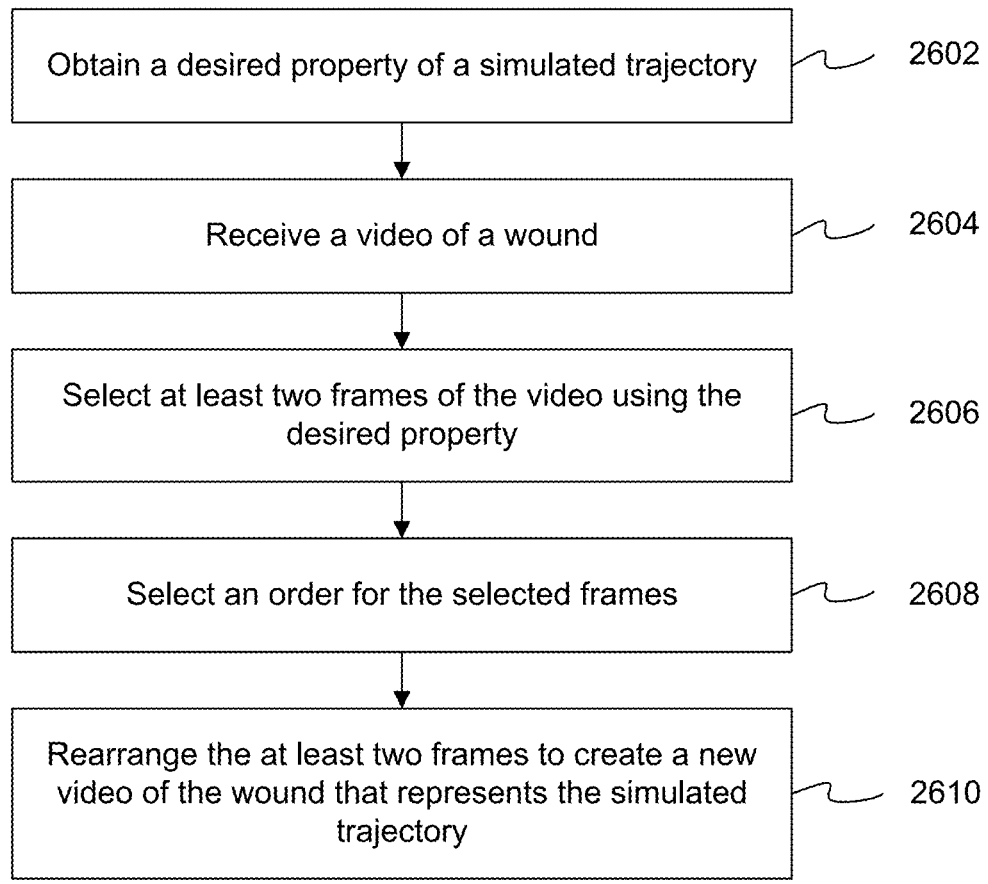
FIG. 26 is a flowchart of an example process for rearranging and selecting frames of medical videos, consistent with some embodiments of the present disclosure.

FIG. 26 is a flowchart of an example process 2600 for rearranging and selecting frames of medical videos including steps 2602 through 2610. Steps 2602 through 2610 may be executed by at least one processor (e.g., processing device 202 of server 145 or mobile communications device 115 of FIG. 2), consistent with some embodiments of the present disclosure.

Process 2600 may begin with step 2602. At step 2602, the at least one processor may obtain a desired property of a simulated trajectory (e.g., simulated trajectory 2550 in FIGS. 25A-C) of a virtual camera (e.g., virtual camera 226(i) of virtual mobile communications device 226(i) in FIG. 25C).

Once the desired property has been obtained, process 2600 may proceed to step 2604. At step 2604, the at least one processor may receiving a first video of a wound (e.g., wound 2500) captured by a moving camera (e.g., image sensor 226), the first video including a plurality of frames (e.g., frames 2510, 2520, 2530).

After the first video including a plurality of frames has been received, process 2604 may proceed to step 2606. At step 2606, the at least one processor may use the desired property of the simulated trajectory of the virtual camera to analyze the first video to select at least two frames (e.g., frames 2510 and 2530) of the plurality of frames corresponding to the simulated trajectory of the virtual camera. At step 2608, the at least one processor may further use the desired property of the simulated trajectory of the virtual camera to select an order for the selected at least two frames. Finally, at step 2610, the at least one processor may rearrange the at least two frames based on the selected order to create a new video of the wound that represents the simulated trajectory of the virtual camera.

Embodiments consistent with the present disclosure provide systems, methods, devices, and computer readable media storing instructions for capturing and analyzing images to providing wound capturing guidance. In one example, consistent with the disclosed embodiments, an exemplary system may receive one or more images depicting a wound or other tissue feature from at least one image sensor. A "wound" as referred to herein may include any injury to the human body. For example, wounds may be open wounds resulting from penetration (e.g., puncture wounds, surgical wounds and incisions, thermal, chemical, or electric burns, bites and stings, gunshot wounds, etc.) and/or blunt trauma (e.g., abrasions, lacerations, skin tears), or they may include closed wounds (e.g., contusions, blisters, seromas, hematomas, crush injuries, etc.). Some non-limiting examples of a wound may include a chronic wound, acute wounds, ulcer (such as venous ulcer, arterial ulcer, diabetic ulcer, pressure ulcer, etc.), infectious wound, ischemic wound, surgical wound, radiation poisoning wound, and so forth. Based on an analysis of the images, the exemplary system may provide, through a user interface, guidance to place the wound in a desired position in the imaging frame and/or move a device associated with the at least one image sensor in a desired direction and/or to rotate the device in a desired way. By way of example, in FIG. 27, communications device 115 may be configured with a user interface that may guide the user to capture additional desired images of wound 2700 by repositioning wound 2700 in the image frame or to move communications device 115 in a desired direction based on an analysis of one or more original images captured by image sensor 226 (not shown in FIG. 27) and/or motion data provided by motion sensor 228 (not shown in FIG. 27) in communications device 115.

Figure 27:
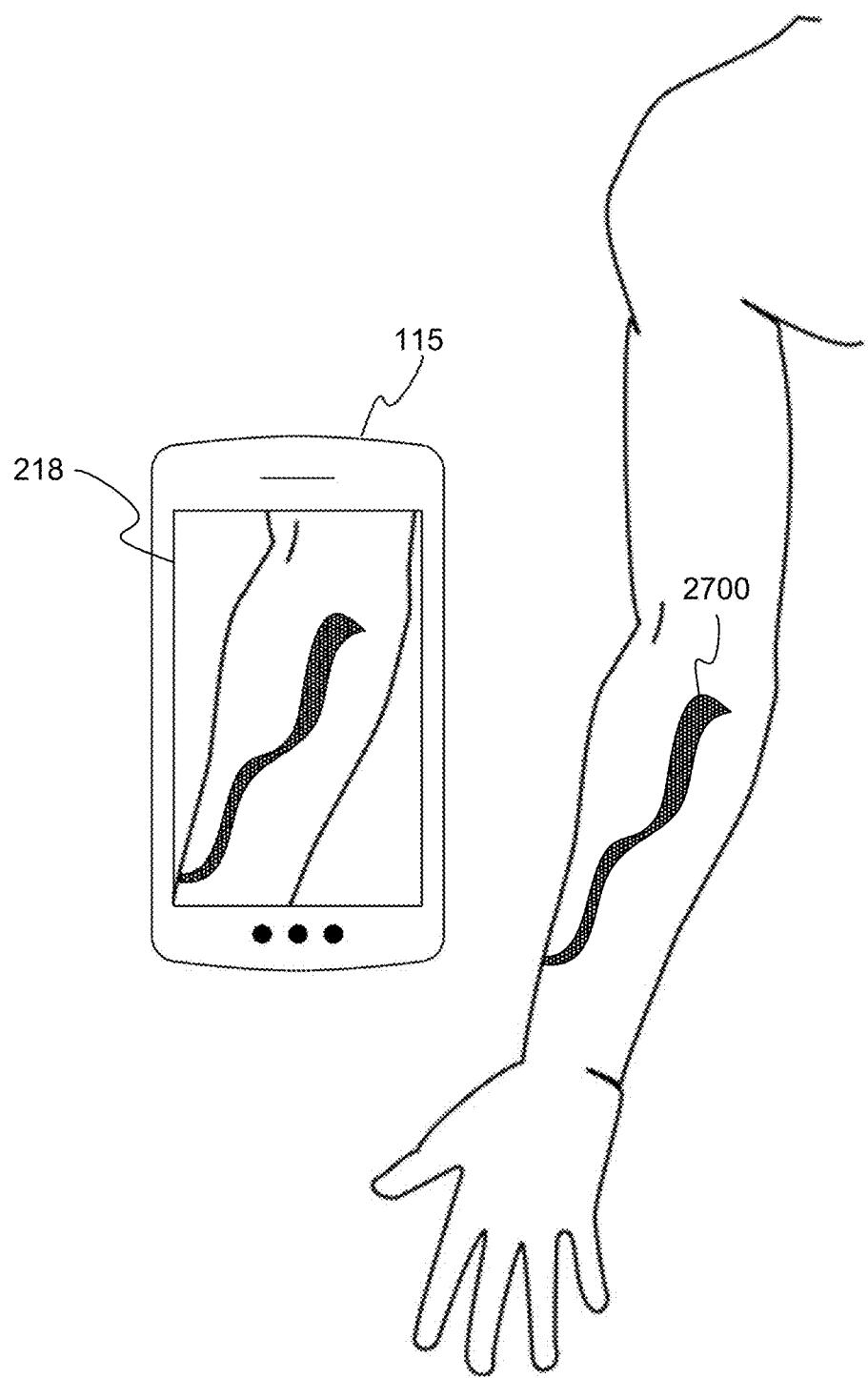
FIG. 27 is an illustration of a mobile communications device capturing an image of an example wound on the arm of a patient, consistent with some embodiments of the present disclosure.

Embodiments consistent with the present disclosure may include receiving a plurality of frames from at least one image sensor associated with a mobile device, at least one of the plurality of frames containing an image of a wound. A plurality of images may refer to multiple individual images captured individually at different times, or it may refer to a plurality of images captured as a continuous video feed. By way of example, in FIG. 27, a plurality of images captured by communications device 115 may be received (e.g., the image displayed by communications device 115 as illustrated in FIG. 27, or the images in FIG. 29 displayed on mobile communication device 115 in the positions denoted as 115(1)-(3)). At least one of the images may include wound 2700 or a portion thereof.

Embodiments consistent with the present disclosure may include displaying, on the mobile device, a real time video including at least a portion of the plurality of frames and a visual overlay indicating a desired position of the wound. For example, a user interface on a mobile communications device may display a live video feed captured from at least one image sensor of the device. On the user interface, the device may also display a visual indication of a position on the video feed at which the image of the wound should be positioned. For example, in some embodiments, the visual overlay may include an indication of a desired position for a center of the wound, or the visual overlay may include an indication of a bounding shape for the wound in the image or video. The indication of the desired position for the center of the wound may be in the form of crosshairs, pointed arrows, a dot, or any other visual element appropriate for designating a desired position on a display. The bounding shape for the wound may be a simple shape, such as a circle, square, or other polygon, or it may be a shape that is generated to closely resemble the shape of the wound.

Figure 28A:
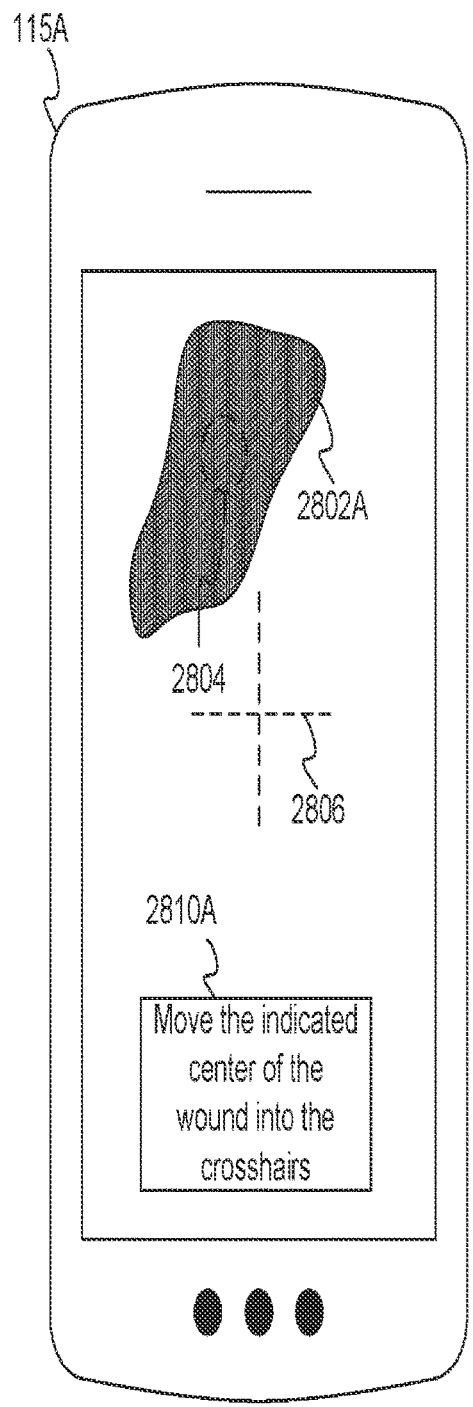
FIG. 28A is an illustration of a mobile communications device displaying an example overlay on an image of a wound, consistent with some embodiments of the present disclosure.
Figure 28B:
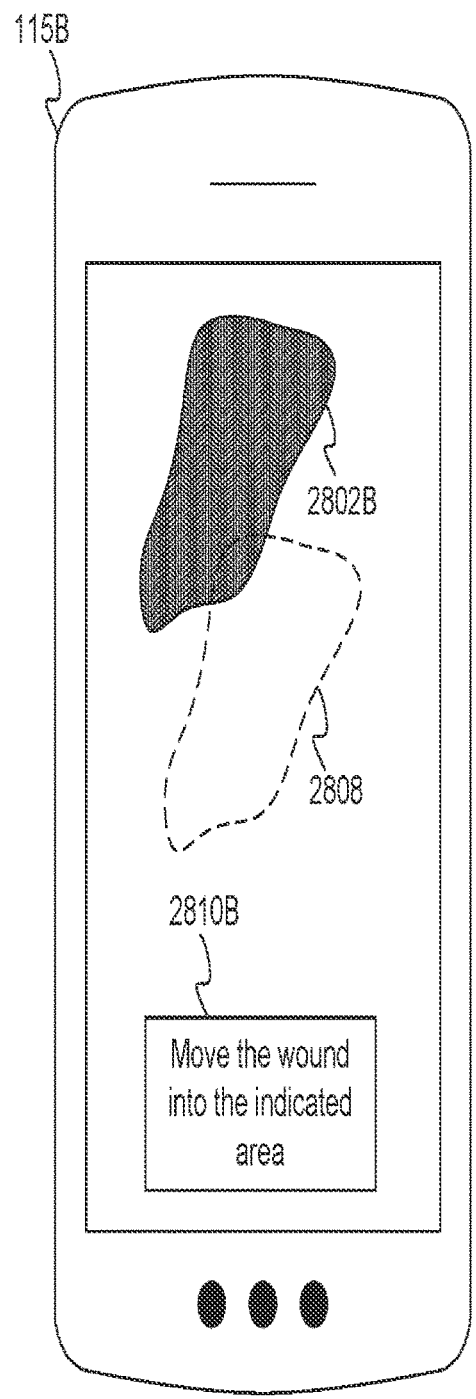
FIG. 28B is another illustration of a mobile communications device displaying an example overlay on an image of a wound, consistent with some embodiments of the present disclosure.

By way of some non-limiting examples, FIGS. 28A and 28B illustrate communication devices 115A and 115B displaying images of wounds 2802A and 2802B, respectively, and indications of desired positions thereof. For example, in FIG. 28A, the overlay of communications device 115 includes an indication 2804 of the center of wound 2802A and crosshairs 2806 indicating a desired position of the center of the wound. In FIG. 28B, the overlay of communications device 115 includes an indication of a bounding shape 2808 of wound 2802B indicating the desired position of the wound. Furthermore, although the term "indication" is typically used herein as being displayed on a mobile device, this descriptive use is for illustrative purposes only. For example, indications may also include audible and/or tactile indications and may be provided on systems other than a mobile device (e.g., through external monitors, speakers, augmented reality systems, virtual reality systems, etc.). Thus, it is to be understood that the foregoing illustrative descriptions are not meant to limit the present disclosure to certain embodiments that utilize a physical display to provide indications.

Embodiments consistent with the present disclosure may include detecting, based on at least part of the plurality of frames, that the wound is in the desired position. For example, the at least part of the plurality of frames used for the detection may be identical to the displayed at least a portion of the plurality of frames or may differ from the displayed at least a portion of the plurality of frames. For example, the at least part of the plurality of frames used for the detection and the displayed at least a portion of the plurality of frames may have all frames in common, may have no frames in common, may have some but not all frames in common, and so forth. In some examples, a mobile communications device imaging the wound may perform an analysis on the captured images to determine whether the wound is in a desired position, or it may determine that it is in a desired position based on the relative position of the wound in the overlay of the mobile communications device with respect to an indication of the desired position. For example, a machine learning model may be trained using training examples to determine whether the wounds are in desired positions in image frames. An example of such training example may include a sample image of a sample wound and an indication of a sample desired position for the sample wound in the sample image, together with a label indicating whether the sample wound is in the sample desired position. The trained machine learning model may be used to analyze the at least part of the plurality of frames to detect that the wound is in the desired position or that the wound is not in the desired position. In other examples, object detection algorithm may be used to analyze the at least part of the plurality of frames to determine an actual position of the wound in the at least part of the plurality of frames, and the actual position may be compared with the desired position to detect that the wound is in the desired position or that the wound is not in the desired position. If the wound is not in the desired position, embodiments consistent with the present disclosure may include displaying an indication to correct an actual position of the wound in the video. Once the actual position of the wound is corrected, the display of the indication to correct the actual position of the wound in the video may be halted, or an additional indication indicating that the position has been corrected may be displayed.

By way of some non-limiting examples, FIGS. 28A and 28B illustrate communication devices 115A and 115B displaying images of wounds 2802A and 2802B in incorrect positions and displaying indications to correct the actual positions of the wounds. For example, in FIG. 28A, communications device 115A may detect that wound 2802A is not in the desired position because the center 2804 of wound 2802A is not aligned with crosshairs 2806. In response, communications device 115A may display indication 2810A, prompting the user "to move the indicated center of the wound into the crosshairs." Once center 2804 has been aligned with the crosshairs 2806, communications device 115A may remove indication 2810A or replace it with an indication that wound 2802A is in the desired position. In FIG. 28B, communications device 115B may detect that wound 2802B is not in the desired position because it does not coincide with the bounded shape of the wound 2808. In response, communications device 115B may display indication 2810B, prompting the user to "move the wound into the indicated area." Once wound 2802B coincides with bounded area 2808, communications device 115B may remove indication 2810B or replace it with an indication that wound 2802B is in the desired position.

In some embodiments, image analysis may include calculating a convolution of the at least part of the plurality of frames to derive a result value of the calculated convolution, for example as described above. In some embodiments, the derived result value of the calculated convolution may be used to determine an actual position of the wound. In one example, in response to a first result value of the calculated convolution, a first actual position of the wound may be determined, and in response to a second result value of the calculated convolution, a second actual position of the wound may be determined, the second position may differ from the first position. In another example, the determined actual position of the wound may be a function of the result value of the calculated convolution. Some non-limiting examples of such function may include a linear function, a non-linear function, a polynomial function, a logarithmic function, an exponential function, a continuous function, a non-continuous function, a monotonic function, a non-monotonic function, and so forth. In yet another example, the derived result value may be used to determine a position of a certain element of the wound (e.g., center 2804 of wound 2802A in the image displayed on communications device 115A) or the edge or boundary of a wound (e.g., the boundary of wound 2802B in the image displayed on communications device 115B), or any other position associated with the wound. Once the actual position of the wound has been determined, the actual position may be compared with the desired position of the wound (e.g., the positions indicated by crosshairs 2806 or boundary 2808) to detect that the wound is in the desired position. In some embodiments, this detection may be based on the difference between the actual position of the wound and the desired position being greater than a threshold value (e.g., by a number of pixels or other coordinate values).

Some embodiments may include detecting that the wound is not in the desired position for at least a specified period of time and, in response, displaying an indication to correct an actual position of the wound in the video. For example, when it is determined that a wound is not in a desired position within a frame based on an analysis of at least a part of the plurality of frames captured, an indication to correct the actual position of wound may not be displayed until it has not been in the desired position for a predetermined amount of time (e.g., 0.5 s, 1 s, 2 s, 5 s, etc.). By way of example, in FIG. 28B, indication 2810B may be displayed if the actual position of 2802B on the display of mobile communications device 115B does not coincide with bounded area 2808 for two seconds. Prior to the expiration of those two seconds, indication 2810B may not be displayed.

Embodiments consistent with the present disclosure may include displaying an indication on the mobile device to move the mobile device in a desired direction. For example, in some situations, the size, shape, and/or positioning of the wound may require a user to make additional movements with the mobile device to capture additional images in order to collect as much information from the imaged wound as possible. In some non-limiting examples, the displayed indication may be textual, graphical, a combination of a text with graphics, and so forth. In another non-limiting example, the indication may be provided audibly. By way of example, in FIGS. 27 and 29, the patient is inflicted with wound 2700 extending from the base of the patient's forearm to the radial side of the patient's wrist. In such situations, a single image of the wound may not provide sufficient information for a computerized system or a physician to make an effective evaluation of the wound's condition. For example, an image taken directly above and perpendicular to the posterior portion of a forearm may not provide much valuable information regarding the portion of the wound on a radial side of the patient's wrist, and no information whatsoever regarding any portions of the wound on the anterior side of the patient's forearm. Thus, it may be necessary to capture a series of images to capture the entirety of the wound. In some embodiments, once a portion of the wound is in the desired position on the user interface of the mobile device, the mobile device may display an indication to prompt the user to move the device in order to capture additional images. The displayed indication may include directions to move the mobile device in one or more directions in three dimensions and/or rotate the mobile device about one or more axes. In general, a "desired direction" may include any directional or rotational trajectory.

Figure 29:
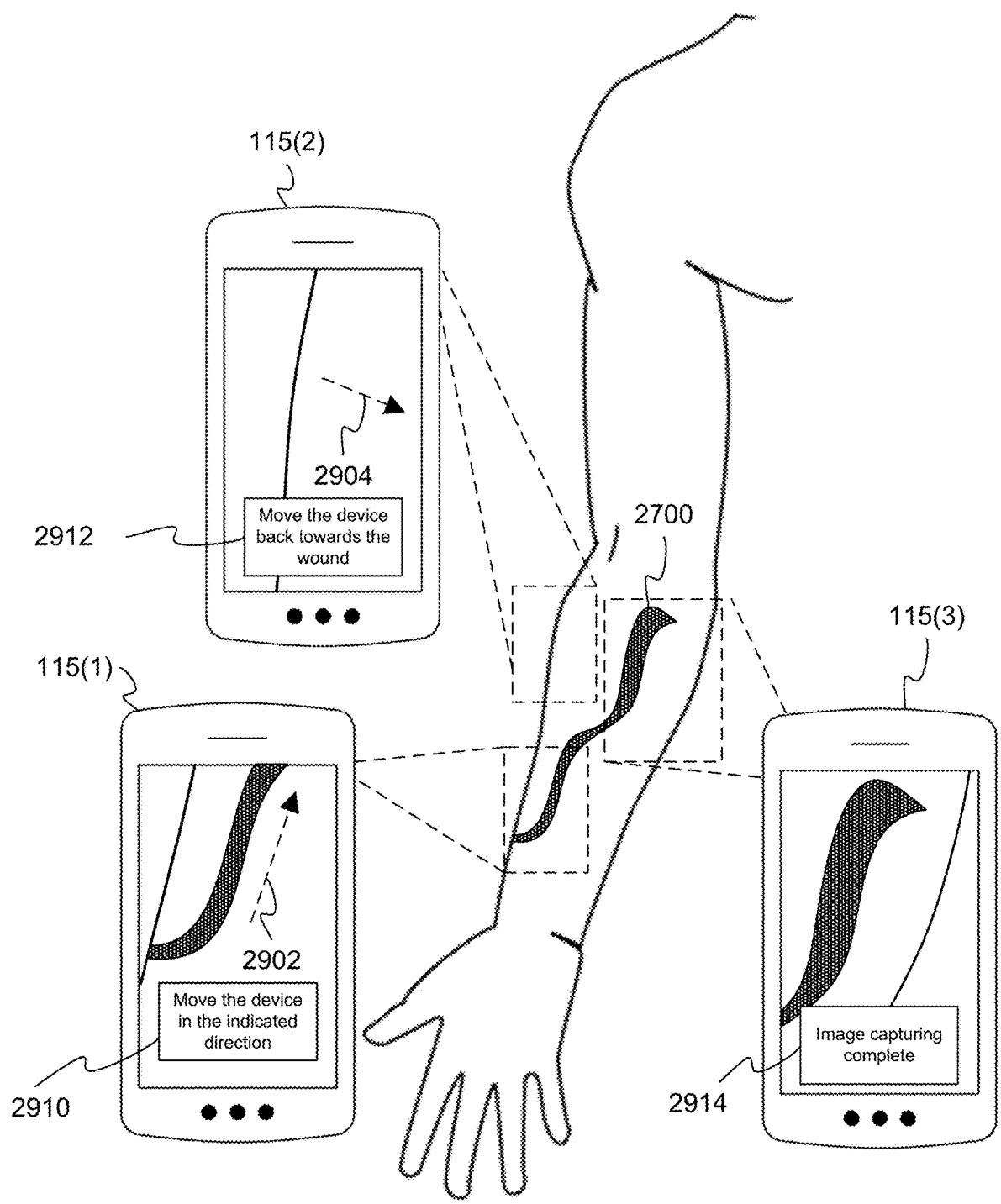
FIG. 29 is an illustration of a mobile communications device capturing a series of images in different positions of an example wound on the arm of a patient, consistent with some embodiments of the present disclosure.

By way of example, FIG. 29 illustrates the capturing of a plurality of images of wound 2700 by moving communications device 115. Notation mark 115(1) denotes communications device 115 in a first position, in which the user has moved the actual position of the wound to the initial desired position on the user interface. In response to the actual position of the wound being in the desired position, communications device 115 may display indication 2910 prompting the user to "move the device in the indicated direction" (or the like) and a direction arrow 2902 directing the user to the desired rotation. Although the direction arrow 2902 is illustrated as two-dimensional herein, it is to be understood that the provided direction can be configured to appear three-dimensional, consistent with disclosed embodiments and at least the capabilities of conventional display and computation devices. For example, direction arrow 2902 and indication 2910 can be configured to prompt the user to rotate the mobile device along one or more axes in addition to prompting the user to move the device in one or more directions.

Embodiments consistent with the present disclosure may include receiving motion data from at least one motion sensor associated with the mobile device. Motion sensors (e.g., motion sensor 228 depicted in FIG. 2) may include accelerometers, gyroscopes, or any other sensor configured to measure acceleration, gravity, speed of revolution, curl vector values, or drift of the mobile device. In some embodiments, the motion may be determined, at least in part, based on an analysis of the plurality of images captured by the at least one image sensor (e.g., image sensor 226 depicted in FIG. 2) of the mobile device, for example by analyzing the plurality of images with an egomotion algorithm. In this sense, an image sensor may also be considered to be a motion sensor.

Based on the received motion data, embodiments consistent with the present disclosure may include detecting that the mobile device has moved in the desired direction. For example, in some embodiments, a direction of the actual movement of the mobile device may be determined at least in part on motion data received from the at least one motion sensor, and the direction of the actual movement may then be compared with the desired direction to determine whether the mobile device is moving in the desired direction. In some embodiments, this determination may be made upon the direction of the actual movement the mobile device exceeds a predetermined tolerance. That is, the desired movement may be considered to include a range of directions, such that the mobile device may be determined to be moving in the desired direction if the direction of actual movement is within a given range of angles from a desired direction.

By way of example, in FIG. 29, communications device 115 may include at least one motion sensor (e.g., image sensor 226 and motion sensor 228, not shown in FIG. 29) that may generate motion data that can be utilized to determine the direction of actual movement of communications device 115 as a user moves its position according to indication 2910 and the direction arrow 2902. When communications device 115 has moved in the correct direction (e.g., by moving to the position denoted with 115(3)), it may be determined that communications device 115 has moved in the desired direction because it has moved in a direction within a predetermined tolerance (e.g., within 1 degree, 5 degrees, 15 degrees, 30 degrees, etc.) of the indicated desired direction indicated by arrow 2902.

Some embodiments consistent with disclosed embodiments may include detecting that the mobile device has moved in a direction different from the desired direction and, in response, displaying an indication on the mobile device to correct the movement of the mobile device. For example, as described above, the motion data collected by the one or more motion sensors of the mobile device may be used to determine the direction of actual movement. If the actual direction of movement is not the same as (or exceeds a predetermined tolerance of) the desired direction, it may be accurately determined that the mobile device has moved in an incorrect direction, and the mobile device can accordingly provide an indication to correct the movement of the mobile device. By way of example, in FIG. 29, when communications device 115 has moved in a different direction than the desired direction (e.g., by moving to the position denoted with 115(2), where the wound is no longer in the collected image, or when mobile device 115 has moved in a direction differing from desired direction 2902 in excess of a predetermined tolerance), communications device 115 may be configured to display an indication 2912 directing the user to move communications device 115 in direction 2904, thereby correcting the movement of communications device 115(2). In some non-limiting examples, the displayed indication may be textual, graphical, a combination of a text with graphics, and so forth. In another non-limiting example, the indication may be provided audibly.

Embodiments consistent with the present disclosure may include displaying an additional indication on the mobile device when the mobile device has moved in the desired direction. In some embodiments, the indication may be that the needed images have been captured or that image capturing of the wound has been completed. Alternatively, in some embodiments, additional imaging of the wound in one or more different directions may be required to collect all of the necessary information (e.g., where the wound is elongated and extends in multiple longitudinal directions, where the wound cannot be entirely imaged by moving the mobile device in one direction due to size, etc.). Accordingly, in some embodiments, the additional indication may include an instruction to move the mobile device in a different direction. In some embodiments, once all imaging of the wound has been completed due to the mobile device being moved in one or more desired directions (e.g., along a desired trajectory), the captured image data and motion data may be used to construct a three-dimensional model of the wound. Further, some embodiments may include generating a user rating based on an analysis of at least one frame of the plurality of frames. The user rating may include a score, a percentage, or any other metric indicative of the user's actual positioning and/or movement of the mobile device relative to the desired positions and/or directions indicated by the mobile device. The user rating may, for example, be based on a comparison between the actual positions and movements of the mobile device and the desired positions and movements of the mobile device. In some non-limiting examples, the additional indication may be textual, graphical, a combination of a text with graphics, and so forth. In another non-limiting example, the additional indication may be provided audibly.

By way of example, in FIG. 29, once communications device 115 has moved in a direction consistent with a desired direction indicated by arrow 2902 (e.g., by moving to the position denoted with 115(3)), communications device 115 may display an indication 2914 notifying the user that imaging has been completed. Alternatively, if imaging has not been completed (e.g., because wound 2700 continues to extend in one or more directions), indication 2914 displayed by communications device 115 may notify the user to move the device in an additional desired direction (e.g., similar to indication 2910 to move communications device 115 in desired direction 2902). Once imaging has been completed, communications device 115 or another system communicatively coupled to communications device 115 may use the collected image and/or motion data to generate a three-dimensional model of wound 2700. Additionally, communications device 115 may be configured to generate and/or display a rating of the user, based on the actual movement of communications device 115 matching or not matching the indicated desired direction 2902 (and/or the actual positions matching or not matching the positions indicated by crosshairs 2806 and/or boundary 2808).

Figure 30:
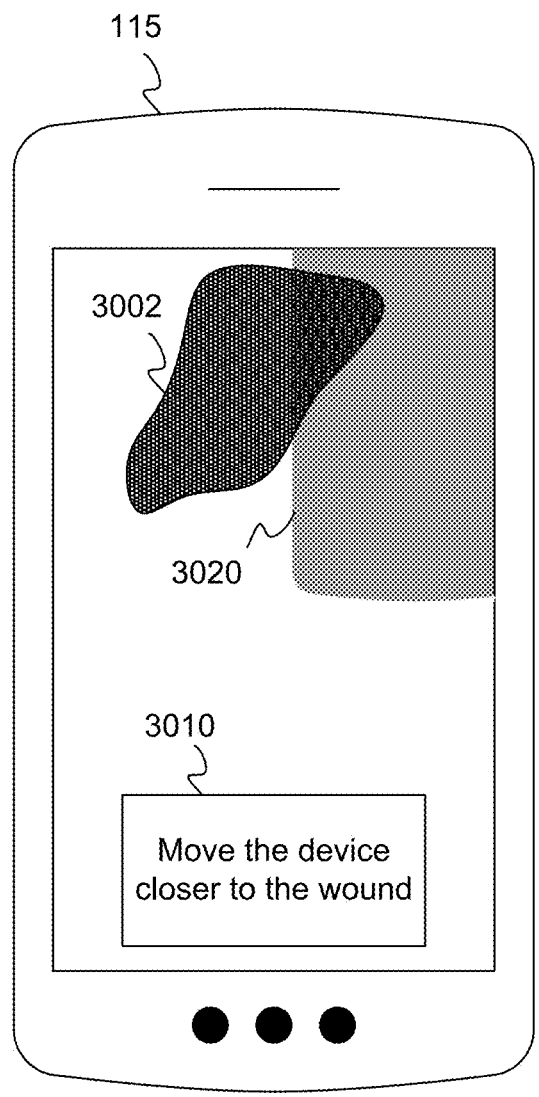
FIG. 30 is an illustration of a mobile communications device capturing an image of where a shadow is being cast over a wound of a patient, consistent with some embodiments of the present disclosure.

Embodiments consistent with the present disclosure may include providing guidance to improve illumination conditions. For example, some embodiments may include detecting, based on an analysis of at least one frame of the plurality of frames, that illumination conditions are not satisfactory and, in response, displaying an indication on the mobile device to take an action to improve the illumination conditions. As discussed previously herein, local illumination effects may result from the type of light source used to light the object, the distance of the object from the light source, a viewing angle of the object, position of the object, ambient light conditions, flash usage, exposure time, shadows, and so forth. For example, in some embodiments, at least one processor may be configured to derive at least one brightness and/or contrast value that fails to meet a predetermined threshold to meet satisfactory illumination conditions. Additionally or alternatively, in some embodiments, it may be determined that illumination conditions are not met if convolution values cannot be calculated with a predetermined threshold value of certainty (e.g., 90%, 95%, etc.) based on a given image or plurality of images, By way of example, as illustrated in FIG. 30, illumination conditions may not be satisfactory based on detecting the presence of a shadow (e.g., shadow 3020) in one or more of frames in the plurality of frames and/or detecting that the shadow is cast over a wound (e.g., wound 3002) in the plurality of frames. Some embodiments may include: detecting, based on an analysis of at least one frame of the plurality of frames, the presence of a shadow in the plurality of frames; detecting that the shadow is cast over the wound in the plurality of frames; and determining, based on an analysis of the shadow in the plurality of frames, information related to an object casting the shadow. In some examples, a machine learning model may be trained using training examples to detect presence of shadows in images and/or videos. An example of such training example may include a sample image and/or a sample video, together with a label indicating whether the sample image and/or the sample video includes a shadow. At least one frame of the plurality of frames may be analyzed using the trained machine learning model to detect the presence of shadow in the plurality of frames. In other examples, histogram of at least a portion of the at least one frame of the plurality of frames may be analyzed, for example by comparing values of the histogram with thresholds, to detect the presence of shadow in the plurality of frames.

Some embodiments of the present disclosure may include determining, based on an analysis of the shadow in the plurality of frames, information related to an object casting the shadow. The information related to the object casting the shadow may, in some embodiments, include an identification of the object casting the shadow such as the mobile device, a hand holding the mobile device, or another object of medical significance (e.g., a dipstick, testing kit, or any other type of medical equipment). In other examples, the information related to the object casting the shadow may include at least one of a type of the object, a size of the object, a position of the object, or a shape of the object. Determining the information may include performing an analysis on the detected shadow to determining physical parameters of the shadow (e.g., size, distance, angle, shape, etc.) and correlating the physical parameters with pre-stored information associated with the physical parameters to identify the information related to the object casting the shadow. In some examples, a machine learning model may be trained using training examples to determine information related to objects casting shadows from images and/or videos of the shadows. An example of such training example may include a sample image of a sample shadow, together with a label indicating information related to an object casting the sample shadow. The trained machine learning model may be used to analyze shadow in the plurality of frames to determine the information related to the object casting the shadow. By way of example, determining the information may include calculating a convolution of shadow 3020 in the image captured by communications device 115 in FIG. 30 and deriving a result value of the calculated convolution indicative of the size, shape, and/or distance of shadow 3020. Correlating the result value to pre-stored information may including accessing at least one data structure (e.g., database 146) storing physical parameters associated with a plurality of objects (e.g., communications device 115, a hand, etc.). The result value may be compared with the physical parameters in the at least one data structure to determine that shadow 3020 is being cast by communications device 115.

Some disclosed embodiments may include determining a particular action based on the information associated with the object casting the shadow information and causing a performance of the particular action when the shadow is cast over the wound. The particular action may include any action that may be executed automatically by the mobile device (e.g., modifying at least one parameter associated with the at least one image sensor) or manually by the user (e.g., by moving the mobile device to a different location, moving the object casting the shadow so that it no longer casts a shadow on the wound, interacting with other elements of the environment, etc.) to directly or indirectly cause the unsatisfactory illumination conditions to improve and/or become satisfactory. The at least one parameter may include image resolution, frame rate, gain, ISO speed, stereo base, lens, focus, zoom, color correction profile, etc. associated with the image sensor (e.g., image sensor 226) of the mobile device. In some embodiments, if the illumination conditions are unsatisfactory due to low brightness, the particular action may include activating a flash feature associated with the mobile device or turning on one or more other lights in the particular room or environment. Causing a performance of the particular action may include automatically triggering the mobile device to take an action or by providing an indication to prompt the user to take a particular action.

By way of example, as discussed above with reference to FIG. 30, some embodiments may include detecting the presence of shadow 3020 being cast over wound 3002 and determining that the object casting the shadow is mobile device 115 or a hand holding mobile device 115. Based on this information, the performance one or more particular actions may be caused to thereby improve the unsatisfactory illumination conditions associated with shadow 3020. For example, the zoom, focus, or lens associated with image sensor 226 of mobile device 115 may be changed to improve contrast and/or brightness. Additionally or alternatively, mobile device 115 may display an indication prompting the user to move the object casting the shadow in one or more directions (e.g., by displaying indication 3010 prompting the user to "move the device closer to the wound" or the like) such that the object casting the shadow (e.g., mobile device 115) no longer casts a shadow over wound 3002.

Figure 31:
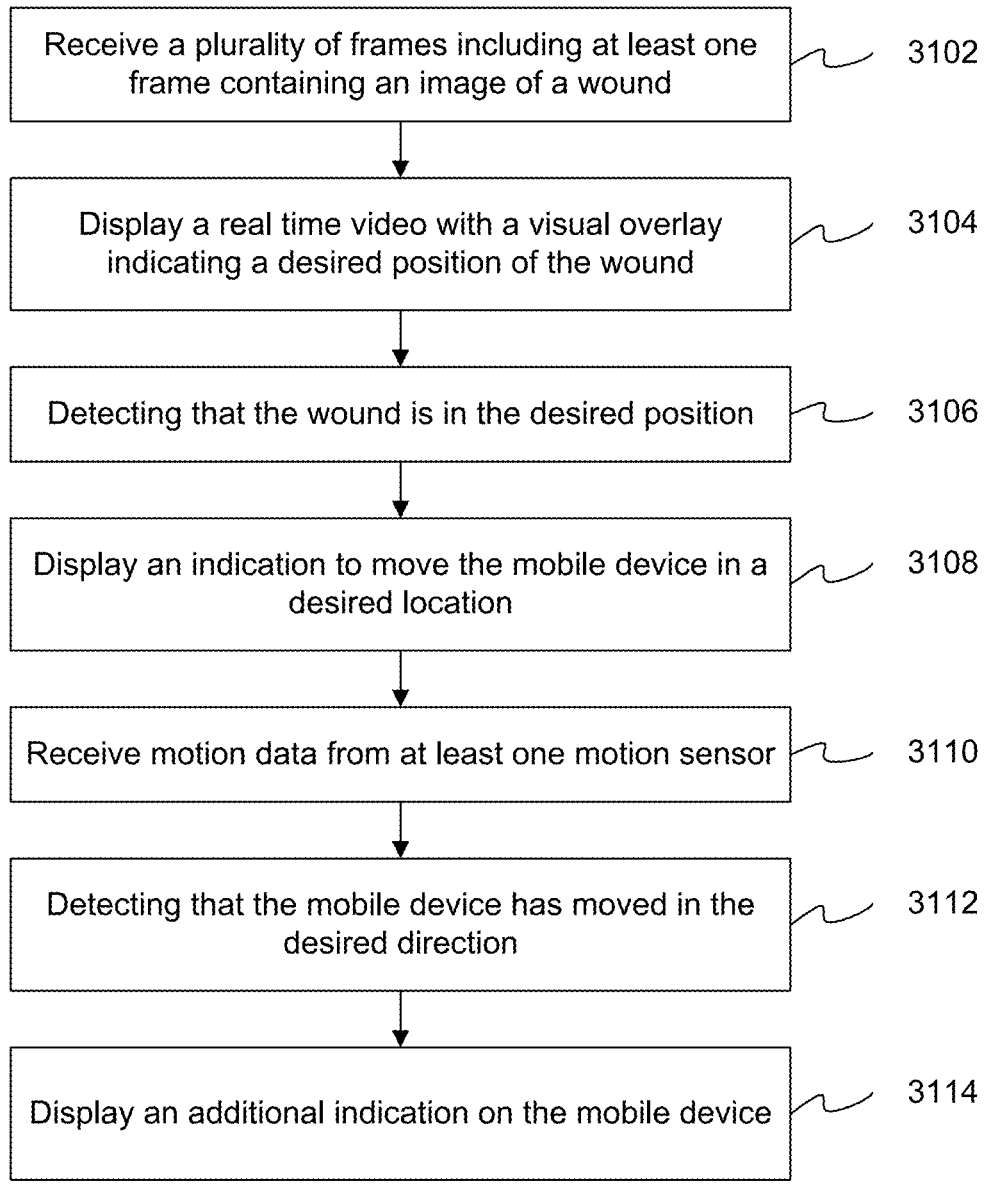
FIG. 31 is a flowchart of an example process for providing wound capturing guidance, consistent with some embodiments of the present disclosure.

FIG. 31 provides a flowchart of an example process 3100 for providing wound capturing guidance including steps 3102 through 3114. Steps 3102 through 3114 may be executed by at least one processor (e.g., processing device 202 of server 145 or communications device 115), consistent with some embodiments of the present disclosure.

Process 3100 may begin with step 3102. At step 3102, the at least one processor may receive a plurality of frames from at least one image sensor (e.g., image sensor 226) associated with a mobile device (e.g., communications device 115), at least one of the plurality of frames containing an image of a wound (e.g., wound 2700), consistent with some embodiments of the present disclosure. In other examples, receiving the plurality of frames by step 3102 may include at least one of reading the plurality of frames from memory, receiving the plurality of frames from an external device (for example, using a digital communication device), capturing the plurality of frames using the at least one image sensor, or generating the plurality of frames (for example, using a generative model).

Once the plurality of frames has been received, process 3100 may proceed to step 3104. At step 3104, the at least one processor may display a real time video including at least a portion of the plurality of frames and a visual overlay indicating a desired position of the wound on a display component of the mobile device (e.g., touch screen 218), consistent with some embodiments of the present disclosure. In some embodiments, the indication may alternatively or additionally be provided through audible or other means (e.g., with speaker 222).

At step 3106, the at least one processor may detect that the wound is in the desired position based on at least part of the plurality of frames, consistent with some embodiments of the present disclosure. For example, the at least one processor may detect that wound 2802A is in the desired location due to its center 2804 coinciding with crosshairs 2806 in the captured images or due to wound 2802B coinciding with bounded shape 2808, as illustrated in FIGS. 28A and 28B, respectively.

When the wound is in the desired position, process 3100 may proceed to step 3108. At step 3108, the at least one processor may provide an indication to move the mobile device in a desired direction, consistent with some embodiments of the present disclosure. For example, in FIG. 29, the at least one processor may cause communications device 115 to display indication 2910 prompting the user to move the device in the desired direction indicated by arrow 2902.

At step 3110, the at least one processor may receive motion data from at least one motion sensor (e.g., motion sensor 228) associated with the mobile device, consistent with some embodiments of the present disclosure. At step 3112, the at least one processor may detect that the mobile device has moved in the desired direction, consistent with some embodiments of the present disclosure. For example, in FIG. 29, the at least one processor may detect that communications device 115 has moved from the location denoted 115(1) to the location denoted 115(3) by moving in the desired direction initially indicated by arrow 2902. Alternatively, the at least one may detect that communications device 115 has moved in a direction that is different than the desired direction (e.g., by moving to the location denoted 115(2)).

When the mobile device has moved in the desired direction, process 3100 may proceed to step 3114. At step 3114, the at least one processor may provide an additional indication, consistent with some embodiments of the present disclosure. For example, in FIG. 29, the at least one processor may cause mobile communications device 115 to display indication 2914 once communications device has moved in the desired direction to the location denoted by 115(3). Alternatively, the at least one processor may cause communications device 115 to display indication 2912 if communications device 115 moves in an incorrect direction to the location denoted by 115(2).

Figure 32:
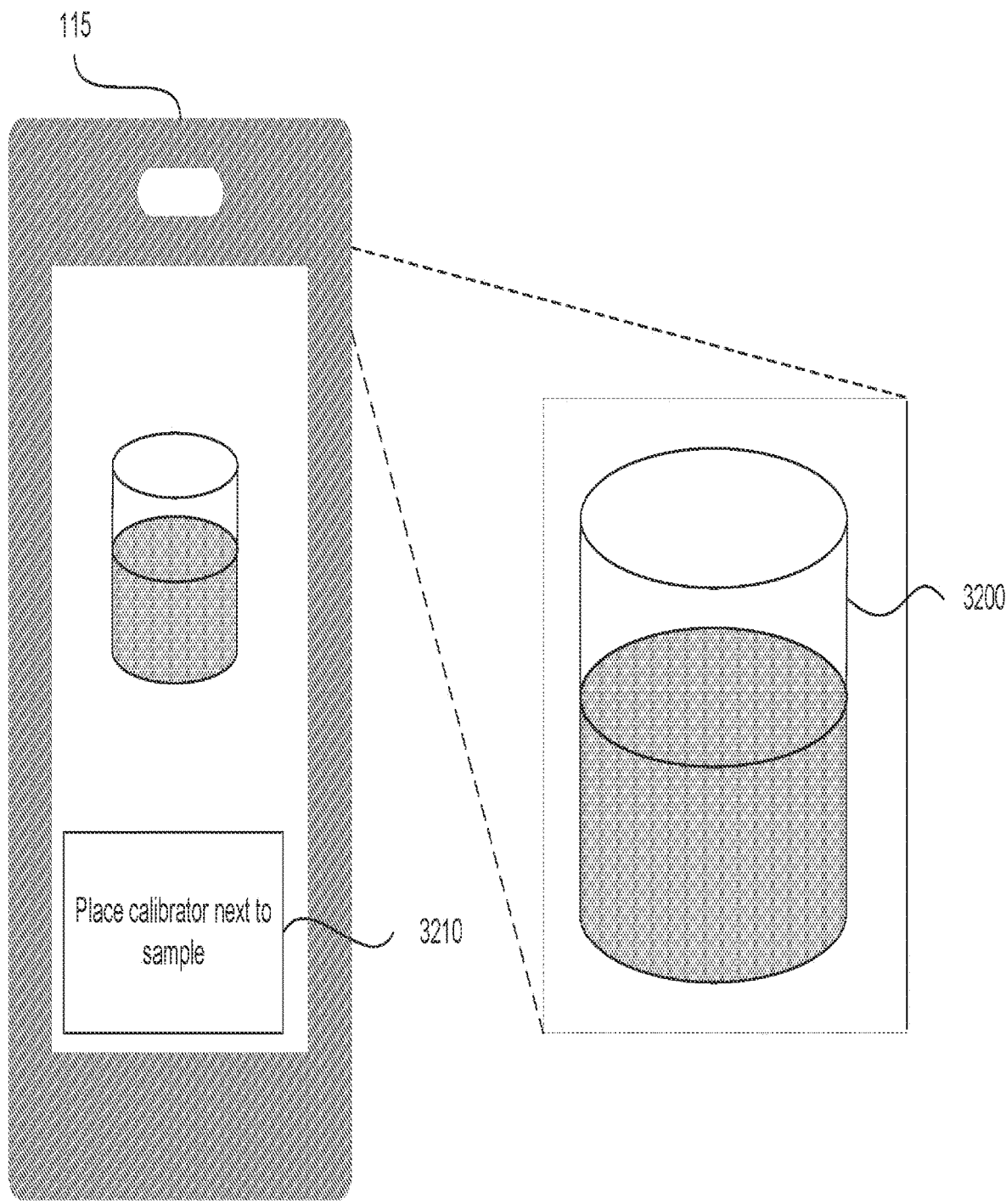
FIG. 32 is an illustration of a mobile device with a user interface for guiding a user through a series of steps in a medical image capturing application, consistent with some embodiments of the present disclosure.

Embodiments consistent with the present disclosure provide systems, methods, devices, and computer readable media storing instructions for selective reaction to a failure to successfully complete a medical action using a medical image capturing application. As used herein, a medical image capturing application may include an application programmed into a user device (e.g., a computer, smartphone, tablet, etc.) configured to capture one or more images during medical testing, evaluation, and/or treatment. In some embodiments, a medical image capturing application may be configured to perform an analysis on the one or more captured images. The medical image capturing application may, in some embodiments display or otherwise provide a user interface on the device, the user interface being configured to guide a patient through one or more steps for performing a medical action. As used herein, a medical action may include any action in association with the medical testing, evaluation, and/or treatment of an individual patient and may be completed or attempted by a medical professional, the patient themselves, or by any other caregiver. By way of example, FIG. 32 illustrates a mobile communications device 115 with a medical image capturing application programmed thereon, consistent with some disclosed embodiments. The user interface of device 115 may allow a user to capture images in a medical setting, for example, images of medical sample 3200. Moreover, the image capturing application may guide the user through a series of steps, for example by displaying indication 3210 guiding the user to place a calibration element next to the medical sample, by displaying other visual indications, by providing audible guidance to the user, and so forth.

Figure 33:
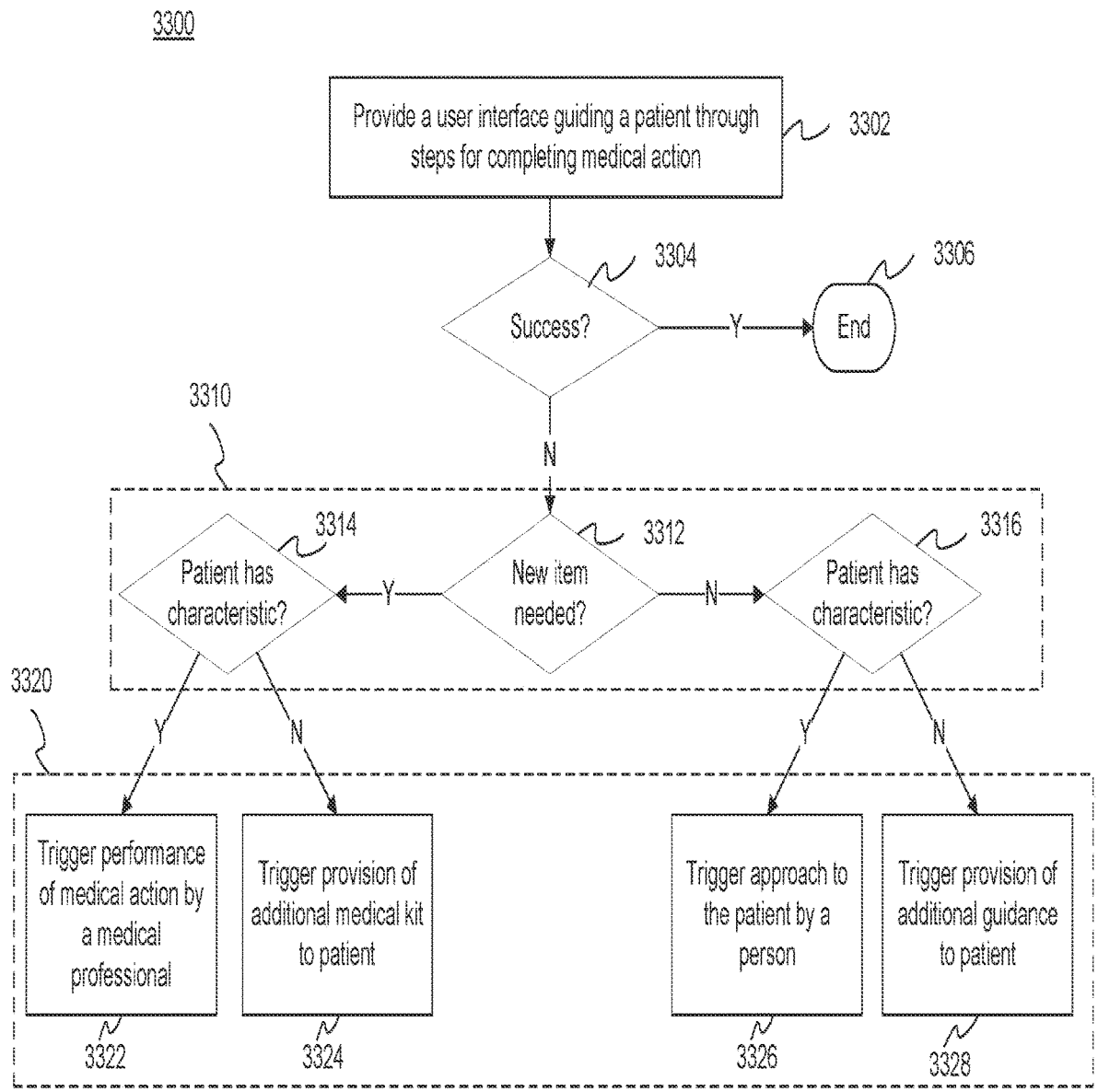
FIG. 33 is a flowchart of an example process for selective reaction to a failure to successfully complete a medical action using a medical image capturing application, consistent with some embodiments of the present disclosure.

By way of further example, FIG. 33 provides a flowchart of an example process 3300 for selective reaction to a failure to successfully complete a medical action using a medical image capturing application including steps 3302 through 3328, consistent with some embodiments of the present disclosure. Steps 3302 through 3328 may be executed by at least one processor (e.g., processing device 202 of communications device 115 or server 145). Process 3300 may begin at step 3302. At step 3302, the at least one processor may provide a user interface for guiding a patient through steps for completing a medical action, as discussed above.

Consistent with disclosed embodiments, the plurality of steps may include using at least one item of a medical kit. The at least one item of a medical kit may include any medical items, such as disposable items used for treatment (e.g., bandages, gauze, tape, splints, saline solution, etc.), medications (pain reliever, antibiotics, ointments, etc.), medical testing equipment (e.g., sample containers, dipsticks, etc.), other medical equipment (e.g., scissors, sutures, tweezers, cold compresses, slings, etc.), or any other item associated with the provision of healthcare. For example, in some embodiments, the at least one item of the medical kit may include at least one of a dipstick (e.g., dipstick 450 depicted in FIG. 4B) and/or a calibrator (e.g., colorized surface 132 depicted in FIG. 1A). The plurality of steps may be completed by a medical professional, the patient, or any other caregiver. As used herein, a step may refer to any portion of a medical action provided as a direction to a user, or it may constitute the entire medical action. In some disclosed embodiments, for example, using at least one item of the medical test kit may include positioning a calibrator sticker, positioning a dipstick adjacent to a calibrator; dipping a dipstick in a medical sample, and/or blotting a dipstick. By way of example, in FIG. 32, the particular medical action may be a certain test of medical sample 3200, and one of the plurality of steps for completing the test may include placing a calibrator (e.g., colorized surface 132 in FIG. 1A) next to medical sample 3200, as provided in indication 3210 displayed on mobile communications device 115.

Consistent with disclosed embodiments, the plurality of steps for completing the medical action may include capturing at least one image of at least part of the at least one item of the medical kit using at least one image sensor associated with a mobile device. For example, the at least one step may include taking a photo or video of an item of medical test kit and/or a wound to be treated with the at least one item either before, during, or after completion of another step (e.g., applying a bandage, positioning a calibrator sticker or dipstick, dipping a dipstick in a medical sample, etc.). The at least one image may be captured, for example, with image sensor 226 of communications device 115, as illustrated in FIG. 2, and may be displayed on touch screen 218 and/or processed by processing device 202, as discussed previously herein.

Embodiments consistent with the present disclosure may include detecting a failure to successfully complete the medical action. In some embodiments, detecting the failure may be based on an analysis of the at least one captured image. For example, detecting the failure may include performing image processing on at least one captured image to determine whether the at least one image is consistent with a successful use of the at least one item of the medical kit, or whether the at least one image was captured correctly. In some embodiments, a convolution of a part of the at least one captured image to derive a result value may be calculated, as previously discussed herein, and the result value may be used to detect the failure. Using the result value to detect a failure to use at least one item of a medical kit may include, for example, comparing the calculated result value to a threshold (for example, to a threshold based on a sample image of the at least one item that was used properly and/or based on a sample image of the at least one item that was used improperly). In one example, in response to a first result value of the calculated convolution, a failure may be detected, and in response to a second result value of the calculated convolution, a detection of the failure may be avoided. In some examples, a machine learning model may be trained using training examples to detect failures to successfully complete medical actions from images and/or videos. An example of such training example may include a sample image, together with a label indicating whether the sample image corresponds to a failure to successfully complete a medical action. In one example, the trained machine learning model may be used to analyze the at least one captured image and detect the failure. A detection of a failure may occur, for example, during step 3304 of process 3300 in FIG. 33. Although step 3304 is illustrated as being subsequent to step 3302, a failure to complete a medical action may be detected during step 3302. For example, a failure may be detected before all of the plurality of steps are completed, or it may be detected after all of the plurality of steps are completed. If a failure is not detected, and thus the medical action is successfully completed, process 3300 may end at step 3306. Otherwise, if a failure is detected, process 3300 may proceed to step 3310 (including steps 3312 through 3316), which involves the selection of a reaction to the detected failure that is likely to bring a successful completion of the medical action, as discussed in further detail herein.

In some embodiments, for example, a machine learning model may be trained using training examples to determine whether the at least one item is in a position consistent with proper use relative to other reference positions in the at least one image frame. Examples of such training examples may include sample images of correctly used sample items of a medical kit (e.g., a properly applied bandage, a properly positioned dipstick and/or calibrator sticker, a medical sample container provided with a proper sample, etc.) and sample images of incorrectly used sample items (e.g., an improperly applied bandage, a dipstick and/or calibrator stick placed upside-down with respect to the proper position, empty or partially filled medical sample containers, etc., medical sample containers with a wrong type of sample, etc.). In some embodiments, training examples may also include sample images taken with correct parameters (e.g., high resolution, proper lighting, etc.) and sample images taken with incorrect parameters (e.g., low brightness, low resolution, etc.). The trained machine learning model may be used to analyze the at least part of the plurality of frames to detect that the user correctly used, or incorrectly used, the at least one item of the medical kit as instructed, or to detect whether the user correctly captured the at least one image as instructed. In other examples, an object detection algorithm may be used to analyze the at least part of the plurality of frames to determine an actual position of the at least one item in the at least part of the plurality of frames, and the actual position may be compared with a correct position of the at least one item to determine whether it was or was not properly used.

In some embodiments, detecting a failure may include identifying the particular failure that occurred. For example, detecting a failure may include at least one of detecting that the calibrator sticker is incorrectly positioned, that the dipstick is incorrectly positioned adjacent to the calibrator, that the dipstick is improperly dipped in the medical sample, and/or that the dipstick is improperly blotted. By way of example, as illustrated in FIG. 32, communications device 115 may display an indication 3210 to place a calibrator (e.g., colorized surface 132 in FIG. 1A) next to medical sample 3200. Additionally or alternatively, indication 3210 may include a prompt to blot a dipstick (e.g., dipstick 450 in FIG. 4B) in medical sample 3200 and/or to place the blotted dipstick next to the calibrator element. Subsequently, communications device 115 may provide guidance for an additional step to capture at least one image of the blotted dipstick next to the calibrator element. At least one processor (e.g., processing device 202 of communications device 115 or server 145 in FIG. 2) may perform image processing to detect a failure by determining that the dipstick was improperly dipped in the medical sample, for example due to a coloration of the dipstick being inconsistent with the coloration of a properly dipped dipstick. In some examples, an image classification algorithm may be used to analyze the at least one captured image and determine a type of the failure. For example, each class may correspond to a different type of failure, and the type of failure may be determined based on the class assigned to the at least one captured image by the image classification algorithm.

In some embodiments, detecting a failure may be based on a timing associated with a detected action performed by the user. For example, in some embodiments, the detected failure may include a failure to capture the at least one image within a particular time window, or it may include detecting that the user interface was shut down before completing at least one of the steps for performing a medical action. The particular time window may be based on a time of a physical action involving the at least one item (e.g., applying a bandage, collecting a medical sample, blotting a dipstick, etc.) and/or a time of user action in the user interface (e.g., an interaction with touch screen 216 of communications device 115 in FIG. 2, thereby confirming completion of at least one of the plurality of steps, causing at least one image to be captured, or shutting down the provided user interface). By way of example, it may only be possible for a valid result to be determined from a dipstick (e.g., dipstick 450 in FIG. 4B) within a window of 15 to 30 minutes after the dipstick has been blotted into medical sample 3200. Thus, at least one processor associated with communications device 115 (e.g., processor 202) may detect a failure to properly blot the dipstick if the user captures at least one image outside the 15 to 30 minute window.

Embodiments consistent with the present disclosure may include selecting, from one or more alternative reactions, a reaction to the detected failure likely to bring a successful completion of the medical action. Additionally, some disclosed embodiments may include providing instructions associated with the selected reaction. A reaction as referred to herein may include a medical action that is made in response to a failure to bring completion of the medical option that may remedy the error caused by the respective failure. For example, in some embodiments, alternative reactions may include triggering a provision of an additional medical kit to the patient, triggering an approach to the patient by a person, or triggering a provision of additional guidance to the patient using the user interface. Triggering a particular action as used herein may refer to causing a mobile device to automatically execute the action (e.g., automatically adjusting parameters of image sensor 226 of communications device 115), providing instructions on the particular mobile device prompting the user to perform the particular action, or by providing instructions through one or more external devices (e.g., in FIG. 1A, communications device 125 associated with medical practitioner 120, server 145 associated with medical analysis unit 140, communications device 165 associated with healthcare provider 160, communications device 175 associated with insurance company 170, etc.) to prompt the associated user to perform the particular action. For example, the provided instructions may be configured to cause the provision of an additional medical kit to the patient by another person (e.g., a medical professional or other caregiver such as medical practitioner 120) or to alert the person to approach the patient.

The one or more alternative reactions may be stored in at least one data structure, such as a database (e.g., database 146). In some embodiments, the plurality of alternative reactions may be mapped to one or more of a variety of different variables associated with the particular medical action and/or patient, and the selection of the alternative reaction may be based on the particular variables associated with the particular medical action and/or patient. For example, the selection of the reaction may be based on a type of the failure detected, a result of the detected failure, the particular step for performing a medical action failed, a characteristic of the patient, and/or other factors that may affect the appropriate response to a detected failure. In some embodiments, detecting a failure may include identifying the one or more failed steps for performing a medical action and selecting a reaction is based on the one or more failed steps identified.

A type of failure may refer to a categorization of the failure, such as whether the failed action was the use of at least one item of a medical kit or a failure to capture at least one image with the mobile device as instructed. Each different particular failure may have different results that may influence which alternative reaction should be selected. For example, a failure to capture an image due to poor lighting may not have negative results and may require a simple reaction (e.g., turn on a flash component of communications device 115). In such a situation, it may be most appropriate to simply guide the patient to perform the simple reaction than to trigger additional assistance by a medical professional. However, if the detected failure is one that is likely to cause an emergency (e.g., a failure that may result in substantial injury), then it may be more appropriate to have a medical professional (e.g., medical practitioner 120 in FIG. 1A) or other caregiver provide assistance to the patient. Characteristics of a patient may be stored in at least one data structure (e.g., database 146), and may include any demographic information, medical information, or any other factors associated with the patient that may increase or decrease the likelihood that they are able to follow provided instructions and/or perform a particular action. Some example characteristics may also include factors that affect the risk that the detected failure will result in further injury or complications. Some example characteristics may include age, sex, education, lifestyle factors, location (e.g., whether the patient is at home or at a certain type of hospital), whether the patient is handicapped, preexisting conditions, and the like.

A characteristic may refer to a single one of these characteristics, or it may refer to a given combination of characteristics associated with the patient. A reaction based on a characteristic of a patient may be based on historic statistical data that may be used to determine a certainty that a patient has a particular characteristic, and a characteristic may be attributed to a patient if the certainty level exceeds a certain threshold (e.g., 90%, 95%, etc.). The given characteristic or characteristics of the patient may also be used to determine an urgency level. In some embodiments, the determined urgency level may be used to schedule and prioritize medical actions between high urgency/risk patients and low urgency/risk patients. For example, if there is a lack of availability of medical professionals or other caretakers, a selected reaction to a failure resulting in an emergency will be given higher priority than if the selected reaction has low urgency.

In some embodiments, the selected reaction may depend on whether the failure necessitates a usage of an alternative item to the at least one item of the medical kit for a successful completion of the medical action. Moreover, the selected reaction may depend on whether the failure necessitates a usage of an alternative item that is not in the medical kit (e.g., because it has already been used). In one example, it may be determined that the failure necessitates the usage of the alternative item in response to a failure to capture the at least one image within a particular time window (for example, a failure to capture an image of a dipstick in a particular time window after dipping it in a sample, after receiving an instruction to dip it in the sample, after acknowledging that it was dipped in a sample, etc.). In another example, it may be determined that the failure necessitates the usage of the alternative item based on an analysis of the at least one image. For example, a convolution of a part of the at least one captured image may be calculated to derive a result value. In response to a first result value, it may be determined that the failure necessitates the usage of the alternative item, and in response to a second result value, it may be determined that the failure does not necessitate the usage of the alternative item. In another example, the at least one captured image may be analyzed to determine whether the at least one item is contaminated, and the necessitated usage of the alternative item may be determined in response to the determined contamination.

In some embodiments, the selected alternative reaction may be based on a combination of the factors discussed above. For example, as discussed above, embodiments consistent with the present disclosure may include determining that the failure necessitates a usage of an alternative item to the at least one item of the medical kit for a successful completion of the medical action. In one example, when the medical kit includes the alternative item, the selected reaction may include at least one of triggering an approach to the patient by a person or triggering a provision of additional guidance to the patient using the user interface. In another example, when the medical kit does not include the alternative item, the selected reaction may include at least one of triggering a provision of an additional medical kit to the patient or triggering a performance of the medical action by a medical professional. In some examples, determining that the failure necessitates the usage of the alternative item to the at least one item of the medical kit for the successful completion of the medical action may be based on the type of the failure. In one example, the type of the failure may be determined as described above. In one example, in response to a first type of failure, it may be determined that the failure necessitates the usage of the alternative item, and in response to a second type of failure, it may be determined that the failure does not necessitate the usage of the alternative item. In some examples, determining that the failure necessitates the usage of the alternative item to the at least one item of the medical kit for the successful completion of the medical action may be based on a property of a usage of the user interface. One example of such property may include a usage of a particular functionality of the user interface. Another example of such property may include a time duration associated with completion of an action using the user interface. In one example, the type of the failure may be determined as described above. In one example, in response to a first property of the usage of the user interface, it may be determined that the failure necessitates the usage of the alternative item, and in response to a second property of the usage of the user interface, it may be determined that the failure does not necessitate the usage of the alternative item.

By way of example, FIG. 33 provides a flowchart of an example process 3300 for selective reaction to a failure to successfully complete a medical action using a medical image capturing application, consistent with some embodiments of the present disclosure. If a failure is detected, as discussed previously, process 3300 may proceed to step 3310 (including steps 3312 through 3316), which involves selecting one of the one or more alternative reactions based on the availability of a necessary alternative item (e.g., step 3312) and patient characteristics (steps 3314 and 3316). For example, at step 3312, at least one processor (e.g., processor 202 of communications device 115 or server 145) may determine whether the particular detected failure necessitates the use of an alternative item in another medical kit. If the detected failure necessitates the use of an additional or alternative item in another medical kit that is not in the present medical kit, process 3300 may proceed to step 3314. For example, process 3300 may proceed to step 3314 if the selected reaction requires an additional dipstick or bandage because the dipstick or bandage available in the medical kit has already been used. If the detected failure does not necessitate the use of an additional item in another medical kit, then process 3300 may proceed to step 3316. For example, process 3300 may proceed to step 3316 if the additional item needed is already available in the present medical kit, or if an additional item is not required for the selected alternative reaction whatsoever.

As discussed above, embodiments consistent with the present disclosure may include determining that the failure necessitates a usage of an alternative item to the at least one item of the medical kit for a successful completion of the medical action. In one example, if the failure necessitates a usage of an alternative item and the patient has a first characteristic, a provision of an additional medical kit may be triggered. For example, the first characteristic may be indicative that the respective medical action will likely be completed upon providing the patient with an additional medical kit (e.g., because the patient is likely to complete the medical action). Accordingly, the additional medical kit will be provided for self-administration of the medical action by the patient. In another example, if the failure necessitates a usage of an alternative item and the patient has a second characteristic, the performance of the medical action by a medical professional may be triggered. For example, the second characteristic may be indicative that the respective medical action will not likely be completed upon providing the patient with an additional medical kit (e.g., because the patient is unlikely to be able to complete the medical action on their own). Accordingly, the medical action will be completed by a medical professional instead. In some examples, the characteristic of the patient may be determined by accessing a database including characteristics of patients. In another example, the characteristic of the patient may be read from memory, may be received from an external device, may be received from a user of the user interface (for example, from the patient, from a caregiver of the patient, etc.), and so forth. In yet another example, the characteristic of the patient may be determined based on an analysis of the interaction of the patient with the user interface. For example, a classification algorithm may be used to analyze the interaction and to classify the patient to different categories of patients.

By way of example, at step 3314 of process 3300, at least one processor (e.g., processor 202 of communications device 115 or server 145) may determine whether the patient has a particular characteristic indicative of the patient's inability to complete the particular medical action and proceed to step 3322. At step 3322, the at least one processor may trigger a performance of the medical action by a medical professional (e.g., medical practitioner 120) instead of the patient. Alternatively, if the patient does not have the particular characteristic or has another characteristic indicative of the patient's ability to complete the particular action, the at least one processor may proceed instead to step 3324, where it may trigger the provision of an additional medical kit to the patient.

As discussed above, some disclosed embodiments may include determining that the failure does not necessitate a usage of an alternative item to the at least one item of the medical kit for a successful completion of the medical action. In one example, if the failure does not necessitate the usage of an alternative item and the patient has a first characteristic, an approach to the patient by a person may be triggered. For example, the first characteristic may be indicative that the respective medical action will not likely be completed upon providing the patient with an additional medical kit (e.g., because the patient is unlikely to be able to complete the medical action on their own). Accordingly, the patient will be approached by another individual to help complete the medical action. In another example, if the failure does not necessitate the usage of an alternative item and the patient has a second characteristic, the provision of additional guidance to the patient using the user interface may be triggered. For example, the second characteristic may be indicative that the user will likely complete the medical action upon further instruction (e.g., because the patient is capable of following the additional instructions).

By way of example, at step 3316 of process 3300, at least one processor (e.g., processor 202 of communications device 115 or server 145) may determine whether the patient has a particular characteristic indicative of the patient's inability to complete the particular medical action. If the patient has the particular characteristic, process 3300 may proceed to step 3326. At step 3326, the at least one processor may trigger an approach to the patient by another person (e.g., medical practitioner 120 or another caregiver) to help the patient complete the medical action. Alternatively, if the patient does not have a first characteristic or has a second characteristic indicative of a capability to follow additional instructions, process 3300 may instead proceed to step 3328. At step 3328, the at least one process may trigger the provision of additional guidance to the patient through a user interface of device 115 (e.g., touch screen 218).

Embodiments consistent with the present disclosure may include systems, methods, devices, and computer-readable media storing instructions for displaying an overlay on wounds. As referred to herein, a wound may include any injury to the human body. For example, wounds may be open wounds resulting from penetration (e.g., puncture wounds, surgical wounds and incisions, thermal, chemical, or electric burns, bites and stings, gunshot wounds, etc.) and/or blunt trauma (e.g., abrasions, lacerations, skin tears), or they may include closed wounds (e.g., contusions, blisters, seromas, hematomas, crush injuries, etc.). Some non-limiting examples of a wound may include a chronic wound, acute wounds, ulcer (such as venous ulcer, arterial ulcer, diabetic ulcer, pressure ulcer, etc.), infectious wound, ischemic wound, surgical wound, radiation poisoning wound, and so forth.

An overlay as used herein may include one or more elements of a user interface that are superimposed on an image, a video, or on the environment. The overlay may be superimposed on the user interface, for example, by displaying an image on a user interface along with the overlay, or it may include displaying the overlay on the user interface such that it appears to be superimposed on the image as viewed directly by the user (e.g., augmented reality glasses). That is, an image as used herein may refer to an image that is displayed on a user interface, or it may merely refer to the manifestation of the visual perception of a subject. For example, an image may include an image of a subject displayed on a user interface, an image that is captured by an imaging device, or an image as viewed by the human eye. As used herein, an overlay or portions thereof may also be referred to as an indication, for example as an indication of a condition of a wound, that is superimposed on an image. However, in some embodiments, an overlay may also include one or more non-superimposed indications or elements in addition to one or more superimposed elements.

Figure 34:
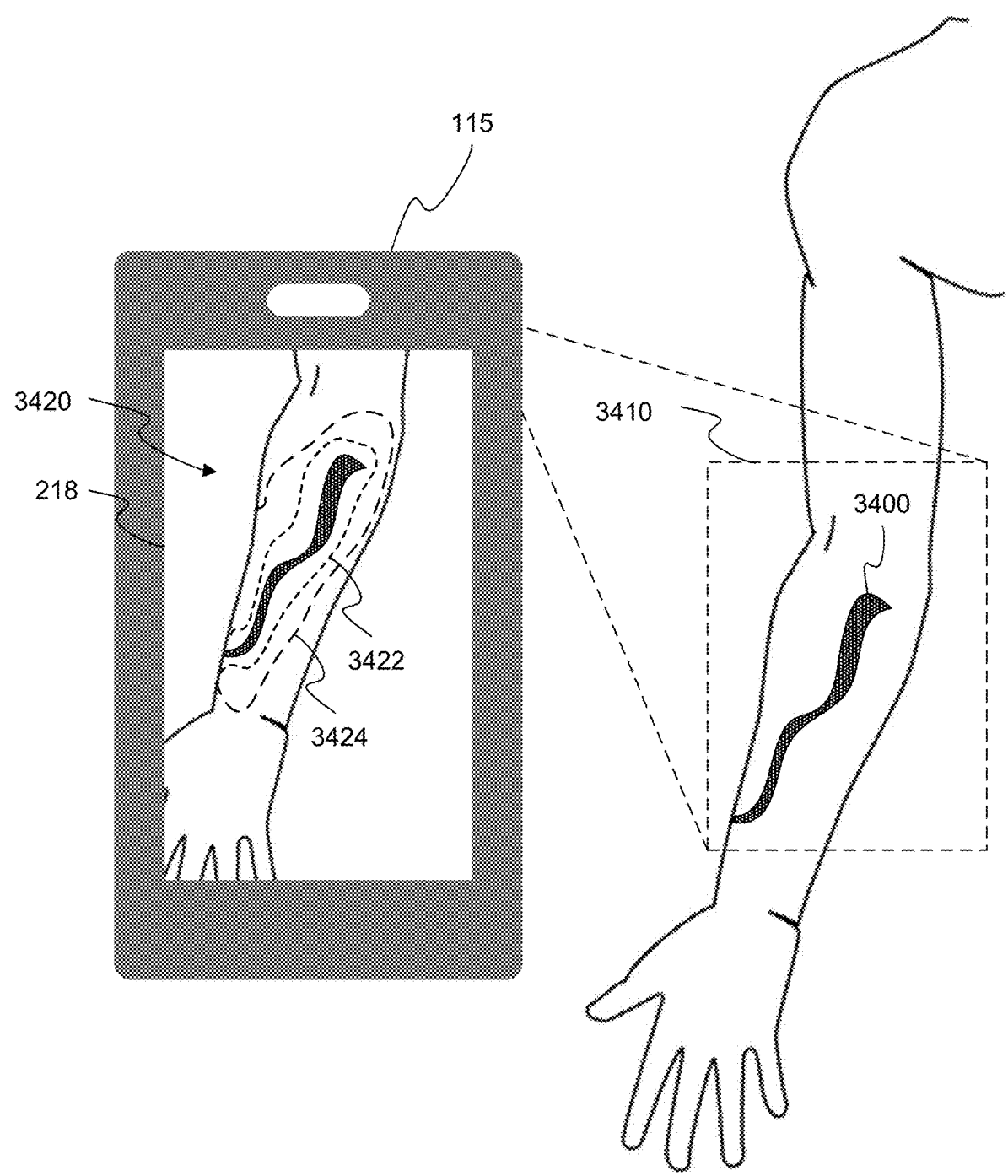
FIG. 34 is an illustration of an example mobile device configured to display an overlay on one or more wounds in a video feed, consistent with some embodiments of the present disclosure.

By way of example, FIG. 34 illustrates an example mobile communications device 115 that is configured to display overlay 3420 on an image 3410 of wound 3400 in a video feed displayed on touch screen 218, consistent with some embodiments of the present disclosure. Overlay 3420, as displayed on touch screen 218, may include elements 3422 and 3424 that are superimposed on wound 3400 in image 3410. Although not illustrated herein, the image as displayed on touch screen 218 may be a representation of the image viewed by a user through a transparent surface (e.g., a window or augmented reality glasses) that is configured to display overlay 3420 such that elements 3422 and 3424 are superimposed on wound 3400 to the user. Accordingly, unless expressly stated otherwise, touch screen 218 is to be understood to illustrate that the disclosed overlays may be displayed on any graphical user interface, such as a non-touch screen display or a transparent surface configured for displaying an overlay.

Figure 35:
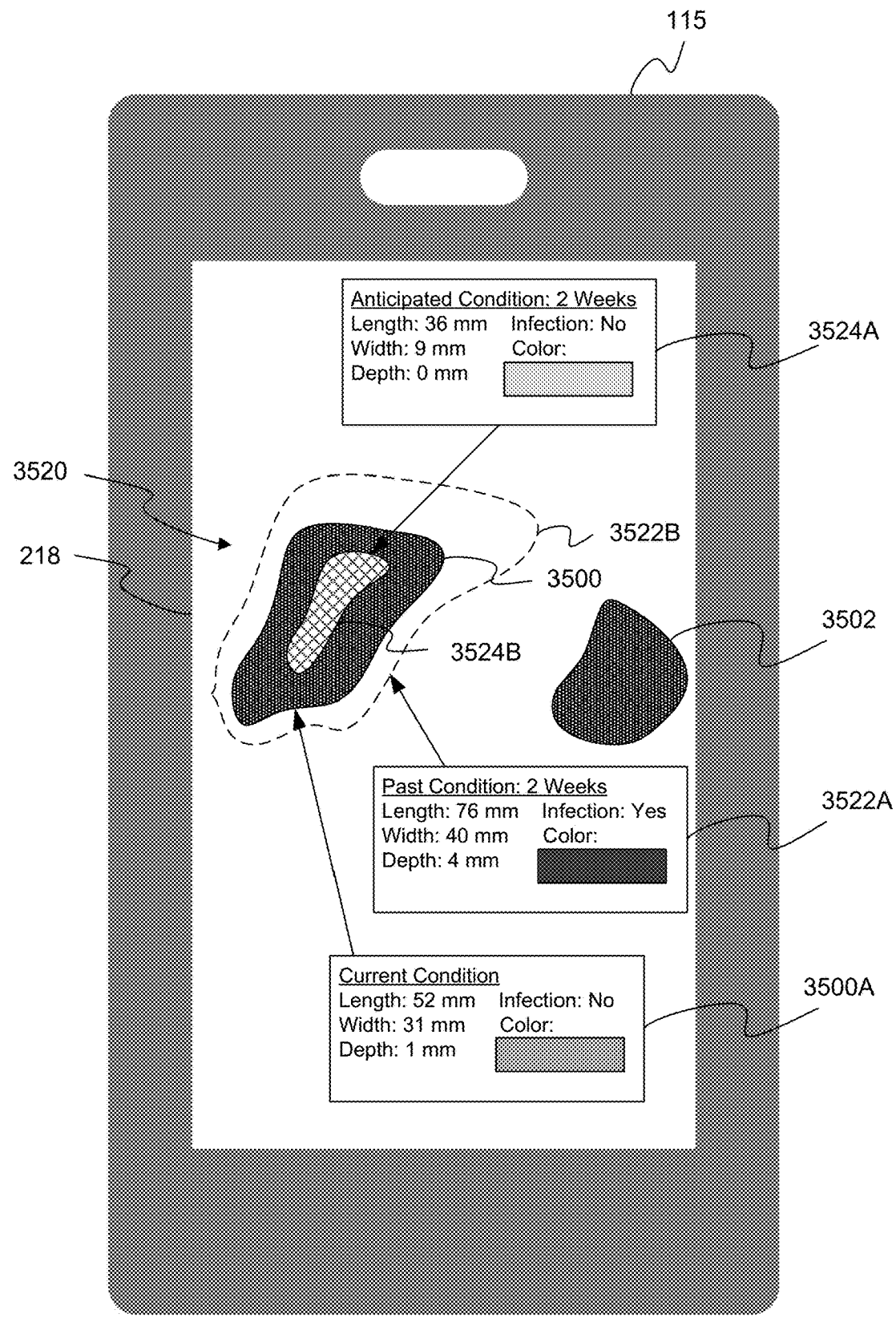
FIG. 35 is an illustration of another example device configured to display an overlay on one or more wounds in a video feed, consistent with some embodiments of the present disclosure.

Embodiments consistent with the present disclosure may include receiving a real time video feed. A real time video feed as referred to herein may include a plurality of images that have been captured by an imaging device, or it may include a plurality of images that are being captured in real-time. The subject of the captured images may include a single wound or a plurality of wounds. Some embodiments consistent with the present disclosure may also include selecting a wound from a plurality of wounds in the image. The selected wound may, for example, be a wound that a user selects to be provided with an overlay or element of an overlay. A wound may be selected through any suitable means according to the type of interface used. For example, selecting a wound may include clicking on a displayed image of a wound, touching a displayed image wound on a touch screen, providing verbal or non-verbal (e.g., gestures) instructions to the user interface to select the wound, and the like. By way of example, FIG. 35 illustrates an example mobile communications device 115 that is configured to display overlay 3520 on an image of wound 3500 in a video feed displayed on touch screen 218, consistent with some embodiments of the present disclosure. The video feed on which overlay 3520 is displayed may be previously recorded or viewed and/or displayed in real-time and may include images of both wound 3500 and wound 3502. Although overlay 3520 is displayed on touch screen 218 as being superimposed on wound 3500, touch screen 218 may alternatively or additionally display an overlay on wound 3502 if wound 3502 is selected by the user. In some examples, at least part of the video feed may be analyzed to automatically select the wound from the plurality of wounds. For example, information related to a particular wound may be used to generate the overlay, for example by visually presenting at least part of the information related to the particular wound in the overlay. The information related to the particular wound may be based on image-based information associated with at least one previously captured image of the particular wound, for example as described below. Further, the information related to the particular wound may be used to select the wound corresponding to the information from the plurality of wounds. In one example, the information related to the particular wound may include a size of the particular wound, and a wound of the plurality of wounds with a size nearest to the size of the particular wound may be selected. The size of each wound of the plurality of wounds may be determined by analyzing the at least part of the video feed. In another example, the information related to the particular wound may include a shape of the particular wound, and a wound of the plurality of wounds with a shape most resembling to the shape of the particular wound may be selected. The shape of each wound of the plurality of wounds may be determined by analyzing the at least part of the video feed. In some examples, a machine learning model may be trained using training examples to select a wound of a plurality of wounds in an image that corresponds to particular wound characteristics. An example of such training example may include a sample image depicting a sample plurality of wounds and one or more sample characteristics of a desired wound, together with a label indicating a wound of the sample plurality of wounds corresponding to the one or more sample characteristics. The trained machine learning model may be used to analyze the at least part of the video feed and automatically select the wound from the plurality of wounds.

Embodiments consistent with the present disclosure may include receiving image-based information associated with at least one previously captured image of a wound. Image-based information as referred to herein may include data comprising the previously captured image (e.g., digital images formatted with PNG, JPEG, GIF, and the like), data associated with the previously captured image (e.g., a time of capture of the image, patient information, wound information, etc.), or any data generated based on the image using computer vision and/or image processing as discussed herein. The previously captured image may be captured at any time prior to a time at which the video feed is captured (e.g., seconds, hours, days, weeks, etc.), for example at least one day before the video feed is captured.

In some embodiments, receiving the image-based information may include accessing a plurality of records, selecting a record corresponding to the wound of the plurality of records based on the video feed, and obtaining the image-based information from the selected record. A record as used herein may refer to a digital file or collection of data or information that has been previously recorded or saved into storage. Records may be stored in any suitable data structure, such as a database (e.g., databases 146 and 166 in FIG. 1A) or local memory (e.g., memory device 234 in FIG. 2). In some embodiments, each record in the plurality of records may correspond to a different wound. In some examples, at least part of the video feed may be analyzed to determine characteristics of the wound (such as size, shape, location on the body, tissue composition, etc.), and the record corresponding to the wound may be selected from the plurality of records based on the determined characteristics. For example, a record that best matches the determined characteristics of the plurality of records may be selected. In some examples, a machine learning model may be trained using training examples to select records corresponding to wounds based on images of the wounds. An example of such a training example may include a plurality of sample records and a sample image of a sample wound, together with a label indicating a record from the plurality of sample records corresponding to the sample wound. The trained machine learning model may be used to analyze the at least part of the video feed and select the record from the plurality of records. Some disclosed embodiments may include receiving second, third, or any further image-based information associated with a second, third, or further at least one previously captured image of the wound. In some examples, a record may include one or more images and associated data of the respective wound. For example, a record corresponding to a particular wound may contain several previously captured images, and the previously captured images may have been captured at different times. By way of example, in FIG. 34, superimposed elements 3422 and 3424 may correspond to images of wound 3400 that were captured at different points in time in the past. Elements 3422 and 3424 of overlay 3420 may be generated, for example as discussed with further detail herein, based on images contained in one or more records stored in a database (e.g., databases 146 and 166 in FIG. 1A) or local memory (e.g., memory device 234 in FIG. 2).

Embodiments consistent with the present disclosure may include generating an overlay using a video feed and image-based information. The overlay may include an indication of a condition of the wound in the at least one previously captured image. An indication as referred to herein may refer to a superimposed element or a non-superimposed element of an overlay. In some non-limiting examples, an indication may be textual, graphical, a combination of a text with graphics, and so forth. In another non-limiting example, the information contained in the indication may be provided audibly. In some embodiments, for example, the overlay may include an indication of a capturing time associated with a first, second, third, and/or further at least one previously captured image. The capturing time may be an absolute point in time (i.e., a specific date and time of capture) or a relative point in time (e.g., one week ago, two months ago, etc.) In some embodiments, the overlay may include a second, third or further indication. The second, third, or further indication may be an indication of a condition of the wound in the second at least one previously captured image. The condition of the wound in the second at least one previously captured image may differ from the condition of the wound in the at least one previously captured image. In other words, in some embodiments, the overlay may include indications corresponding to any number of previously captured images to provide information associated with a condition of the wound in each respective previously captured image.

By way of example, in FIG. 35, the generated overlay 3520 may include non-superimposed elements 3500A, 3522A, and 3524A, and superimposed elements 3522B and 3524B. Non-superimposed elements 3500A, 3522A, and 3524A may correspond with wound 3500 and superimposed elements 3522A and 3524B, respectively. Elements 3522A and 3522B may be generated using the video feed (e.g., to correspond a location of the wound with a location of superimposed element 3522B) and image-based information from a record associated with at least one previously captured image of wound 3500. Non-superimposed element 3522A may include an indication of a relative capturing time of the at least one image (i.e., "Past Condition: 2 Weeks") associated with the indication. Moreover, as illustrated in FIG. 34, overlay 3420 may include multiple indications associated with previously captured images of wound 3400. For example, element 3422 may correspond to an image captured at a more recent point in time (e.g., a week), whereas element 3424 may correspond to an image captured at a less recent point in time (e.g., a month). Although not explicitly illustrated therein, superimposed elements 3422 and 3424 may include an indication of a capturing time of each respective image, or overlay 3420 may include additional non-superimposed elements including an indication of the capturing time of each respective image.

Consistent with disclosed embodiments, generating the overlay may involve image processing, as discussed previously herein. In some embodiments, generating the overlay may include combining the geometry and attributes of multiple different data sets (e.g., image data associated with the video feed and image data associated with at least one previously captured image). In some non-limiting examples, generating the overlay may include combining Vector data sets, Raster data sets, or both. Vector data, for example, may provide data for correlating features of an image with its geometry and attribute. The geometry data may include data indicative of points (0-dimensional), lines (1-dimensional), polygons (2-dimensional), and/or volumes (3-dimensional) associated with a certain feature. Some non-limiting examples of Vector data formats include Shapefile, geodatabase feature class, GML, KML, and GeoJSON. Raster data may include Raster grids, which are typically made up of square or rectangular grids with a single value corresponding to each cell, thus representing a 2-dimensional array of samples. Some non-limiting overlaying functions may include intersection (including only features present in all input layers), union (including only features occurring in either or both input layers), subtraction (excluding overlapping features of input layers), symmetric difference (including all features that occur in one of the input layers but not all input layers), identity (for one of the input layers, merging features of overlapping input layers), cover (similar to union, where one layer is retained in areas of overlapping features), and clip (cropping an input layer to areas where features of other input layers overlap).

The digital data for providing the overlay may be initially generated with photo interpretation of the images in the video feed and/or with at least one previously captured image. Photo interpretation may be configured to capture 2-dimensional and 3-dimensional data, with elevations measured using one or more photogrammetric methods (e.g., stereophotogrammetry). Although disclosed embodiments may be described with reference to previously captured images or images from a video feed, other remote sensing technologies may be used to collect 2-dimensional and 3-dimensional data associated with a wound or other physical feature to generate an overlay, consistent with some embodiments of the present disclosure. Some non-limiting examples of remote sensing technologies include radar, LIDAR, radiometry, and multi-spectral mapping.

Some embodiments may include a system for displaying an overlay on a wound, the system comprising at least one processing unit configured to: receive a real time video feed; receive image-based information associated with at least one previously captured image of a wound; generate, using the video feed and the image-based information, an overlay including an indication of a condition of the wound in the at least one previously captured image; and display, on at least one user interface, the overlay, wherein the at least one user interface is configured to display the overlay in a position associated with a position of the wound in the video feed.

Other embodiments may include a method for displaying an overlay on a wound in, the method comprising: receiving a real time video feed; receiving image-based information associated with at least one previously captured image of a wound; generating, using the video feed and the image-based information, an overlay including an indication of a condition of the wound in the at least one previously captured image; and displaying, on at least one user interface, the overlay, wherein the at least one user interface is configured to display the overlay in a position associated with a position of the wound in the video feed.

In some disclosed embodiments, generating an overlay may include calculating a convolution, as discussed previously herein, of at least part of the at least one previously captured image to derive a result value. The result value may then be used to generate an indication associated with the result value. For example, in response to a first result value, the overlay may include a first indication of the condition of the wound in the at least one previously captured image. In response to a second result value, the overlay may include a second indication of the condition of the wound in the at least one previously captured image, where the second indication differs from the first indication. By way of example, in FIG. 34, elements 3422 and 3424 may correspond to alternative indications (e.g., a first indication or a second indication) of a shape of a wound in at least one previously captured image. A result value of the calculated convolution of the wound in the at least one previously captured image may correspond to the shape indicated by element 3422 and not element 3424. Accordingly, element 3422 may be displayed on overlay 3420 instead of element 3424.

Consistent with the present disclosure, a condition of a wound as referred to herein may refer to a medical condition (e.g., infection) or any other physical parameter associated with a wound. For example, in some embodiments, an indication of a condition of a wound included in an overlay may include at least one of an indication, including in some cases visual indications, of a contour or shape of a wound at least one measurement of the wound in the at least one previously captured image (e.g length, an area, a volume, or a depth of the wound, etc.), a tissue type (e.g., granulation tissue, slough tissue, eschar, necrotic tissue, scab, hematoma, tendon, ligament, bone, infected tissue, non-infected tissue, etc.) of at least one segment of the wound in the at least one previously captured image corresponding to a tissue type, a color of a portion of the wound in the at least one previously captured image, a severity of the wound in the at least one previously captured image, or any other conceivable characteristic that may be associated with a wound. By way of example, in FIG. 35, overlay 3520 may include non-superimposed elements 3500A, 3522A, and 3524A, each of which provide a textual indication of length, width, and depth measurements, color of the wound, and infection status of the wound. In contrast, superimposed elements 3522B and 3524B provide a visual indication of the size, shape, and contours of wound 3500.

Some embodiments of the present disclosure may include determining a condition of a wound in at least one image. A condition associated with a wound may, for example, be determined by a medical professional (e.g., medical practitioner 120 in FIG. 1A) and placed into a record corresponding to the wound (e.g., saved in database 146). However, some embodiments of the disclosure may include using machine learning, as previously discussed herein, to determine a condition of a wound or to estimate and/or interpolate a condition of a wound. For example, in some embodiments, a machine learning model (e.g., a generative model, such as a generative adversarial network, a transformers-based model, etc.) may be trained using training examples to determine one or more conditions of a wound in one or more images or to estimate and/or interpolate a condition of a wound at a certain point in time. Examples of training examples for determining a condition of a wound may include sample images of wounds having known conditions (e.g., an infected wound with predetermined measurements, color, tissue types, etc.). For estimating and/or interpolating the condition of a wound, examples of training examples may include sets of sample images of wounds with known conditions, where each set may include multiple images of the same wound at multiple times with time stamps for the times at which each of the images is captured. The trained machine learning model may be used to analyze 3D information associated with one or more images in the video feed and/or at least one previously captured image to determine a condition of the wound in the one or more images or to estimate and/or interpolate a condition of a wound at a certain point in time.

As previously discussed, some disclosed embodiments may include extrapolating and/or determining a condition of a wound at a certain point in time. For example, in some disclosed embodiments, a condition of a wound in the at least one previously captured image may correspond to a first point in time, and a condition of the wound in a second at least one previously captured image may correspond to a second point in time. Where the condition of a wound in a different or third point in time is unknown, the image-based information associated with the first at least one previously captured image and the second image-based information may be used to determine a condition of the wound corresponding to a third point in time. A third indication in the overlay indicating the condition of the wound corresponding to the third point in time may be included in the overlay. In one example, the third point in time may be a future point in time, and the condition of the wound corresponding to the third point in time may be a predicted condition of the wound in the future. In another example, the third point in time may be a point in time between the first point in time and the second point in time, and the condition of the wound corresponding to the third point in time may be an interpolation. In yet another example, the third point in time may be a point in time before the first point in time and the second point in time, and the condition of the wound corresponding to the third point in time may be an extrapolation. In an additional example, the third point in time may be a point in time after the first point in time and the second point in time, and the condition of the wound corresponding to the third point in time may be an extrapolation. In some examples, the first point in time may also refer to one or more times at which one or more images in the video feed are captured.

By way of example, in FIG. 34, element 3424 may correspond to a first point in time at which an image of wound 3400 was previously captured, and image 3410 of wound 3400 may be captured at a second point in time. In some embodiments, at least one processor (e.g., processing device 202 of mobile communications device 115 or server 145) may use machine learning or other computerized methods to interpolate a condition of wound 3400 at a third point in time between the first point in time and the second point in time. An indication of the condition of wound 3400 may be displayed, for example, as element 3422 in overlay 3420.

By way of further example, in FIG. 35, elements 3522A and 3522B may correspond to a first point in time at which an image of wound 3500 was captured, and the image of wound 3500 displayed on overlay 3520 may be captured at a second point in time. In some embodiments, at least one processor may use machine learning or other computerized methods (e.g., processing device 202 of mobile communications device 115 or server 145) to predict a condition of wound 3500 at a third point in time (i.e., a future point in time) that is after the first point in time and the second point in time. An indication of the condition of wound 3400 may be displayed, for example, as elements 3524A and 3524B, including an indication of the future point in time (i.e., "Anticipated Condition: 2 Weeks"). Similarly, in some embodiments, if the condition of wound 3500 at the point of time associated with element 3524A and 3524B is known (e.g., indication 3524B instead represents an image of wound 3500 captured at a first point in time, and the image of wound 3500 displayed on touch screen 218 illustrated in FIG. 35 instead represents a previously captured image captured at a second point in time), the at least one processor may extrapolate a condition of the wound 3500 at a third point in time that is after the first point in time and after the second point in time. In some embodiments, the at least one processor may extrapolate a condition of the wound 3500 at a third point in time that is before the first point in time and the second point in time. In this example, indications 3522A and 3522B may correspond to the estimated condition of wound 3500 at the third point in time. In yet other embodiments, the at least one processor may interpolate a condition of the wound 3500 at a third point in time that is after the first point in time but before the second point in time.

Embodiments consistent with the present disclosure may include displaying the overlay on at least one user interface. The at least one user interface may be configured to display the overlay in a position associated with a position of the wound in the video feed. In some embodiments, the at least one user interface may be associated with a mobile device. For example, the user interface may be displayed along with the video feed in mobile devices with integrated display elements, such as smartphones or tablets. However, as discussed previously herein, the at least one user interface is not to be limited to such mobile devices. For example, the at least one user interface may be associated with an extended reality system. Some non-limiting examples of extended reality systems include virtual reality systems, augmented reality systems, mixed reality systems, augmented reality glasses, head mounted extended reality systems, wearable extended reality systems, and so forth.

For example, in some embodiments, the overlay may be displayed using a transparent optical system included in a wearable device, and the video feed may be captured using an image sensor included in the wearable device. Accordingly, a wound may be visible to a user wearing the wearable device through the transparent optical system, and the display of the overlay may be configured to make the overlay appear to the user wearing the wearable device at least partly over the wound. By way of example, the images displayed on touch screen 218 of mobile communications device 115 illustrated in FIGS. 34 and 35 may instead represent an image of the wound as viewed by a user that is directly viewing the wound through a transparent surface. In other words, the image of wounds 3400 and 3500 may, in the case that the user interface is associated with a transparent optical system, represent actual images of the wounds instead of computer-generated images. In this example, overlays 3420 and 3520 may be displayed on the transparent surface, for example using a projector or using a transparent display screen.

In some embodiments, the overlay may be displayed on the user interface feed in real time. That is, the overlay may be displayed on the user interface virtually instantaneously as the video feed is captured. Accordingly, if the video feed is captured using a device associated with the user interface (i.e., if the video is captured from a similar point of view to the point of view of the user), the user interface may cause the overlay to appear as if the overlay is superimposed on the actual image (e.g., augmented reality systems). In some embodiments, the video feed may be captured at a separate location than the user interface, and the user interface may be configured to use the video feed to display a plurality of new computer-generated images including the overlay depicting the separate location, such that the user interface may cause the separate location to appear as if it is in the same location as the user (e.g., virtual reality systems).

In some embodiments consistent with the present disclosure, the at least one user interface may be configured to automatically adjust the position of the displayed overlay based on detected movement of the device capturing the video feed. For example, a user interface with a displayed overlay may automatically move the overlay in response to movement of the device, such that the displayed overlay appears to move in conjunction with the image of the wound. In some embodiments, the movement may be detected based on an analysis of the video feed. For example, the motion may be determined, at least in part, based on an analysis of the plurality of images in the video feed captured by at least one image sensor (e.g., image sensor 226 depicted in FIG. 2) of the device. The analysis of the plurality of images may be conducted with an egomotion algorithm, for example. Additionally or alternatively, the movement may be detected based on information received from at least one motion sensor associated with the mobile device. Motion sensors (e.g., motion sensor 228 depicted in FIG. 2) may include accelerometers, gyroscopes, or any other sensor configured to measure acceleration, gravity, speed of revolution, curl vector values, or drift of the mobile device. In some embodiments, a correspondence between the actual movement of the device detected using the image sensors and/or motion sensors and a computed position of the overlay on the image may be determined (e.g., using a local and/or global positioning system) and used to modify the display of the overlay on the user interface accordingly.

By way of example, in FIG. 34, mobile communications device 115 may be moved by the user to different positions, and the position of overlay 3420 on touch screen 218 may move in order to maintain its position relative to the displayed image of wound 3400. The movement may be based on one or both of image data collected from at least one image sensor (e.g., image sensor 226 in FIG. 2) or at least one motion sensor (e.g., motion sensor 228 in FIG. 2) associated with mobile communication device 115. For example, if mobile communications device 115 moves upwards without changing orientation, overlay 3420 as displayed on touch screen 218 will move downwards along with the corresponding portion of wound 3400. In another example, if mobile communications device 115 were moved to view wound 3400 at an angle perpendicular to the radial portion of the forearm, the orientation of overlay 3420 as displayed on touch screen 218 would change consistently with the changing orientation of the wound in the video feed.

Figure 36:
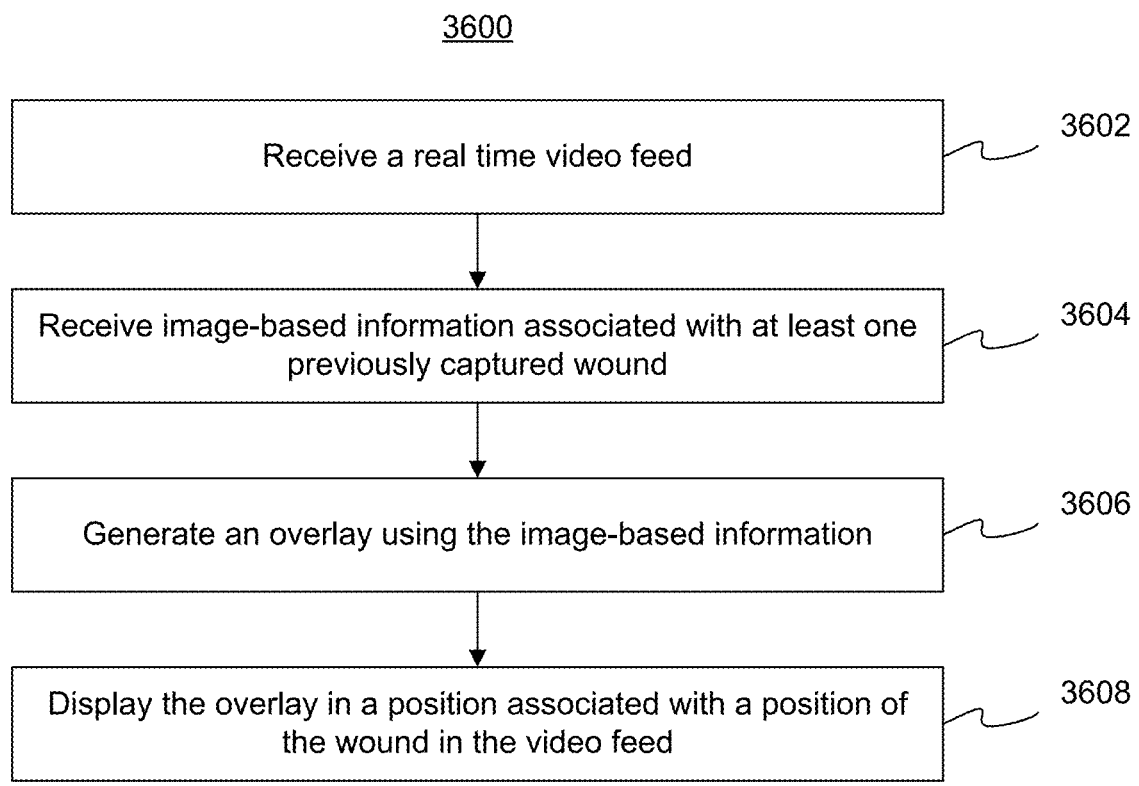
FIG. 36 is a flowchart of an example process for displaying an overlay on one or more wounds in a video feed, consistent with some embodiments of the present disclosure.

FIG. 36 provides a flowchart of an example process 3600 for displaying an overlay on wounds in a video feed. Process 3600 includes steps 3602 through 3608, which may be executed by at least one processor (e.g., processing device 202 of communications device 115 or server 145), consistent with some embodiments of the present disclosure. Although process 3600 is illustrated as a sequence, it is to be understood that two or more of the steps may be executed concurrently, and the entire process may be executed in real-time, as discussed previously herein.

Process 3600 may begin with step 3602. At step 3602, the at least one processor may receive a real time video feed from at least one image sensor (e.g., image sensor 226) associated with a mobile device (e.g., mobile communications device 115), consistent with some embodiments of the present disclosure. Then, at step 3604, the at least one processor may receive image-based information associated with at least one previously captured image of a wound (e.g., wounds 3400 and 3500), consistent with some embodiments of the present disclosure. For example, the at least one processor may access at least one data structure (e.g., database 146) to retrieve data associated with the at least one captured image.

After the image-based information has been received, process 3600 may proceed to step 3606. At step 3606, the at least one processor may generate, using the video feed and the image-based information, an overlay (e.g., overlays 3420 and 3520) including at least one indication (e.g., elements 3422, 3424, 3500A, 3522A, 3522B, 3524A, and 3524B) of a condition of the wound in the at least one previously captured image, consistent with some embodiments of the present disclosure. Process 3600 may end at step 3608. At step 3608, the at least one processor may display the overlay on at least one user interface (e.g., touch screen 218), consistent with some embodiments of the present disclosure. The at least one user interface may be configured to display the overlay in a position associated with (e.g., superimposed on) a position of the wound in the video feed.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, e.g., hard disks or CD ROM, or other forms of RAM or ROM, USB media, DVD, Blu-ray, Ultra HD Blu-ray, or other optical drive media.

Computer programs based on the written description and disclosed methods are within the skills of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The examples are to be construed as non-exclusive. Furthermore, the steps of the disclosed methods may be modified in any manner, including by reordering steps and/or inserting or deleting steps. It is intended, therefore, that the specification and examples be considered as illustrative only.

What is claimed is:

1. A non-transitory computer readable medium storing data and computer implementable instructions that, when executed by at least one processor, cause the at least one processor to perform operations for generating cross section views of a wound, the operations comprising:

receiving 3D information of a wound based on information captured using an image sensor associated with an image plane substantially parallel to the wound;

generating a cross section view of the wound by analyzing the 3D information, wherein the generated cross section view of the wound includes a plurality of parallel cross section views of the wound; and providing data configured to cause a presentation of the generated cross section view of the wound.

2. The non-transitory computer readable medium of claim 1, wherein the 3D information of the wound includes at least one of a range image, a stereoscopic image, a volumetric image, or a point cloud.

3. The non-transitory computer readable medium of claim 1, wherein receiving the 3D information of the wound includes one or more of analyzing a video of the wound captured using the image sensor while the image sensor is moving, analyzing a video of the wound depicting a motion of the wound, or analyzing at least one image captured using the image sensor.

4. The non-transitory computer readable medium of claim 1, wherein the 3D information of the wound includes at least one of a plurality of 2D images of the wound captured from different angles, a stereoscopic image of the wound, an image captured using an active stereo camera, or an image captured using a time-of-flight camera.

5. The non-transitory computer readable medium of claim 1, wherein generating the cross section view of the wound includes:

selecting a cross section of the wound from a plurality of cross sections of the wound based on the 3D information; and generating the cross section view of the wound by analyzing the 3D information, the cross section view of the wound corresponding to the selected cross section.

6. The non-transitory computer readable medium of claim 5, wherein the selected cross section of the wound corresponds to a deepest point of the wound.

7. The non-transitory computer readable medium of claim 1, wherein generating the cross section view of the wound includes:

selecting a cross section of the wound from a plurality of cross sections of the wound based on a boundary contour of the wound; and generating the cross section view of the wound by analyzing the 3D information, the cross section view of the wound corresponding to the selected cross section.

8. The non-transitory computer readable medium of claim 7, wherein the selected cross section of the wound corresponds to one of a longest chord of a shape of the boundary contour or a shortest chord of the shape of the boundary contour.

9. The non-transitory computer readable medium of claim 7, wherein the selected cross section of the wound is perpendicular to one or more of a selected chord of a shape of the boundary contour.

10. The non-transitory computer readable medium of claim 1, wherein generating a cross section view of the wound includes:

obtaining a segmentation of the wound based on a tissue type;

selecting a cross section of the wound of a plurality of cross sections of the wound based on the segmentation of the wound; and generating the cross section view of the wound by analyzing the 3D information, the cross section view of the wound corresponding to the selected cross section.

11. The non-transitory computer readable medium of claim 1, wherein the generated cross section view of the wound includes one or more of tissue information for at least a portion of the wound, a visual indication of a wound depth, an estimated pre-wound skin contour, or an estimated post-wound skin contour.

12. The non-transitory computer readable medium of claim 1, the operations further comprising:
receiving image data captured using the image sensor;
calculating a convolution of a first part of the image data to derive a first result value of the convolution of the first part of the image data;
determining a depth of the wound at a first position based on the first result value;
calculating a convolution of a second part of the image data to derive a second result value of the convolution of the second part of the image data, the second part of the image data differing from the first part of the image data; and
determining a depth of the wound at a second position based on the second result value, the second position differing from the first position.

13. The non-transitory computer readable medium of claim 1, the operations further comprising estimating at least one of an original position of a skin before a formation of the wound or a future position of the skin after healing of the wound by analyzing the 3D information, and wherein the provided data is based on at least one of the estimated original position of the skin or the future position of the skin.

14. The non-transitory computer readable medium of claim 13, wherein the provided data includes a depth of the wound estimated based on at least one of the estimated original position of the skin or the estimated future position of the skin.

15. The non-transitory computer readable medium of claim 13, wherein the generated cross section view of the wound includes a visual indication of at least one of the original position of the skin or the future position of the skin.

16. The non-transitory computer readable medium of claim 13, wherein at least one of estimating the original position of the skin or estimating the future position of the skin includes implementing an inpainting algorithm based on the 3D information.

17. The non-transitory computer readable medium of claim 13, wherein the wound corresponds to a first body part of a patient, the patient having a symmetrical body part to the first body part, and wherein at least one of estimating the original position of the skin or estimating the future position of the skin includes:
receiving 3D information of the symmetrical body part; and
analyzing the 3D information of the symmetrical body part and the 3D information of the wound.

18. A system for generating cross section views of a wound, the system comprising:
a memory storing instructions; and
at least one processor configured to execute the instructions to:
receive 3D information of a wound based on information captured using an image sensor associated with an image plane substantially parallel to the wound;
generate a cross section view of the wound by analyzing the 3D information, wherein the generated cross section view of the wound includes a plurality of parallel cross section views of the wound; and
provide data configured to cause a presentation of the generated cross section view of the wound.

19. A computer-implemented method for generating cross section views of a wound, the method comprising:
receiving 3D information of a wound based on information captured using an image sensor associated with an image plane substantially parallel to the wound;
generating a cross section view of the wound by analyzing the 3D information, wherein the generated cross section view of the wound includes a plurality of parallel cross section views of the wound; and
providing data configured to cause a presentation of the generated cross section view of the wound.

* * * * *